United States Patent
Wada et al.

(10) Patent No.: US 6,592,821 B1
(45) Date of Patent: Jul. 15, 2003

(54) FOCUSING OF MICROPARTICLES IN MICROFLUIDIC SYSTEMS

(75) Inventors: H. Garrett Wada, Atherton, CA (US); Anne R. Kopf-Sill, Portola Valley, CA (US); Marja Liisa Alajoki, Palo Alto, CA (US); J. Wallace Parce, Palo Alto, CA (US); Benjamin N. Wang, Palo Alto, CA (US); Andrea W. Chow, Los Altos, CA (US); Robert S. Dubrow, San Carlos, CA (US); Yevgeny Yurkovetsky, San Jose, CA (US); Javier Anibal Farinas, San Carlos, CA (US)

(73) Assignee: Caliper Technologies Corp., Mountain View, CA (US)

( * ) Notice: Subject to any disclaimer, the term of this patent is extended or adjusted under 35 U.S.C. 154(b) by 217 days.

(21) Appl. No.: 09/853,887

(22) Filed: May 10, 2001

Related U.S. Application Data

(63) Continuation-in-part of application No. 09/569,747, filed on May 11, 2000, now Pat. No. 6,506,609.
(60) Provisional application No. 60/134,472, filed on May 17, 1999.

(51) Int. Cl.$^7$ .............................................. G01N 33/48
(52) U.S. Cl. ...................... 422/68.1; 422/50; 422/58; 422/81; 422/82.05; 422/82.08; 422/82.09; 436/43; 436/63; 435/4; 435/7.1
(58) Field of Search ........................... 422/50, 58, 68.1, 422/81, 82.05, 82.08, 82.09; 436/63, 148, 34, 52, 180, 518; 435/91.1, 7.1, 6; 204/452, 454, 600; 356/73; 210/634

(56) References Cited

U.S. PATENT DOCUMENTS 4,390,403 A   6/1983 Batchelder
4,908,112 A   3/1990 Pace
5,126,022 A   6/1992 Soane et al.

(List continued on next page.)

FOREIGN PATENT DOCUMENTS

| WO | WO 96/04547 | 2/1996 |
| WO | WO 97/02357 | 1/1997 |
| WO | WO 98/00231 | 1/1998 |

(List continued on next page.)

OTHER PUBLICATIONS

Cohen, C.B. et al., "A Microchip–Based Enzyme Assay for Protein Kinase A," *Anal. Chem.* (1999) 273:89–97.
Dasgupta, P.K. et al., "Electroosmosis: A Reliable Fluid Propulsion System for Flow Injection Analysis," *Anal. Chem.* (1994) 66:1792–1798.
Jacobson, S.C. et al., "Fused Quartz Substrates for Microchip Electrophoresis," *Anal. Chem.* (1995) 67:2059–2063.
Manz, A. et al., "Electroosmotic pumping and electrophoretic separations for miniaturized chemical analysis system" *J. Micromech. Microeng.* (1994) 4:257–265.
Ramsey, J.M. et al., "Microfabricated chemical measurement systems," *Nature Med.* (1995) 1:1093–1096.

(List continued on next page.)

*Primary Examiner*—Jill Warden
*Assistant Examiner*—Brian Sines
(74) *Attorney, Agent, or Firm*—Andrew L. Filler; Quine Intellectual Property Law Group

(57) ABSTRACT

Methods and systems for particle focusing to increase assay throughput and sensitivity in microscale systems are provided. The invention includes methods for providing substantially uniform flow velocity to flowing particles in microfluidic devices. Methods of sorting members of particle populations, such as cells and various subcellular components are also provided. Integrated systems in which particles are focused and/or sorted are additionally included.

15 Claims, 43 Drawing Sheets

U.S. PATENT DOCUMENTS

| | | | |
|---|---|---|---|
| 5,498,392 | A | 3/1996 | Wilding et al. |
| 5,571,410 | A | 11/1996 | Swedberg et al. |
| 5,585,069 | A | 12/1996 | Zanzucchi et al. |
| 5,587,128 | A | 12/1996 | Wilding et al. |
| 5,593,838 | A | 1/1997 | Zanzucchi et al. |
| 5,603,351 | A | 2/1997 | Cherukuri et al. |
| 5,635,358 | A | 6/1997 | Wilding et al. |
| 5,637,469 | A | 6/1997 | Wilding et al. |
| 5,699,157 | A | 12/1997 | Parce |
| 5,750,015 | A | 5/1998 | Soane et al. |
| 5,779,868 | A | 7/1998 | Parce et al. |
| 5,800,690 | A | 9/1998 | Chow et al. |
| 5,842,787 | A | 12/1998 | Kopf-Sill et al. |
| 5,846,708 | A * | 12/1998 | Hollis et al. ............. 435/6 |
| 5,852,495 | A | 12/1998 | Parce |
| 5,869,004 | A | 2/1999 | Parce et al. |
| 5,876,675 | A | 3/1999 | Kennedy |
| 5,880,071 | A | 3/1999 | Parce et al. |
| 5,882,465 | A | 3/1999 | McReynolds |
| 5,885,470 | A | 3/1999 | Parce et al. |
| 5,942,443 | A | 8/1999 | Parce et al. |
| 5,948,227 | A | 9/1999 | Dubrow |
| 5,955,028 | A | 9/1999 | Chow |
| 5,957,579 | A | 9/1999 | Kopf-Sill et al. |
| 5,958,203 | A | 9/1999 | Parce et al. |
| 5,958,694 | A | 9/1999 | Nikiforov |
| 5,959,291 | A | 9/1999 | Jensen |
| 5,964,995 | A | 10/1999 | Nikiforov et al. |
| 5,965,001 | A | 10/1999 | Chow et al. |
| 5,965,410 | A | 10/1999 | Chow et al. |
| 5,972,187 | A | 10/1999 | Parce et al. |
| 5,972,710 | A * | 10/1999 | Weigl et al. ............. 436/34 |
| 5,976,336 | A | 11/1999 | Dubrow et al. |
| 5,989,402 | A | 11/1999 | Chow et al. |
| 6,001,231 | A | 12/1999 | Kopf-Sill |
| 6,004,515 | A | 12/1999 | Parce et al. |
| 6,011,252 | A | 1/2000 | Jensen |
| 6,012,902 | A | 1/2000 | Parce |
| 6,042,710 | A | 3/2000 | Dubrow |
| 6,046,056 | A | 4/2000 | Parce et al. |
| 6,068,752 | A | 5/2000 | Dubrow et al. |
| 6,071,478 | A | 6/2000 | Chow |
| 6,074,725 | A | 6/2000 | Kennedy |
| 6,080,295 | A | 6/2000 | Parce et al. |
| 6,156,181 | A | 12/2000 | Parce et al. |
| 6,344,326 | B1 * | 2/2002 | Nelson et al. ............. 435/6 |
| 6,432,630 | B1 * | 8/2002 | Blankenstein ............. 435/4 |

FOREIGN PATENT DOCUMENTS

| | | |
|---|---|---|
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 00/09753 | 2/2000 |
| WO | WO 01/14064 | 3/2001 |

OTHER PUBLICATIONS

Seiler, K. et al., "Planar Glass Chips for Capillary Electrophoresis: Repetitive Sample Injection, Quantitation, and Separation Effciency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

Sundberg, S. A., "High–throughput and ultra–high–throughput screening: solution— and cell–based approches," *Current Opinions in Biotechnology* 2000, 11:47–53.

* cited by examiner

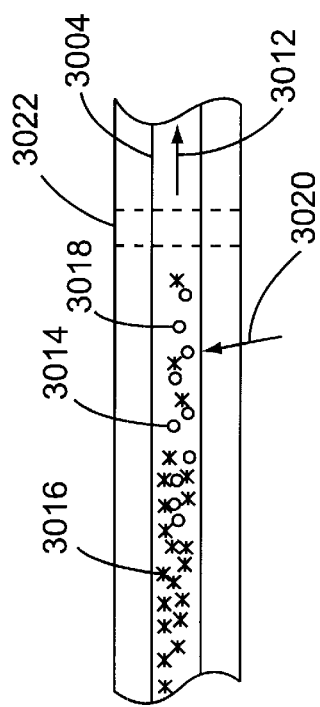
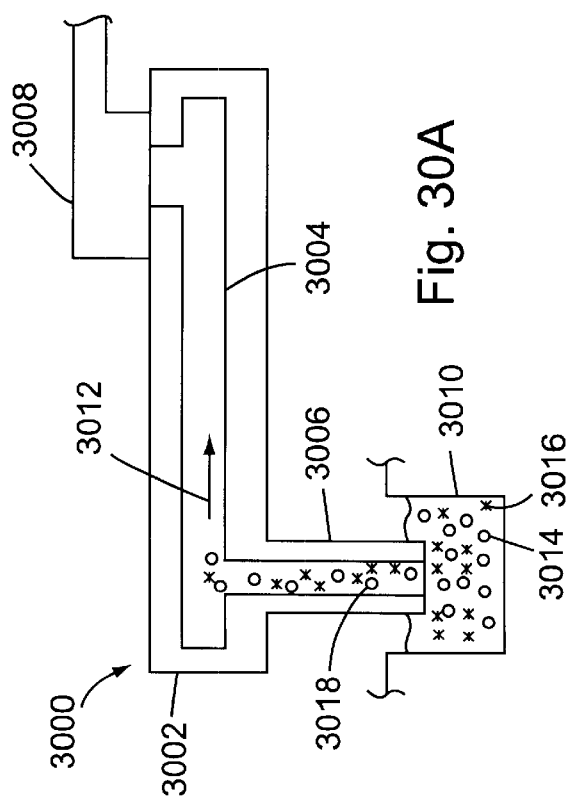
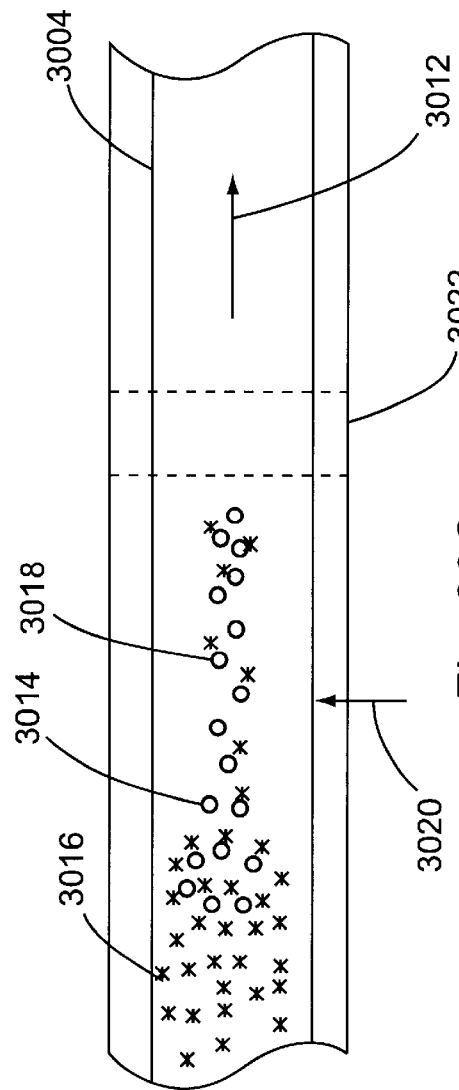

FOCUSING OF MICROPARTICLES IN MICROFLUIDIC SYSTEMS

CROSS REFERENCE TO RELATED APPLICATIONS

The subject application is a continuation-in-part of U.S. Ser. No. 09/569,747, entitled "Focusing of Microparticles in Microfluidic Systems," filed May 11, 2000 U.S. Pat. No. 6,506,609 which claim priority to and benefit of U.S. Ser. No. 60/134,472, entitiled "Focusing of Microparticles in Microfluidic Systems," filed May 17, 1999. The subject application is also related to PCT/US00/13294, entitiled "Focusing of Microparticles in Microfluidic Systems," filed May 11, 2000. The subject application claims priority to and benefit of each of these prior applications, each of which is incorporated by reference in their entirety.

COPYRIGHT NOTIFICATION

Pursuant to 37 C.F.R. §1.71(e),.Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

A variety of cell-based assays are of considerable commercial relevance in screening for modulators of cell-based activity. For example, compounds which affect cell death can have profound biological activities and are desirably screened for in cell-based assays. Cell death has become recognized as a physiological process important in normal development, hormonal regulation of various tissues, and, e.g., in regulation of the receptor repertoires of both T and B lymphocytes. The finding that a pattern of morphological changes is common to many examples of programmed cell death (or PCD) led to the suggestion of a common mechanism, and the term "apoptosis" was defined to include both the morphological features and the mechanism common to such programmed cell death (Kerr et al., *Br. J. Cancer* 26:239). This concept was extended by the finding that nuclear DNA fragmentation correlates well with apoptotic morphology (Arends et al., *Am. J. Pathol.* 136:593 (1990)), and the scientific literature contains many examples of PCD accompanied by these features. There are also clear examples of PCD in the absence of apoptotic morphology or DNA fragmentation (Clarke, *Anat. Embryl.* 181:195 (1990), Martin et al, *J. Cell Biol.* 106:829 (1988), and Ishigami et al., *J. Immunol.* 148:360 (1992)).

Cell-based assay systems model relevant biological phenomena, and have generally been widely adopted as screening assays, e.g., when screening for a compound's effect(s) on apoptosis or other biological phenomena. Pioneering technology providing cell- and other particle-based microscale assays are set forth in Parce et al. "High Throughput Screening Assay Systems in Microscale Fluidic Devices" WO 98/00231; in PCT/US00/04522, filed Feb. 22, 2000, entitled "Manipulation of Microparticles In Microfluidic Systems," by Mehta et al.; and in PCT/US00/04486, filed Feb. 22, 2000, entitled "Devices and Systems for Sequencing by Synthesis," by Mehta et al.

Other cell-based assays include various methods for the preparative or analytic sorting of different types of cells. For example, cell panning generally involves attaching an appropriate antibody or other cell-specific reagent to a solid support and then exposing the solid support to a heterogeneous cell sample. Cells possessing, e.g., the corresponding membrane-bound antigen will bind to the support, leaving those lacking the appropriate antigenic determinant to be washed away. Other well-known sorting methods include those using fluorescence-activated cell sorters ("FACSs"). FACSs for use in sorting cells and certain subcellular components such as molecules of DNA have been proposed in, e.g., Fu, A. Y. et al. (1999) "A Microfabricated Fluorescence-Activated Cell Sorter," *Nat. Biotechnol.* 17:1109–1111; Unger, M., et al. (1999) "Single Molecule Fluorescence Observed with Mercury Lamp Illumination," *Biotechniques* 27:1008–1013; and Chou, H. P. et al. (1999) "A Microfabricated Device for Sizing and Sorting DNA Molecules," *Proc. Nat'l. Acad. Sci.* 96:11–13. These sorting techniques utilizing generally involve focusing cells or other particles by flow channel geometry.

While cell-based assays are generally preferred in certain microscale screening applications, certain of these assays are difficult to adapt to conventional notions of high-throughput or ultra high-throughput screening assay systems. For example, one difficulty in flowing assay systems is that, during pressure-based flow of fluids in channels, non-uniform flow velocities are experienced. Faster fluid and material flow is observed in the center of a moving fluid stream than on the edge of a moving fluid stream. This non-uniform flow velocity reduces throughput for flowing assays, because assay runs have to be spaced well apart in the fluid stream to prevent overlap of materials moving at different velocities.

Accordingly, it would be advantageous to provide mechanisms for facilitating cell-based assays, including cell sorting techniques, especially in microscale systems. Additional microscale assays directed at subcellular-components, such as nucleic acids would also be desirable. The present invention provides these and other features which will become clear upon consideration of the following.

SUMMARY OF THE INVENTION

The present invention relates to methods of focusing particles in microchannels, e.g., to improve assay throughput and sensitivity, to sort particles, to count particles, or the like. In the methods of the invention, cells and other particles are focused in the center of, to one side of, or in other selected regions of microscale channels, thereby avoiding, e.g., the above noted difficulties inherent in pressure-based flow of particles. Furthermore, the device structures of the present invention are optionally integrated with other microfluidic systems. Other reactions or manipulations, including various binding assays, involving cells, other particles, or fluids upstream of the detection zone are also optionally performed, e.g., monitoring drug interactions with cells or other particles.

In one aspect, the invention provides methods of providing substantially uniform flow velocity to particles flowing in a first microchannel. In the methods, the particles are optionally flowed in the microchannel, e.g., using pressure-based flow, in which the particles flow with a substantially non-uniform flow velocity. Prior to performing the flowing step, the particles are optionally sampled with at least one capillary element, e.g., by dipping the capillary element into a well containing the particles on a microwell plate and drawing the particles into, e.g., reservoirs, microchannels, or other chambers of the device. The particles (e.g., a cell, a set of cells, a microbead, a set of microbeads, a functionalized microbead, a set of functionalized microbeads, a molecule, a set of molecules, etc.) are optionally focused horizontally and/or vertically in the first microchannel to provide substantially uniform flow velocity to the particles in the first microchannel. Particles are optionally focused using one or more fluid direction components (e.g., a fluid pressure force modulator, an electrokinetic force modulator, a capillary force modulator, a fluid wicking element, or the like). Additional options include sorting, detecting or otherwise manipulating the focused particles. Advantages of the invention include that the substantially uniform flow velocity increases a rate of particle mixing which reduces dispersion of the particles flowing in the first microchannel. For example, the particles are typically focused proximal to a center portion of the first microchannel, e.g., where focused fluid streamlines, that include the particles, flow at higher flow velocities than fluid streamlines flowing proximal to a surface of the first microchannel.

The particles are horizontally focused in the microchannel, e.g., by introducing a low density fluid and a high density fluid into the microchannel, causing the particles to be focused in an intermediate density fluid present between the high density fluid and the low density fluid. The particles are also optionally focused in a top or a bottom portion of the microchannel by introducing a high or a low density fluid into the microchannel with the flowing particles. The particles are vertically or horizontally focused in the microchannel, e.g., by simultaneously introducing fluid flow from two opposing microchannels into the first microchannel during flow of the particles in the first channel. Vertical focusing is also optionally achieved to one side of a microchannel by simultaneously introducing fluid flow from, e.g., a second microchannel into the first microchannel during flow of the particles in the first microchannel.

In another aspect, the particles include a plurality of first and second components in which the first components focus more than the second components such that at least some of the first components separate from the second components in the first microchannel. In preferred embodiments, substantially all of the first components separate from the second components in the first microchannel. In addition, the first components generally focus proximal to a center portion of the first microchannel more than the second components due to greater dispersion of the second components relative to the first components. The center portion of the first microchannel typically includes a higher velocity flow stream than other flow streams in the first microchannel, which effects the separation of first and second components.

Each first component optionally includes, e.g., a cell, a bead (e.g., a microbead, etc.), or the like, and typically further includes at least one antibody, at least one receptor, at least one nucleic acid, at least one enzyme, at least one antigen, at least one ligand, at least one adsorbent, or the like, attached thereto. Each second component optionally includes a ligand selected from, e.g., an antigen, a protein, a peptide, a nucleic acid, a lipid, a carbohydrate, an inorganic molecule, an organic molecule, a drug, a receptor ligand, an antibody, a neurotransmitter, a cytokine, a chemokine, a hormone, or the like. Furthermore, each second component typically further includes at least one label (e.g., a fluorescent label, etc.).

In preferred embodiments, the methods typically further include performing a binding assay in which prior to first and second component separation, at least one second component binds to at least one first component, which bound second component subsequently separates from unbound second components. Separation generally results because the bound second component typically has a greater velocity than bulk fluid in the first microchannel, which bulk fluid includes most of the unbound second components. The binding assays optionally include incubating the first and second components together to provide an incubation mixture prior to flowing the particles in the first microchannel. The methods generally also include introducing at least an aliquot of the incubation mixture into the first microchannel by drawing the aliquot from an external source (e.g., a well in a microwell plate or the like) through at least one capillary element that fluidly communicates with the first microchannel. Optionally, after introducing the aliquot of the incubation mixture, the method also includes introducing a selected volume of at least one buffer solution, inter alia, to further effect separation of components flowing in the first microchannel. In certain embodiments, the assays further include incubating a modulator with the first and second components, which modulator modulates the binding of the at least one second component to the at least one first component. For example, in some embodiments, the modulator inhibits the binding of the at least one second component to the at least one first component.

The binding assay generally includes detecting a detectable signal produced by at least the bound second component. For example, in many embodiments, baseline separation of the bound and unbound second components is achieved in less than about 25 seconds. Detecting the detectable signal produced by the separated, bound second component generally increases sensitivity of the binding assay relative to an assay that includes non-separated bound and unbound second components. The detectable signal is optionally selected from, e.g., a refractive index, a cellular activity, a light emission, a change in absorbance, a change in fluorescence, an absorbance, a fluorescence, a color shift, a fluorescence resonance energy transfer, a radioactive emission, a change in pH, a change in temperature, a time resolved fluorescence, a chemiluminescence, a bioluminescence, a change in mass, or the like. Optionally, prior to or after performing the binding assay, the method further includes the step of flowing the first components through the first microchannel to provide a negative control for detecting the detectable signals. As a further option, prior to or after performing the binding assay, the method further includes the step of flowing the second components through the first microchannel to provide a positive control for detecting the detectable signals. As another option, the method further includes quantifying an amount of the bound second component detected, which quantification provides a measure of a concentration of the second component in an incubation mixture that includes the first and second components.

In yet another aspect, the invention also provides particle washing or exchange techniques. For example, focused cells or other particles are optionally washed free of diffusible material by introducing a diluent into the first microchannel from at least a second channel and removing the resulting diluted diffused product comprising diluent mixed with the diffusible material through at least a third microchannel.

Alternating arrangements of diluent input and diffused product output channels are also optionally used to further wash the particles. For example, in one aspect the methods of the invention include simultaneously introducing the diluent into the first microchannel from the second microchannel and a fourth microchannel, where the second and fourth microchannel intersect the first microchannel at a common intersection region. Optionally, the methods include sequentially introducing the diluent into the first microchannel from the second microchannel and a fourth microchannel, wherein the second and fourth microchannels intersect the first microchannel at an offset intersection region. The diffused product is typically removed through the third microchannel and a fifth microchannel, which third and fifth microchannels intersect the first microchannel at a common intersection region. In further washing steps, the diluent is introduced through sixth and seventh microchannels which intersect the first microchannel at a common intersection. The resulting further diluted diffused product is removed through eighth and ninth microchannels, which intersect the first microchannel at a common intersection. Diluent is optionally introduced into the first microchannel by pressure or electrokinetic flow.

In one preferred assay of the invention, the particles are cells and the method includes performing a TUNEL assay or an Annexin-V assay on the cells in the channel to measure apoptosis.

Integrated systems for performing the above methods, including the particle sorting embodiments, are also provided.

An integrated system for providing substantially uniform flow velocity to flowing members of at least one particle population in a microfluidic device optionally includes a body structure that includes at least a first microchannel disposed therein. A cross section of the first microchannel typically includes, e.g., at least one dimension (e.g., a width, a height, or the like) between about 5 $\mu$m and about 25 $\mu$m or between about 10 $\mu$m and about 100 $\mu$m. A first fluid direction component (e.g., a fluid pressure force modulator) is typically coupled to the first microchannel for inducing flow of a fluidic material (e.g., a discrete sample volume or the like) that includes the members of the at least one particle population in the first microchannel. The first fluid direction component generally induces non-uniform flow. A source of at least one fluidic material is optionally fluidly coupled to the first microchannel. As an additional option, the source of the at least one fluidic material is fluidly coupled to the first microchannel by at least one capillary element, which capillary element fluidly communicates with the first microchannel. The system also optionally includes at least a second microchannel that intersects the first microchannel for introducing at least one fluid into the first microchannel to horizontally or vertically focus the members of the at least one particle population in the first microchannel. The at least one fluid is optionally introduced using a second fluid direction component that includes one or more of a fluid pressure force modulator, an electrokinetic force modulator, a capillary force modulator, a fluid wicking element, or the like. At least one flow control regulator for regulating flow of the fluidic material or the fluid in the first or second microchannel is also optionally provided. A computer including an instruction set directing simultaneous flow of the members of the at least one particle population in the first microchannel and simultaneous introduction of the at least one fluid from the second microchannel into the first microchannel is optionally also operably coupled to a fluid movement system for directing flow of materials in the microchannels. Typically, the substantially uniform flow velocity increases a rate of particle mixing which reduces dispersion of the members of the at least one particle population in the first microchannel. For example, the members are typically focused proximal to a center portion of the first microchannel, e.g., where focused fluid streamlines, that include the members, flow at higher flow velocities than fluid streamlines flowing proximal to a surface of the first microchannel.

As a further option, this integrated system additionally includes at least a third microchannel which intersects the first microchannel in an intersection region common to the second microchannel. The flow control regulator of this system optionally further regulates flow of the at least one fluid in the second and the third microchannels. In this embodiment, the computer typically also includes an instruction set for simultaneously flowing fluids from the second and third microchannels into the first microchannel.

In particle washing systems, typically, at least fourth and fifth channels which intersect the first microchannel at a common intersection downstream of the second and third microchannels are provided. The computer further includes an instruction set for simultaneously flowing material from the first microchannel into the fourth and fifth microchannels. Sixth and seventh microchannels which intersect the first microchannel at a common intersection downstream of the fourth and fifth microchannels, with the computer further comprising an instruction set for simultaneously flowing material from the sixth and seventh microchannels into the first microchannel are optionally provided. Similarly, eighth and ninth microchannels which intersect the first microchannel at a common intersection downstream of the sixth and seventh microchannels, the computer further including an instruction set for simultaneously flowing material from the first microchannel into the eighth and ninth microchannels are optionally provided.

The integrated system optionally includes sources for any reagent or particle used in the methods noted above, such as one or more sources of terminal deoxynucleotide transferase, one or more sources of one or more fluorescein labeled nucleotides or other labeled polynucleotides, one or more sources of Annexin V, one or more sources of an Annexin V-biotin conjugate, one or more sources of a DNA dye, one or more sources of Campthotecin, one or more sources of Calcein-AM, one or more sources of a control cell, one or more sources of a test cell, etc.

Signal detector(s) mounted proximal to the first microchannel for detecting a detectable signal produced by one or more of the members of the at least one particle population in the microchannel are typically provided in the integrated systems of the invention. The detector also optionally includes, e.g., a fluorescent excitation source and a fluorescent emission detection element. Optionally, the computer is operably linked to the signal detector and has an instruction set for converting detected signal information into digital data.

In certain embodiments of the invention, the system provides substantially uniform flow velocity to members of at least a first of two particle populations. The members of the first particle population typically flow with a greater velocity than bulk fluid in the first microchannel, which bulk fluid generally includes most unbound members of a second particle population. As a result, at least some of the members of the first particle population typically separate from the unbound members of the second particle population. For example, the members of the first particle population typically focus proximal to a center portion of the first microchannel more than the members of the second particle population due to greater dispersion of the members of the second particle population relative to the members of the first particle population in the first microchannel. In particular, the center portion of the first microchannel generally includes a higher velocity flow stream than other flow streams in the first microchannel.

In preferred embodiments, the system is used to perform various binding assays. For example, prior to providing substantially uniform flow velocity, at least one member of the second particle population binds to at least one member of the first particle population, which bound member subsequently separates from the unbound members of the second particle population. Optionally, the members of the first and second particle populations are incubated together to provide an incubation mixture prior to providing the substantially uniform flow velocity. Each member of the first particle population typically includes, e.g., a cell, a bead (e.g., a microbead, etc.) or the like. In addition, each member of the first particle population generally further includes at least one antibody, at least one receptor, at least one nucleic acid, at least one enzyme, at least one antigen, at least one ligand, at least one adsorbent, or the like, attached thereto. Each member of the second particle population optionally includes a ligand selected from, e.g., an antigen, a protein, a peptide, a nucleic acid, a lipid, a carbohydrate, an inorganic molecule, an organic molecule, a drug, a receptor ligand, an antibody, a neurotransmitter, a cytokine, a chemokine, a hormone, or the like. Typically, each member of the second particle population further includes at least one label (e.g., fluorescent label or the like). In these embodiments, the systems typically further includes at least one signal detector mounted proximal to the first microchannel for detecting a detectable signal produced by at least the bound members of the second particle population. For example, the detectable signal is typically selected from, e.g., a refractive index, a cellular activity, a light emission, a change in absorbance, a change in fluorescence, an absorbance, a fluorescence, a color shift, a fluorescence resonance energy transfer, a radioactive emission, a change in pH, a change in temperature, a time resolved fluorescence, a chemiluminescence, a bioluminescence, a change in mass, or the like.

The integrated system of the present invention is also optionally used to sort the members of a particle population (e.g., a cell, a set of cells, a microbead, a set of microbeads, a functionalized microbead, a set of functionalized microbeads, a molecule, a set of molecules, or the like). In this embodiment, the integrated system typically additionally includes a third and a fourth microchannel which intersect the first microchannel downstream from the intersection of the second microchannel with the first microchannel. The fourth microchannel also generally intersects the first microchannel downstream from the intersection of the third microchannel with the first microchannel. The flow control regulator of this system optionally further regulates flow of the at least one fluid in the third or the fourth microchannels. Furthermore, the signal detector typically detects a detectable signal produced by a selected member of the particle population between the intersections of the second and the third microchannels with the first microchannel.

In this particle sorting embodiment, the computer is optionally operably linked to the first or other fluid direction component(s), the flow control regulator, and the signal detector. Additionally, the instruction set typically directs simultaneous introduction of the at least one fluid from the third microchannel into the first microchannel to horizontally or vertically focus the selected member of the particle population such that the selected member is directed into the fourth microchannel in response to the detectable signal produced by the selected member. Optionally, the instruction set further directs simultaneous introduction of the at least one fluid from the third microchannel by activating a heating element (e.g., a Joule heating electrode, a conductively coated microchannel portion, etc.) disposed within the third microchannel or a well that fluidly communicates with the third microchannel.

In another embodiment, at least a portion of the first microchannel optionally includes a separation element disposed therein. The separation element optionally includes, e.g., two sides and at least a portion of the separation element is typically disposed upstream of the fourth microchannel. In this embodiment, a selected member of the particle population is generally directed to one of the two sides of the separation element and into the fourth microchannel that intersects the first microchannel in response to the detectable signal produced by the selected member.

The integrated system for use in particle sorting also optionally includes a fifth microchannel which intersects the first microchannel in an intersection region common to the second microchannel. In this case, the flow control regulator also typically regulates flow of the at least one fluid in the second and the fifth microchannels, and the computer optionally includes an instruction set for simultaneously flowing fluids from the second and the fifth microchannels into the first microchannel. Similarly, the system also optionally includes a sixth microchannel which intersects the first microchannel in an intersection region common to the third microchannel. In this embodiment, the flow control regulator optionally additionally regulates flow of the at least one fluid in the third and the sixth microchannels. Furthermore, the computer also typically includes an instruction set for flowing fluids from the third and the sixth microchannels into the first microchannel. Optionally, the instruction set directs individual or simultaneous fluid flow from the third and sixth microchannels by individually or simultaneously activating at least one heating element (e.g., a Joule heating electrode, a conductively coated microchannel portion, or the like) disposed within each of the third and sixth microchannels or within at least one well that fluidly communicates with each of the third and sixth microchannels.

Many additional aspects of the invention will be apparent upon review, including uses of the devices and systems of the invention, methods of manufacture of the devices and systems of the invention, kits for practicing the methods of the invention and the like. For example, kits comprising any of the devices or systems set forth above, or elements thereof, in conjunction with packaging materials (e.g., containers, sealable plastic bags, etc.) and instructions for using the devices, e.g., to practice the methods herein, are also contemplated.

BRIEF DESCRIPTION OF THE FIGURES

FIG. 30A schematically depicts the introduction of an aliquot of an incubation mixture into a device through a capillary element in one embodiment of a binding assay of the invention.

FIGS. 30B–C schematically illustrate the separation of certain particles of an incubation mixture from the bulk fluid in a microchannel of a device from various viewpoints in one embodiment of a binding assay of the invention.

DETAILED DISCUSSION OF THE INVENTION

Figure 1A:
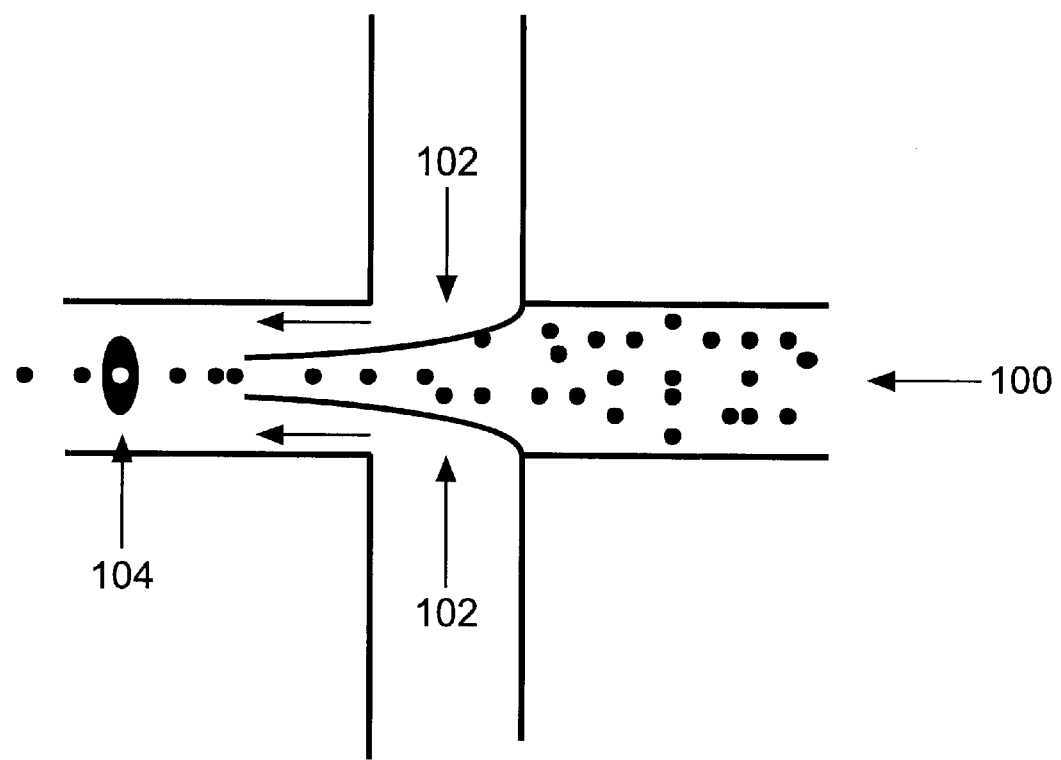
FIG. 1A is a schematic showing focusing of cells in a microscale system by simultaneous flow from side channels into a main channel through which the cells are being flowed.

The invention relates to particle focusing to improve assay throughput by regularizing flow velocity. As used herein, the term "particle" refers to a discretely describable material element, such as a cell, microbead (e.g., functionalized or non-functionalized), molecule (e.g., a nucleic acid, a polypeptide, etc.), or the like. For example, a particle typically includes, e.g., a soluble or non-soluble component of a fluid mixture, such as a solubilized or suspended molecule, liposome, cell, organelle, bead, or the like. Ordinarily, the particle is a detectable unit; for example, in the case of molecular particles, the particle is detectable, e.g., via a label. Similarly, microbeads and cells are detected, e.g., optically or through an associated label (this detection is also optionally, e.g., optical or via fluorescence).

The following provides details regarding various aspects of the methods of focusing particles, e.g., vertically and/or horizontally within the microscale systems of the invention. It also provides details pertaining to methods of washing cells and to particular assays, such as cell viability screening, which are optionally performed using the methods and devices of the present invention. Devices and integrated systems are also discussed extensively.

LAMINAR FLOW VERTICAL FOCUSING OF CELLS AND OTHER PARTICLES IN MICROSCALE SYSTEMS

Microfluidic hydrodynamic focusing is a highly effective technique when used, e.g., in flow cytometry applications, such as the assessment of live/dead cell ratios, the analysis of transfection efficiencies, the sizing of various molecular components (e.g., polynucleotides, polypeptides, etc.), the study of apoptosis, or the like. Fluid flow streams are optionally "pinched" or "focused" into a narrow region of a microchannel to facilitate single particle or narrow streamline detection using a variety of optical detection schemes (discussed further, below). In one embodiment, particle focusing is achieved electrodynamically (see also, Ramsey et al., "Apparatus and Method for Performing Electrodynamic Focusing on a Microchip," U.S. Pat. No. 5,858,187, issued Jan. 12, 1999). In other preferred embodiments, pressure, Joule heating, and/or other fluid movement methods are used to focus cells or other particles.

As used herein, a "vertically" focused particle stream refers to a particle stream that is substantially focused, pinched, narrowed, or otherwise confined along or proximal to a plane that extends, in one dimension, from the highest to the lowest internal surface of a microchannel (e.g., along the length of a cross-sectional line or axis of the microchannel), and along a selected length of the microchannel, in another dimension, when the microfluidic device is oriented for typical operational usage. A vertically focused particle stream corresponds to a plane that is oriented approximately, 90° from a plane in which a horizontally focused particle stream (discussed below) would be oriented.

Vertical focusing is optionally achieved by flowing fluids into a microchannel (e.g., from one or more sides of the microchannel) in which a particle stream is flowing to focus the particles along or proximal to the vertical plane having a dimension that corresponds to a selected vertical line or axis of the microchannel. The level of focusing along or proximal to the vertical plane is optionally varied. Furthermore, as indicated, a particle stream is also optionally vertically focused away from the vertical cross-sectional axis, e.g., to one side of a microchannel. An additional option includes simultaneously horizontally and vertically focusing a particle stream to position the stream within a desired region of a microchannel. As described further below, focusing is optionally used to control the dispersion of, e.g., discrete sample volumes flowing in a microchannel.

For example, the measurement of fluorescent signals associated with single cells (or other particles) in microfluidic channels is difficult if the cells or particles are randomly disbursed in the channels. The channels are usually about 100 $\mu$m or larger in width to prevent clogging by particle aggregates; however, particles such as cells are typically on the order of 10 $\mu$m in diameter. An interrogating light beam is focused on a spot usually much less than the 100 $\mu$m width of the channel. As a result, it is useful, e.g., to center particles in the channel, to position particles to one side of a channel, or to otherwise focus flowing particles in a portion of a channel prior to detection to obtain accurate fluorescent readings on all the particles passing through the channel.

Figure 1B:
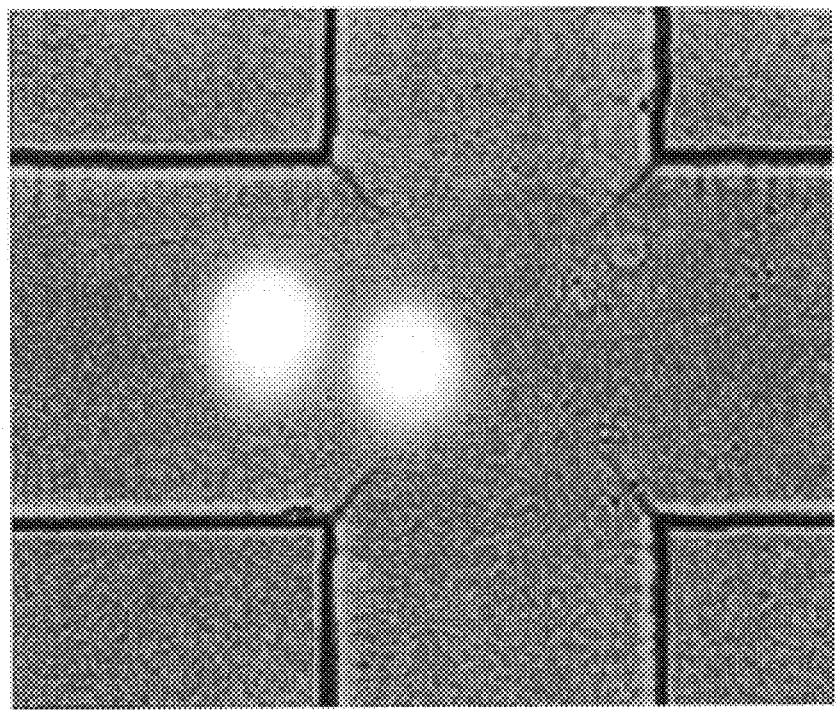
FIG. 1B is a photomicrograph of focused labeled cells flowing in a microchannel.

FIG. 1A shows an example cell (or other particle) analysis chip design for on-chip focusing. The microchannel network geometry includes a cross formed by four microchannels that intersect in a common intersection region (e.g., a symmetric microchannel intersection). FIG. 1B shows a photomicrograph of this microchannel configuration with focused labeled cells flowing in a main or analysis microchannel. Cells or other particles are optionally flowed in the main microchannel and/or focused using various methods, which include the use of electrokinetic forces, pressure gradients, surface tension gradients, gravitational forces, or the like. Furthermore, combinations of these fluid flow/focusing methods are also optionally used. A preferred method of flowing particles in the main microchannel utilizes pressure-based flow.

In the embodiment depicted in FIG. 1, cells 100 (or other particles) are typically flowed from one microchannel into the cross-junction and focused by introducing hydrodynamic flows 102 from the two orthogonal microchannels. Non-orthogonal (e.g., opposing or non-opposing) microchannels are also optionally used. For example, as discussed herein, particles are optionally focused with a single focusing microchannel, or alternately, by using a series of offset focusing microchannels to achieve focusing by serial introduction of fluids from the offset channels. As depicted in both panels of FIG. 1, cells 100 are optionally constrained to the center of a detection microchannel downstream from the two orthogonal microchannels by hydrodynamic flows 102 introduced from both sides as cells 100 pass through detector 104. Using these methods, an experiment is optionally conducted which uses, e.g., a small optical detection system on the order of the size of the particular cell or other particle being analyzed to derive accurate and precise measurements.

Figure 21:
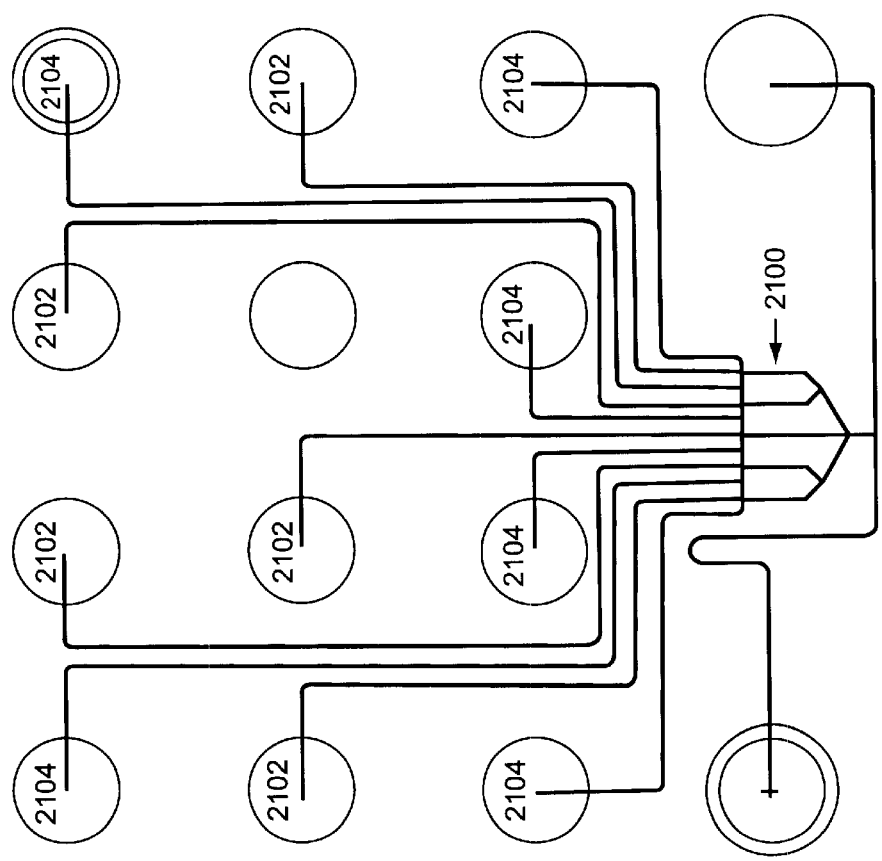
FIG. 21 is a microchannel network that is optionally utilized to hydrodynamically focus particles.

FIG. 21 depicts a microchannel network that is optionally used to hydrodynamically focus particles, e.g., cells, microbeads, molecules, or the like in parallel through common detection zone 2100. For example, five cell suspensions are typically loaded into wells 2102 and flowed towards common detection zone 2100. Cell buffer solutions are also typically loaded into particular wells (e.g., well 2104) in the device and flowed towards common detection zone 2100. As shown, in the region just prior to common detection zone 2100, each microchannel in which cells are flowed intersects with two buffer flowing microchannels in a cross-configuration to focus the cells as they pass through common detection zone 2100.

In another embodiment of these methods, a "T-junction" microchannel geometry (e.g., an asymmetric microchannel intersection) is optionally used to focus cells or other particles 1600 to one side of detection microchannel 1604.

Figure 16:
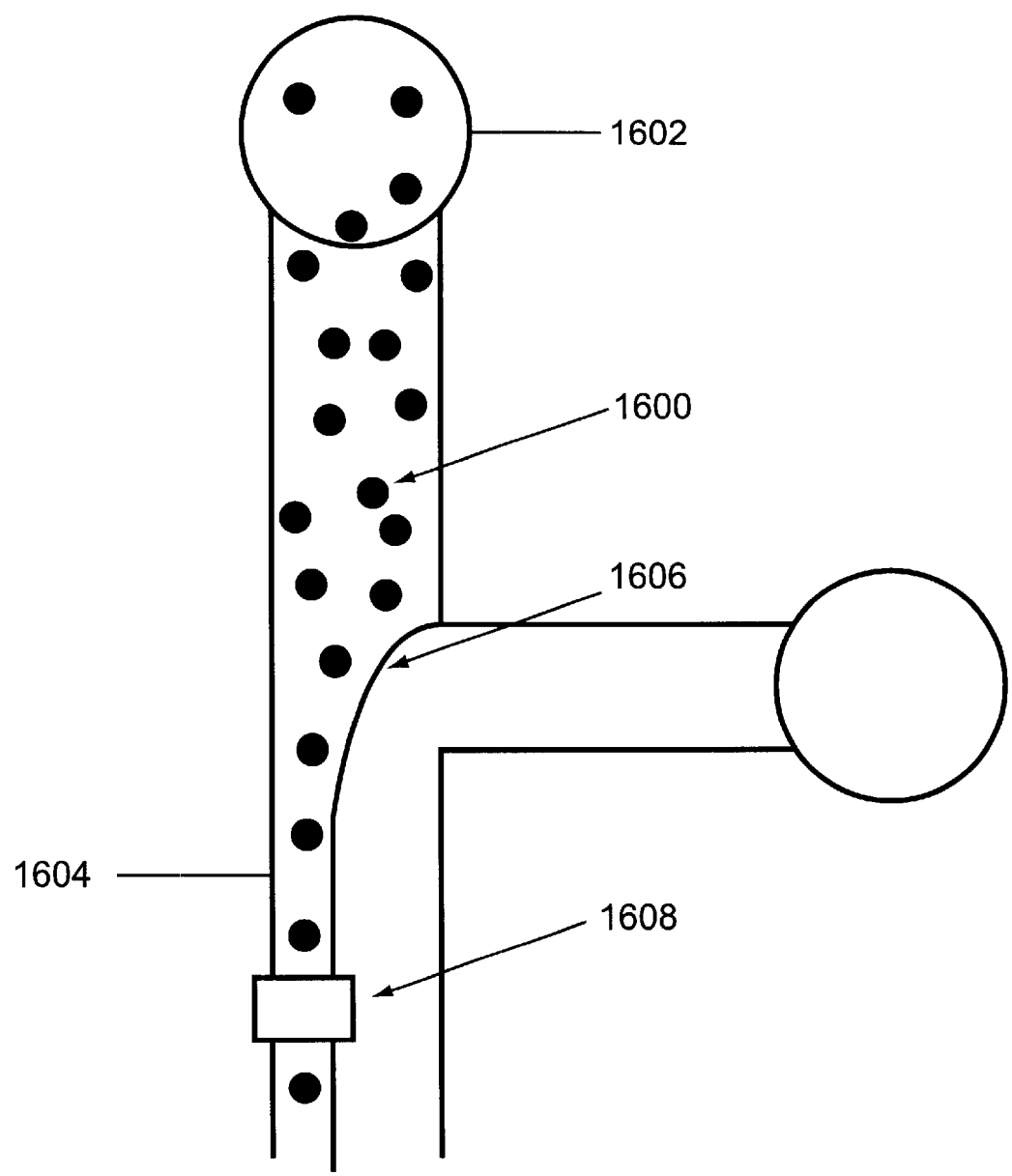
FIG. 16 shows a "T-junction" microchannel configuration for hydrodynamically focusing cells for use in, e.g., flow cytometry.

(FIG. 16). As shown in FIG. 16, a "T-junction" typically includes an orthogonal intersection of two microchannels. However, microchannel geometries that include non-orthogonal intersections are also optionally used (e.g., a "Y-junction" or the like). In this embodiment, cells or other particles 1600 are typically flowed from one well 1602 and pinched to one side of detection microchannel 1604 by only one other introduced fluid stream 1606 and the wall of detection microchannel 1604 opposing the "T-junction" as cells or other particles 1600 pass through detector 1608. This embodiment generally achieves the same effect as the cross-microchannel formats, but with the added advantage of using less space on the microfluidic device due to the use of one focusing channel, rather than two which, in turn, provides for greater parallelism or complexity in chip design, and for more control of the hydrodynamic focusing mechanism.

The focusing of flow to one side of a microchannel also provides a solution to various problems associated with controlling fluid flow under lower pressures (e.g., difficulties regulating fluid direction pumps, etc.). For example, the resistance produced by pinching fluid materials against microchannel walls functions to reduce the velocity of the pinched fluid stream. As a result, pinched fluids are optionally flowed under higher pressures, e.g., for greater control, while achieving comparable low pressure flow velocities. Resistance is also altered, e.g., by varying the viscosity of pinched fluid materials, which provides an added level of control over flow rates and the extent of fluid pinching.

FOCUSING CELLS HORIZONTALLY IN A MICROCHANNEL

In high throughput screening applications using cells or microparticles, the throughput is increased if all of the cells or microparticles move at a common velocity. The parabolic nature of pressure-based flow causes cells at the center of a flow stream to move faster than those near the walls of a channel. This phenomenon causes dispersion in the system since cells can move from one sample into another. Controlling dispersion, e.g., to enhance throughput according to the methods of the invention is described further below. To focus cells in the center of a channel, high and low density fluid streams are incorporated into fluid flow of the cells or particles. The high density fluid keeps the cells or other microparticles off of the bottom of the channel, while the low density fluid keeps cells or microparticles off of the top of the microchannel, thereby focusing the cells in the center of the fluid stream. Even after diffusion brings the high, low, and middle density fluids into equilibrium, the cells generally remain focused in the center of a microchannel. Optionally, the point in the microchannel in which the high and low density fluids are flowed into the main channel is deeper than other channel regions to improve distribution of the different density fluids.

A "horizontally" focused particle stream, as used herein, refers to a particle stream that is substantially focused, pinched, narrowed, or otherwise confined along or proximal to a plane that extends, in one dimension, from one substantially vertical internal microchannel surface to another (e.g., substantially parallel to the dimension of the lowest internal microchannel surface that extends from one vertical internal surface to another), and along a selected length of the microchannel, in another dimension, when the microfluidic device is oriented for typical operational usage. A horizontally focused particle stream corresponds to a plane that is oriented approximately 90° from a plane in which a vertically focused particle stream (discussed above) would be oriented.

As mentioned, horizontal particle focusing typically involves using focusing fluids having densities that differ relative to the density of a particle stream. For example, higher density fluids are optionally used to substantially prevent the particle stream from contacting the lowest internal surface of the microchannel over a particular length. In contrast, a less dense focusing fluid is optionally used to substantially prevent the particle stream from contacting the highest internal surface of the microchannel over a selected length. Additionally, both lower and higher density focusing fluids are optionally flowed simultaneously to substantially prevent the particle stream from contacting either the highest or lowest internal microchannel surfaces. The extent of horizontal focusing achieved is optionally regulated, e.g., by varying the density and/or the volume of focusing fluid flowed into a microchannel. A further option includes simultaneously horizontally and vertically focusing a particle stream to position the stream within a desired region of a microchannel.

Figure 2A:
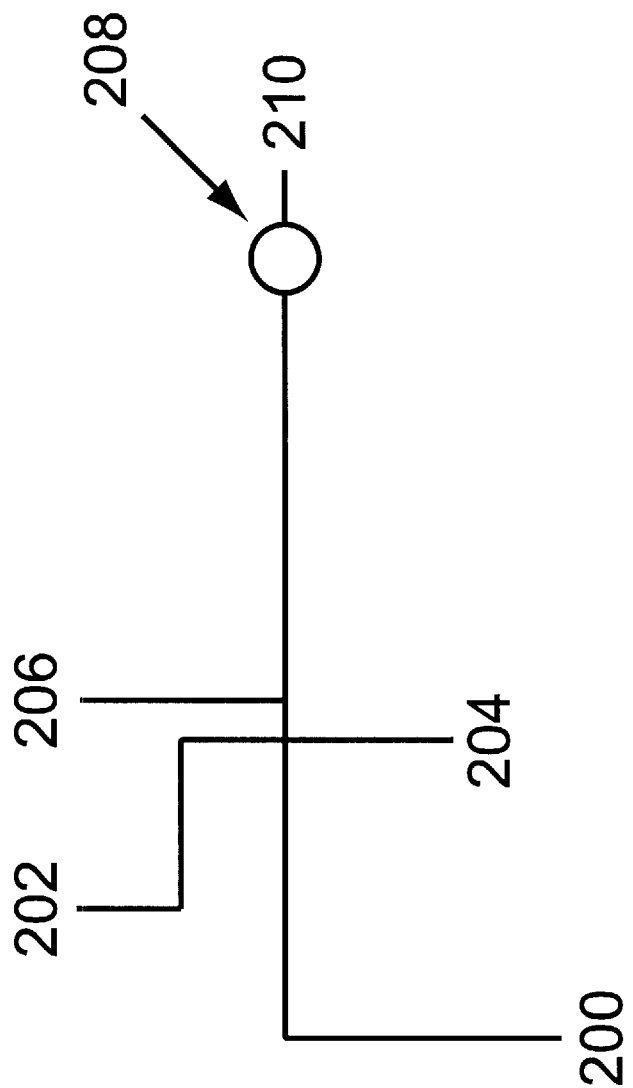
FIG. 2A is a schematic of a microfluidic system with a pressure-source (in this case a vacuum source) for achieving fluid movement.
Figure 2B:
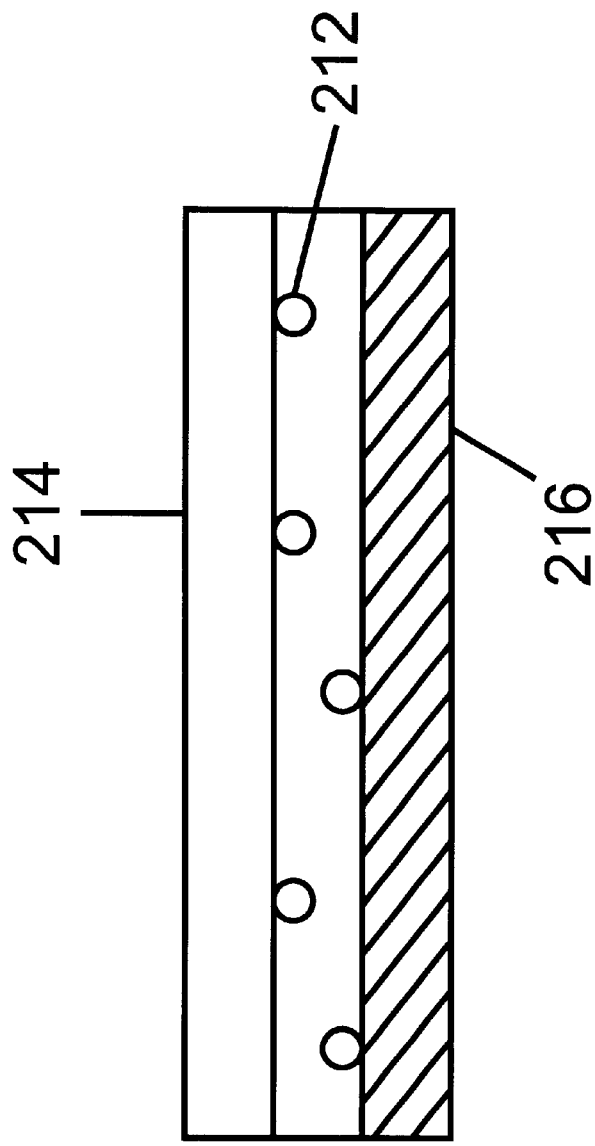
FIG. 2B shows a cross-sectional view down a channel-having high, medium and low fluid density.

FIG. 2A is a schematic representation of a microfluidic system that uses vacuum source 210 to achieve fluid movement. In this embodiment, test compounds are typically flowed through capillary channel 200 (capillary channels or elements are discussed in greater detail, below) into a detection microchannel of the device. High density buffer and low density buffer are optionally flowed into the detection microchannel through high density buffer microchannel 202 and low density buffer microchannel 204, respectively, both of which intersect the detection microchannel upstream from detector 208. Cell microchannel 206 typically intersects the detection microchannel downstream from the intersections of high density buffer microchannel 202 and low density buffer microchannel 204, but upstream from detector 208. Cells in medium density buffer are typically flowed into the detection channel from cell microchannel 206, becoming focused between the high and low density buffers, and exposed to the test compounds prior to flowing through detector 208. FIG. 2B shows a cross-sectional view down the detection microchannel which includes low density buffer 214, cells 212, and high density buffer 216.

Fluid density-based focusing also optionally entails focusing cells or other particles either at the top or the bottom of a microchannel. For example, a high density fluid is optionally flowed into a microchannel to keep cells or other particles off of the bottom of the microchannel, i.e., focused at the top of the microchannel. Alternatively, a low density fluid is flowed into a microchannel to keep cells or other particles off of the top of the microchannel, i.e., focused on the bottom of the microchannel.

It is also worth noting that horizontal and vertical focusing are optionally both performed to center cells vertically and horizontally in the center of microscale channels. Furthermore, the extent of hydrodynamic focusing, using either or both methods, is typically controlled by a variety of variables including viscosity in pressure driven flows, electrokinetic mobility in electrokinetic flow, fluid density in gravity driven flow, or the like. As will be recognized by those of skill, the enhanced control of focusing, provided by the present invention, allows for a large gamut of flow-based applications, including any particle and/or bulk fluid application that involves small, uniform detection regions.

DISPERSION CONTROL

Throughput is the rate at which work is performed in a given system. Improvements to the capabilities of analytical instrumentation, such a microfluidic devices, are often made by enhancing device throughput. One way to elevate the throughput of various microfluidic applications is to increase the number of discrete sample volumes or "slugs" of material accommodated per unit length of a given microchannel or other microscale device cavity. A limiting factor such as slug dispersion restricts minimum slug-to-slug spacing in addition to time averaged sample concentrations. As a result, microfluidic devices in which slug dispersion is inhibited in a controllable manner would further improve the throughput and performance of selected microfluidic analytical and preparative processes.

As used herein, the term "dispersion" refers to the convection-induced, longitudinal dispersion of material within a fluid medium due to velocity variations across streamlines, e.g., in pressure driven flow systems, electrokinetically driven flow systems around curves and corners, and electrokinetically driven flow systems having non-uniform buffer ionic concentrations, e.g., plugs of high and low salt solutions within the same channel system. For the purposes of the channel systems of the present invention, dispersion is generally defined as that due to the coupling between flow and molecular diffusion, i.e., Taylor dispersion. In this regime, the time-scale for dispersion due to convective transport is long or comparable to the time scale for molecular diffusion in the direction orthogonal to the flow direction. For discussions on dispersion and Taylor dispersion in particular, see, e.g., Taylor, *Proc. Roy. Soc. London* (1953) 219A:186–203, Aris, *Proc. Roy. Soc. London* (1956) A235:67–77, Chatwin et al., *J. Fluid Mech.* (1982) 120:347–358, Doshi et al., *Chem. Eng. Sci.* (1978) 33:795–804, and Gnell et al., *Chem. Eng. Comm.* (1987) 58:231–244, each of which is incorporated herein by reference.

For applications (e.g., assays, screens, or the like) performed in the devices described herein, e.g., involving multiple discrete sample volumes or slugs, where high throughput is desired, the methods of the invention optionally include introducing and focusing such sample slugs in or proximal to the center of a microscale cavity (e.g., at or near a dilution or mixing intersection of microchannels or other device cavities), e.g., under pressure-based flow prior to detection. Due to the parabolic nature of pressure-based flow, sample introduction at or near the center of a particular microchannel, where the flow rate is highest, typically increases the rate of sample mixing which, in turn, reduces sample dispersion, e.g., in those fluid streamlines proximal to the center of the microchannel. In contrast, when samples are introduced at or near a cavity wall, where pressure-based flow is slowest, sample dispersion is generally increased relative to samples focused proximal to the center of the cavity. As indicated, increased slug dispersion decreases assay throughput by limiting minimum slug-to-slug spacing.

Discrete sample volumes (e.g., where the solvent is dimethyl sulfoxide (DMSO) or the like) are optionally introduced in or proximal to cavity centers by vertically and/or horizontally focusing the sample volumes according to the methods described herein. In these embodiments, symmetric focusing microchannel configurations (see, e.g., those schematically depicted in FIGS. 1 and 29) are generally used rather than asymmetric focusing microchannel configurations (see, e.g., those schematically shown in FIGS. 16 and 28) to effect sample focusing at or near cavity centers. An example providing flow simulations that illustrate variations of sample concentrations with time for discrete sample volumes flowed alternatively through asymmetric or symmetric microchannel intersections is described below.

METHODS OF PERFORMING HIGH SENSITIVITY ASSAYS

Background noise caused by, e.g., non-analytes generally limits assay sensitivity and detection limits. As used herein, "assay sensitivity" refers to the ability of an assay to discriminate between small differences in analyte concentration, whereas "assay detection limit" refers to the minimum amount of unlabeled analyte that can be labeled and detected. For example, the presence of excessive amounts of unbound label may prevent a particular analyte from being distinguished at the point of detection in an assay. One way to reduce the background signal attributable to such unbound label and, in turn, improve the sensitivity and detection limit of a given assay, is to separate analytes from such non-analytes prior to detection. In certain aspects, the present invention utilizes particle dispersion (described above) in different flow streams within microscale cavities to effect separation of fluidic material components prior to assay detection. In particular, particles such as cells, beads, or the like tend to flow with higher velocities than bulk fluid, due, at least in part, to a particle dispersion property that causes them to flow in higher velocity fluid streams near the middle of a channel more frequently than slower fluid streams near the edges of a channel, e.g., in the absence of an introduced external focusing stream, such as from an intersecting side channel. In contrast, smaller fluid components, such as unbound labeling compounds, tend to disperse more in the bulk fluid than cells, beads, and other larger components, such that over time, labels bound to these larger components will separate from unbound label flowing in a microscale cavity of a device of the invention. The present invention exploits these phenomena to improve various microfluidic applications, including the sensitivity and detection limit of various binding assays.

To illustrate, a binding assay performed according to the methods of the present invention optionally includes incubating first and second components together to provide an incubation mixture prior to flowing the particles in a microchannel of a device. First components typically include, e.g., cells, beads, or other components, whereas second components generally include a ligand (e.g., a labeled ligand, etc.) to be assayed or screened. Suitable labels (e.g., fluorescent labels or the like) are described herein and are otherwise generally known in the art. First components typically further include antibodies, receptors, nucleic acids, enzymes, antigens, adsorbents (e.g., hydrophilic or hydrophobic interaction adsorbents, etc.), or the like attached thereto (e.g., covalently or otherwise attached to an external surface), which, e.g., function as binding partners for the second components. In other embodiments, first components do not have antibodies, receptors, or other binding partners attached to or otherwise associated with external surfaces. In these embodiments, ligands may associate directly with first components, e.g., via various non-covalent interactions. For example, if a second component (e.g., a microbead) is fabricated from a hydrophobic material, a hydrophobic ligand may associate directly with the surface of the second component in a binding assay. Second components optionally include essentially any ligand to be assayed or screened. Exemplary ligands utilized in the assays of the invention include, e.g., an antigen, a protein, a peptide, a nucleic acid, a lipid, a carbohydrate, an inorganic molecule, an organic molecule, a drug, a receptor ligand, an antibody, a neurotransmitter, a cytokine, a chemokine, a hormone, or the like.

In certain embodiments, the methods include introducing aliquots of an incubation mixture into a microfluidic device by drawing the aliquots from an external source (e.g., a well of a microwell plate or the like) through a capillary element that fluidly communicates with a microscale cavity (e.g., a microchannel or the like) in the device. One embodiment of this method of introducing incubation mixture aliquots into microfluidic devices is depicted in FIG. 30A. As shown, microfluidic device 3000 includes body structure 3002, which includes microchannel 3004. Capillary element 3006 fluidly communicates with microchannel 3004. Under negative pressure supplied by, e.g., pressure force modulator 3008 (e.g., a vacuum source or the like), an aliquot of an incubation mixture is drawn from external source 3010 (e.g., a well in a microwell plate, etc.) through capillary element 3006 and into microchannel 3004. The direction of fluid flow is indicated by arrow 3012. As further shown, the incubation mixture in external source 3010 includes first components 3014 (e.g., cells, beads, etc.) and second components 3016 (e.g., labeled ligands to be assayed). FIG. 30A further schematically depicts binding complexes 3018 that include first and second components bound together. Optionally, after introducing the aliquot of the incubation mixture, the methods further include introducing selected volumes of another fluidic material, such as a buffer solution. Although not shown, in certain embodiments of the invention, the assays further include incubating modulators (e.g., an inhibitor, an agonist, an antagonist, or the like) with the first and second components, which modulators modulate the binding of first and second components.

FIGS. 30B–C schematically illustrate the separation of components of the incubation mixture from the bulk fluid in a portion of microchannel 3004 of microfluidic device 3000 from various viewpoints prior to detection. In particular, FIG. 30B schematically provides a side view of a portion of microchannel 3004. As shown, following introduction into microchannel 3004, first components 3014 and binding complexes 3018 flow faster than the bulk fluid which includes unbound second components 3016, such that at some point 3020 prior to detection region 3022 baseline separation between first components 3014/binding complexes 3018 and unbound second components 3016 is achieved. FIG. 30C provides a top view of the same portion of microchannel 3004 depicted in FIG. 30B. As shown, first components 3014 and binding complexes 3018 flow faster than bulk fluid in microchannel 3004, because those components generally focus proximal to a center portion of microchannel 3004 more than unbound second components 3016 due to greater dispersion of second components 3016 relative to first components 3014/binding complexes 3018. As described above, the center portion of microchannel 3004 typically includes a higher velocity flow stream than other flow streams in microchannel 3004, e.g., due to the parabolic nature of, e.g., pressure-based fluid flow. Parabolic flow profiles are schematically depicted in, e.g., FIGS. 28 and 29. As a result, first components 3014/binding complexes 3018 typically achieve baseline separation from unbound second components 3016 at some point 3020 prior to detection region 3022. The direction of fluid flow in microchannel 3004 is indicated by arrow 3012.

Baseline separation of first components 3014/binding complexes 3018 from unbound second components 3016 prior to assay detection generally significantly improves assay sensitivity and detection limits. In many embodiments, baseline separation of the bound and unbound second components is achieved in less than about 25 seconds. Many different detectable signals are optionally utilized in performing the assays described herein. Certain of these include, e.g., a refractive index, a cellular activity, a light emission, a change in absorbance, a change in fluorescence, an absorbance, a fluorescence, a color shift, a fluorescence resonance energy transfer, a radioactive emission, a change in pH, a change in temperature, a time resolved fluorescence, a chemiluminescence, a bioluminescence, a change in mass, or the like.

Optionally, prior to or after performing a binding assay, the methods further include the step of flowing the first components through the first microchannel to provide a negative control for detecting the detectable signals. As an additional option, prior to or after performing a binding assay, the methods further include the step of flowing the second components through the first microchannel to provide a positive control for detecting the detectable signals. As yet another option, the methods further include quantifying an amount of the bound second component detected, which quantification provides a measure of a concentration of the second component in an incubation mixture that includes the first and second components. Examples that further illustrate these assay methods are provided below. In addition, various exemplary analyses, such as transport assays, binding assays (e.g., cell rolling assays, expression assays, etc.), screening assays, or the like that are optionally performed according to these methods are described throughout this disclosure.

USE OF FOCUSING TO SORT PARTICLES

The separation of fluorochrome-labeled cells with fluorescence-activated cell sorters is well-known in the art, as mentioned above. In brief, the technique generally involves incubating a mixed population cells with a fluorescently-labeled antibody against a specific antigenic determinant displayed on the surfaces of target cells. The suspension of cells is then typically expelled, one cell at a time, from a sample chamber of the device through a small vibrating nozzle that generates microdroplets. Each microdroplet contains a single cell that the FACS assays for the presence or absence of the fluorochrome label using a laser source and a detector. Droplets that fluoresce are electrically charged in proportion to their fluorescence and in turn separated as they pass between charged plates. General references describing FACS include, e.g., Kuby, *Immunology* ($3^{rd}$ Ed.) W.H. Freeman and Company, New York (1997), Watson, et al., *Recombinant DNA* ($2^{nd}$ Ed.) W.H. Freeman and Company, New York (1992), and Alberts, et al. *Molecular Biology of the Cell* ($3^{rd}$ Ed.) Garland Publishing, Inc., New York (1994). Other references relating to flow cytometry include, e.g., Radbruch (Ed.) *Flow Cytometry and Cell Sorting*, Springer-Verlag, New York (1992), Owens and Loken, *Flow Cytometry Principles for Clinical Laboratory Practice*, Wiley-Liss, New York (1995), and Jarosqeski and Heller (Eds.) *Flow Cytometry Protocols: Methods in Molecular Biology*, Vol. 91, Humana Press (1997).

The present invention provides microfluidic devices and methods for sorting particles (e.g., fluorescently-labeled particles) that use hydrodynamic flow to focus and/or sort the particles. The methods for sorting members of a particle population (e.g., a cell, a set of cells, a microbead, a set of microbeads, a functionalized microbead, a set of functionalized microbeads, a molecule, a set of molecules, or the like) typically include flowing the members of a particle population in a first microchannel. The members of the particle population are focused horizontally and/or vertically in the first microchannel such that selected individual members are directed into at least a second microchannel that intersects with the first microchannel.

In one embodiment, a portion of the first microchannel optionally includes at least one separation element disposed therein. The separation element generally includes at least two sides in which at least a portion of the separation element is disposed upstream of the second microchannel. In this embodiment, the members of the particle population are optionally focused horizontally and/or vertically in the first microchannel such that selected individual members are directed to at least one of the at least two sides of the separation element and into, e.g., at least a second microchannel that intersects the first microchannel. In other embodiments, this separation element is omitted.

The focusing steps of the particle sorting methods, described above, optionally include horizontally and/or vertically focusing the members of the particle population in the first microchannel by introducing at least one fluid flow (e.g., a buffer, a high density fluid, a low density fluid, or the like) from at least a third microchannel that intersects with the first microchannel upstream from, e.g., the second microchannel. This is optionally performed by any method for flowing fluid in a microfluidic device, including electrokinetic flow, pressure-based flow, and the like.

For example, methods employing electrostatic forces to transport and focus samples generally involve inducing sample flow in a transport channel by applying a first electrical potential to the channel. Thereafter, a second electrical potential is typically applied to focusing-channels that intersect with the transport channel in a cross-configuration to vertically focus the transported sample in the center of the transport channel. This electrokinetic-based system is also optionally utilized to direct or "nudge" flowing samples to effect a sorting function, e.g., by applying an electrical potential to at least one of the intersecting focusing channels to direct sample flow towards or away from that focusing channel and into, e.g., an additional intersecting channel or into a channel region. That is, electrokinetic force can be applied to "nudge" materials across the width of a first channel at an intersection of the first channel and a second channel, resulting in downstream focusing of materials in the channel. This application of electrokinetic force is optionally electrokinetic, electroosmotic, or both. See also, e.g., Ramsey et al., "Apparatus and Method for Performing Electrodynamic Focusing on a Microchip," U.S. Pat. No. 5,858,187, issued Jan. 12, 1999. As mentioned, other alternative techniques for inducing the flow of focusing fluids to sort particles according to the methods of the present invention include pressure, hydrostatic, wicking, capillary, and other forces. Fluid direction components based upon these forces are discussed, below.

In another embodiment, the fluid flow is induced by heating (e.g., Joule heating, etc.) a fluid in the third microchannel. Alternatively, the focusing steps include horizontally and/or vertically focusing the members of the particle population in the first microchannel by introducing at least one fluid flow from at least one of at least a third and at least a fourth microchannel that oppose one another and that intersect with the first microchannel upstream from the second microchannel. Similarly, the fluid flow is optionally introduced by heating (e.g., Joule heating or the like) a fluid in at least one of the third or fourth microchannels. Embodiments that involve heat induced fluid flow are discussed further below.

Figure 22:
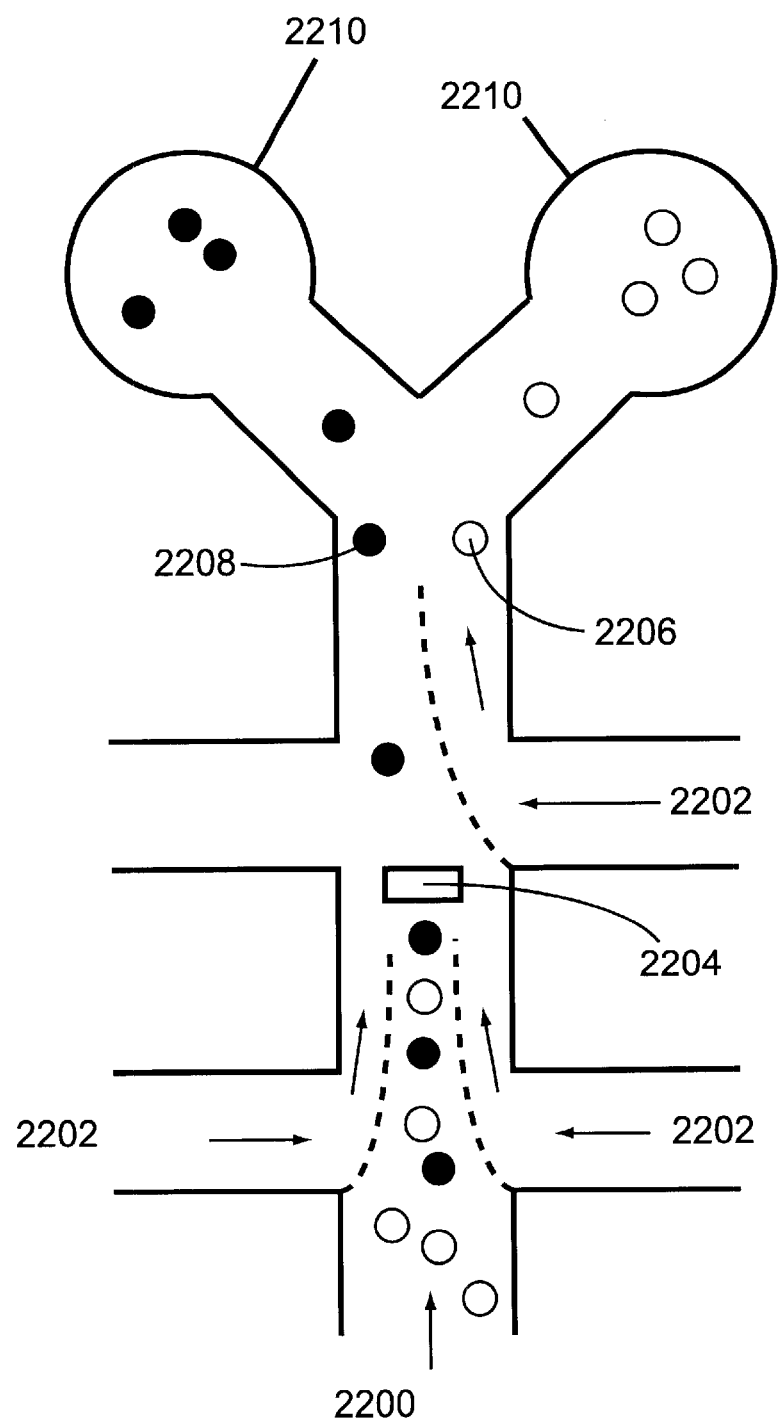
FIG. 22 is a schematic illustration of a particle sorting configuration utilizing sets of opposing microchannels to focus and/or otherwise direct the flow of the members of, e.g., a cell population to achieve cell sorting.

FIG. 22 schematically illustrates one particle sorting configuration utilizing these methods. As shown, cells 2200 are generally flowed in a main microchannel that includes at least two sets of opposing microchannels for focusing and/or otherwise directing the flow of cells 2200 using hydrodynamic flow 2202 (e.g., cell buffer flow). One set of opposing microchannels is typically located, e.g., upstream from detector 2204 for simultaneously introducing hydrodynamic flow 2202 from both microchannels to focus cells 2200, as described above. A second set of opposing microchannels is typically located downstream from detector 2204 for introducing at least one hydrodynamic flow 2202 so as to direct selected cells 2208 (e.g., fluorescently-labeled cells) and non-selected cells 2206 into, in this case, one of two microchannels, each terminating in particular collection wells 2210.

Figure 23:
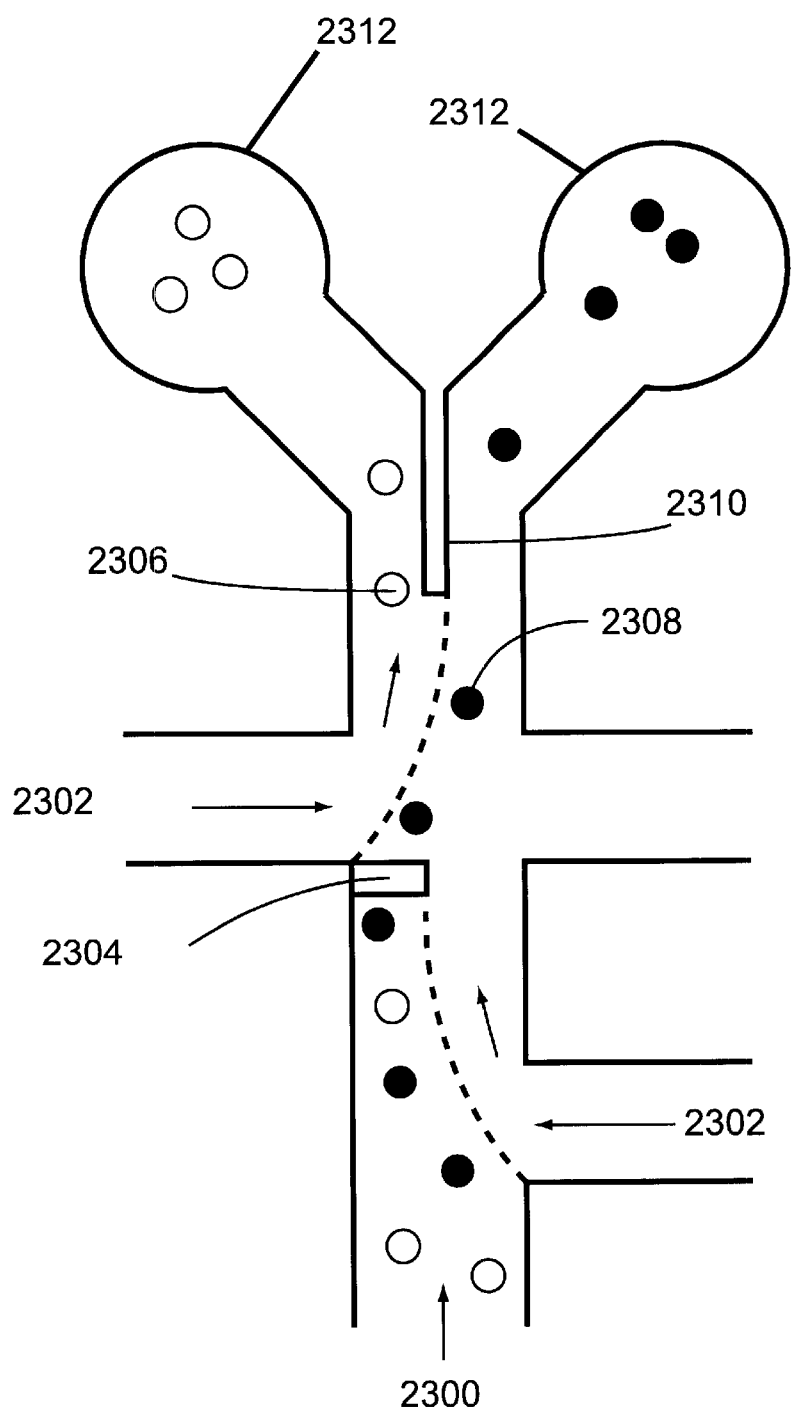
FIG. 23 is a schematic representation of a microchannel configuration that includes one separation element embodiment.

FIG. 23 schematically depicts a microchannel configuration that includes one embodiment of separation element 2310. In this example, cells 2300 are typically flowed in a microchannel that intersects with another microchannel located upstream from detector 2304. The upstream intersecting microchannel is optionally used to focus cells 2300 to one side of the microchannel as cells 2300 pass through detector 2304 using hydrodynamic flow 2302. This illustration also includes a set of opposing microchannels located downstream from the detector for introducing at least one hydrodynamic flow 2302 to direct selected cells 2308 (e.g., fluorescently-labeled cells) and non-selected cells 2306 to either side of separation element 2310 and into, in this case, one of two microchannels, each terminating in particular collection wells 2312. Separation element 2310 is optionally omitted, with cells 2300 or other particles being directed into destination regions as desired.

The inverse relationship between temperature and viscosity for various buffers, gels, and other materials is also optionally exploited in the present invention to effect particle sorting. For example, upon detection of a desired particle, e.g., a buffer or gel disposed in a downstream side-channel is typically heated to decrease fluid viscosity (i.e., to induce fluid flow) to thus direct particles within the microfluidic device. Although any heating source, functional in the devices of the present invention, is optionally used in these embodiments, Joule heating is a preferred method.

Joule heating is typically produced by flowing current through an electrode or other conductive component positioned within a well, microscale channel, or other cavity within the device. The resulting flow of current into fluid within the well, channel, or cavity results in resistive heating of the fluid. By substantially increasing the current across the channel, rapid temperature changes are induced that are optionally monitored by conductivity. Because nanoliter volumes of fluid have tiny thermal mass, transitions between temperatures are typically extremely short. For example, oscillations between any two temperatures above 0° C. and below 100° C. in 100 milliseconds have been performed. Thus, the present invention optionally uses power sources that pass electrical current through, e.g., a focusing channel region for heating purposes. In exemplary embodiments, fluid passes through a channel of a desired cross-section (e.g., diameter) to enhance thermal transfer of energy from the current to the fluid. The channels are optionally formed on almost any type of substrate material such as, amorphous materials (e.g., glass, plastic, silicon), composites, multi-layered materials, combinations thereof, or the like.

In general, electric current passing through fluid in a channel produces heat by dissipating energy through the electrical resistance of the fluid. Power dissipates as the current passes through the fluid and goes into the fluid as energy as a function of time to heat the fluid. The following well-known mathematical expression generally relates the power dissipated in a fluid ("P") to the electric current passing through the fluid ("I") and the electrical resistance of fluid ("R"):

$$P = I^2 R$$

In these embodiments, a portion of the power goes into kinetic energy for moving the fluid through the channel. However, it is also possible to use a selected portion of the power to controllably heat fluid in a channel or selected channel regions, e.g., to further induce fluid movement by reducing fluid viscosity. A channel region suitable for heating is optionally narrower or smaller in cross-section than other channel regions in the channel structure, as a smaller cross-section provides higher resistance in the fluid, which increases the temperature of the fluid as electric current passes through. Alternatively, the electric current is increased across the length of the channel by increased voltage, which also increases the amount of power dissipated into the fluid to correspondingly increase fluid temperature.

To selectively control the temperature of fluid in a region of a channel, a power supply applies voltage and/or current in various ways. For instance, a power supply optionally applies direct current (i.e., DC) or alternating current (AC), which passes through the channel and into a channel region which is, e.g., smaller in cross-section to heat fluid in the region. Alternatively, a power supply applies a pulse or impulse of current and/or voltage, which passes through the channel and into a channel region to heat fluid in the region. Pulse width, shape, and/or intensity are optionally adjusted, e.g., to heat the fluid substantially while moving the fluid. Still further, the power supply optionally applies any combination of DC, AC, and pulse, depending upon the application. In practice, direct application of electric current to fluids in the microchannels of the invention results in extremely rapid and easily controlled changes in temperature.

A controller or computer such as a personal computer is generally used to monitor the temperature of the fluid in the region of the channel where the fluid is heated. The controller or computer typically receives current and voltage information from, e.g., the power supply and identifies or detects fluid temperature in the channel region. The controller or computer also typically receives current information from an operably connected detector, e.g., when a selected particle is detected, which triggers the flow of current through, e.g., one or more Joule heating electrodes. Depending upon the desired temperature of fluid in the region, the controller or computer adjusts voltage and/or current to meet the desired fluid temperature.

In certain embodiments, the region which is heated optionally includes a "coil" which is typically in a planar arrangement. Transfer of heat from the coil to a channel through a substrate material is used to heat the focusing fluids, gels or other materials disposed in the channel. Alternatively, the coil itself is optionally the focusing channel. A voltage is applied between regions of the coil to direct current through the fluid for heating purposes. In particular, a power supply provides a voltage differential between regions of the coil. Current flows between the regions and traverses a plurality of coils or coil loops, which are defined by a substrate. The shape and size of the coils typically influences an ability of current to heat the fluid in the coil. As current traverses through the fluid, energy is transferred to the fluid for heating purposes. Cooling coils are also optionally included.

Figure 24:
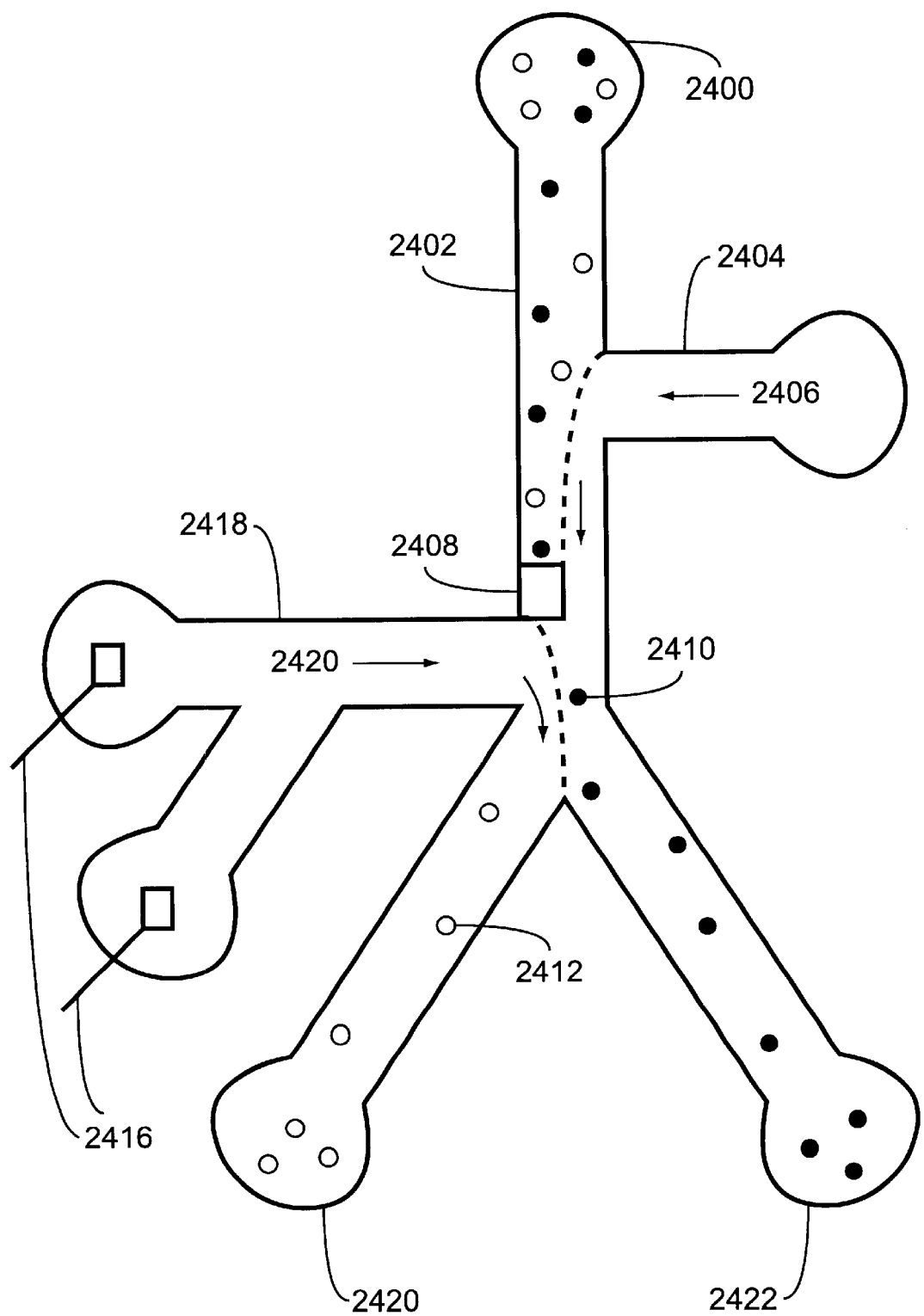
FIG. 24 is a schematic depiction of a microchannel configuration that includes Joule heating electrodes for use in particle sorting.

One embodiment of Joule heating-based particle sorting is schematically illustrated in FIG. 24. As shown, particles are typically flowed from particle well 2400 into main microchannel 2402. In the configuration depicted, focusing microchannel 2404 intersects with main microchannel 2402 in a "T-junction" upstream from detector 2408. Similar to the device represented in FIG. 23 (discussed above), focusing flow stream 2406 is optionally used to focus or pinch the particles against the wall of main microchannel 2402 opposing the "T-junction" as the particles flow through detector 2408. When selected particle 2410 (e.g., a fluorescently-labeled particle) is detected, an electrical signal from detector 2408 typically triggers the flow of current to Joule heating electrodes 2416, which are disposed within wells of branched particle sorting microchannel 2418. Optionally, branched particle sorting microchannel 2418 includes more than two branches or is a single, unbranched microchannel. Additionally, greater or less than two Joule heating electrodes 2416 are optionally included. Although not shown in FIG. 24, conductive coatings are also optionally included in lieu of or in addition to the heating electrodes for effecting the flow of a focusing fluid.

The heat produced by current flowing from Joule heating electrodes 2416 raises the temperature of, e.g., a buffer or gel disposed within branched particle sorting microchannel 2418, thus reducing hydrodynamic resistance in the buffer or gel. The reduced viscosity, in conjunction with vacuum source(s) that are typically operably connected to the device at non-selected particle collection well 2420 and/or selected particle collection well 2422, induce or increase flow of the buffer or gel from branched particle sorting microchannel 2418, which intersects main microchannel 2402 downstream from detector 2408. The induced flow of buffer or gel into main microchannel 2402 thus deflects or redirects the flow of selected particle 2410 into selected particle collection well 2422. In this embodiment, non-selected particle 2412 does not trigger Joule heating/redirecting flow and as such, flows unimpeded into non-selected particle collection well 2420.

Many alternative embodiments that incorporate Joule heating to control fluid viscosity and particle flow are possible. For example, although not shown in FIG. 22, one or both microchannels of the second set of opposing microchannels located downstream from detector 2204 optionally include one or more Joule heating electrodes (e.g., 1, 2, 3, 4, 5, or more electrodes) and/or conductive coating portions. One or both of the opposing microchannels also optionally includes a branched channel structure similar to the branched structure depicted in FIG. 24, above (i.e., branched particle sorting microchannel 2418). Optionally, one or both of the opposing microchannels includes greater than two branches, each branch of which optionally includes one or more Joule heating electrode(s). In other embodiments, separation elements, such as those discussed above are optionally included. Preferred buffers, gels, and other materials used the in these heating embodiments have relatively sharp temperature/viscosity transitions in a narrow temperature range and are generally known in the art. Joule heating is described further in, e.g., in Ser. No. 08/977,528, entitled "Electrical Current for Controlling Fluid Temperatures in Microchannels," filed Nov. 25, 1997 by Calvin Chow, Anne R. Kopf-Sill and J. Wallace Parce; and in PCT/US98/06723, entitled "Closed-Loop Biochemical Analyzers," filed Apr. 3, 1998, by Knapp.

There are various other techniques that are also optionally used to heat buffers, gels, and other materials to effect particle focusing. For example, resistive heating typically results from current applied to conductively coated well or microchannel portions, from one or more electrodes directly (e.g., a thermocouple, etc.), or the like. Other heating methods optionally include directing, e.g., light from a laser source through one or more fiber optic cables to, e.g., wells that fluidly communicate with focusing channels. Heat from other external sources is also optionally utilized in the methods described herein.

WASHING CELLS IN MICROFLUIDIC CHANNEL SYSTEMS

In one aspect, the invention provides in-system cell washing capability. This concept is also optionally extended to washing any other particulate sample. For an extensive description of microfluidic systems comprising particles, see, U.S. Provisional Patent Application No. 60/128,643, filed Apr. 4, 1999, entitled "Manipulation of microparticles in microfluidic systems," by Mehta et al. In this embodiment, diffusible substances such as antibodies, proteins, salts, drugs, etc. are removed by washing the materials away from the particles in a microscale system.

Figure 3:
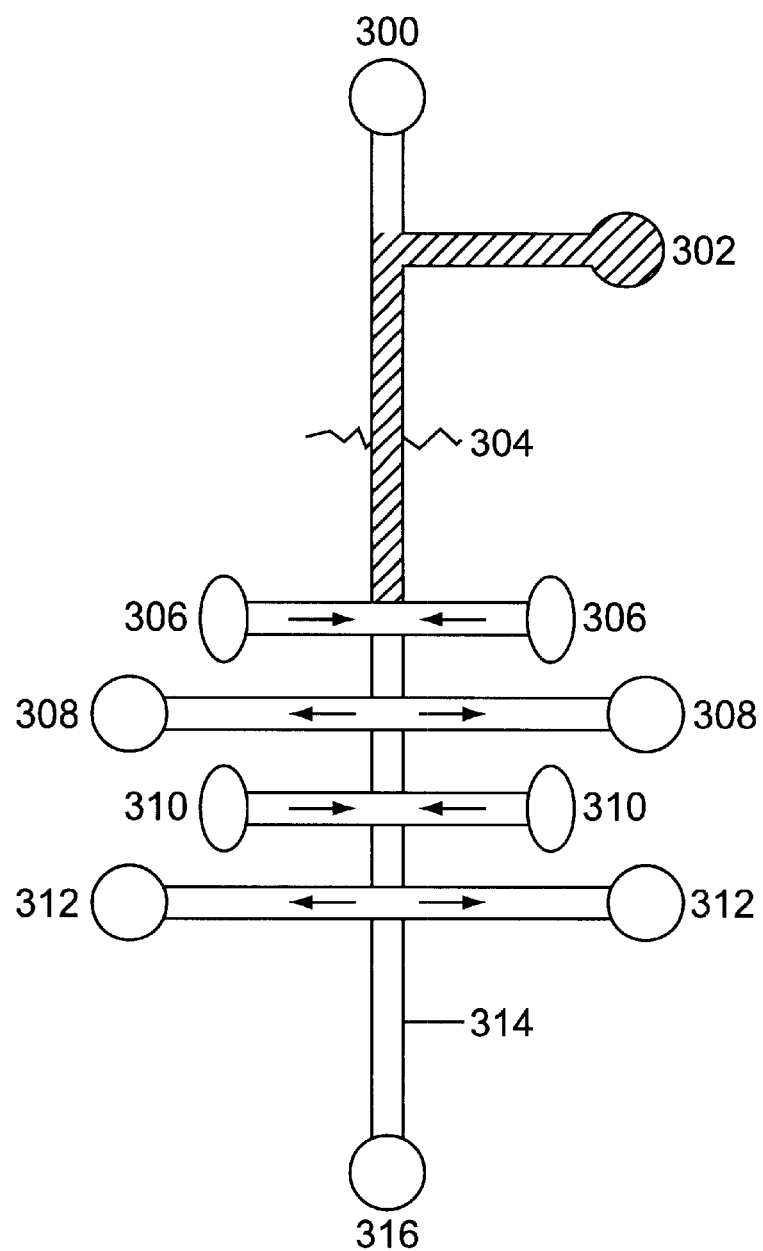
FIG. 3 is a schematic drawing of a microfluidic system adapted to washing reagents from microparticles.

For this embodiment of the invention, lateral channels are placed downstream of the point at which diffusible substances are present in a central main channel. For example, as illustrated in FIG. 3, cells flowed from sample well 300 are optionally incubated with labeled antibody flowed from test compound well 302 in incubation channel region 304, with lateral channels being placed downstream of incubation channel region 304. Wash buffer is typically injected simultaneously from both sides of the main channel from lateral wash channels 306. Although not shown, wash buffer is optionally sequentially introduced into the main channel from lateral wash channels that intersect the main channel in an offset intersection region (i.e., the lateral wash channels are at least somewhat staggered, instead of intersecting directly across from one another). This buffer is then generally removed by flowing the diffusible material into another set of lateral wash channels 308. Further washing is optionally achieved by placing additional lateral wash channels 310 farther downstream from incubation channel region 304 for flowing wash buffer into the main channel and additional wash channels 312 are also optionally included for flowing wash buffer out of the main channel. By repeating wash in-wash out steps, diffusible materials are removed from the main channel. Thereafter, labeled cells are optionally detected in detection zone 314 and subsequently flowed into waste well 316.

Assuming laminar flow, the cells or other particles remain centered in the main channel and do not flow into the lateral wash channels, preventing clogging of the wash channels. Flow in the main channel, and in the wash channels is optionally performed by electrokinetic or pressure-based flow of materials.

CELL VIABILITY SCREENING

The methods and systems of the present invention are particularly applicable in performing cell viability assays as well as for screening test compounds for their effects on cell viability. Such assays are generally utilized in performing toxicity studies, antibiotic screening methods, or the like, and are particularly suitable for the methods and systems of the present invention. Accordingly, in these aspects, the cellular function specific indicator is an indicator of cell viability.

In operation, the suspension of cells typically includes a label. The cells are optionally treated with a second function labeling group that indicates the viability of the cells in the suspension. Specifically, the function label preferentially stains or labels either viable or non-viable cells. A variety of viability indicative dyes are generally commercially available. For example, fluorogenic esterase substrates, such as Calcein AM, BCECF AM and fluorescein diacetate, are optionally loaded into adherent or nonadherent cells, and are suitable indicators of cell viability. Specifically, these esterase substrates measure both esterase activity, which is required to activate the fluorescence of the dye, as well as cell-membrane integrity, which retains the fluorescent materials intracellularly. Other suitable viability indicators include polyfluorinated fluorescein derivatives (i.e., DFFDA, TFFDA, HFFDA and $Br_4$TFFDA), polar nucleic acid based dyes (i.e., SYTOX Green™), dimeric and monomeric cyanine dyes (i.e., TOTO™ and TO-PRO™ series dyes from Molecular Probes), ethidium and propidium dyes (i.e., ethidium bromide, ethidium homodimer-and propidium iodide).

Depending upon the viability indicator used, the level of function label is indicative of the number of either viable or non-viable cells, while the level of reference label is indicative of the number of total cells, e.g., viable and non-viable. Comparison of the levels of the two labels then provides an indication of the relative viability of the cells in the suspension, regardless of the number of cells being detected, e.g., multiple cells, aggregates, or individual cells). In particular, where two cell populations show a similar level of reference label, but one population shows a lower level of viability indicator, it will be understood that the second population is less viable, e.g., has more nonviable cells. It will be appreciated that many dyes or labels described for use as reference labels are also often used as viability labels. Accordingly, it will generally be desirable to select a reference label that labels both viable and nonviable cellular material, and which is distinguishable from the function label. Examples of such reference labels include, e.g., lipophilic membrane labels, or the like.

In performing screening assays, cell suspensions that are exposed to different test compounds or agents are flowed past the detection point and the relative viability of the cells is determined, as compared to a control. Increases or decreases in cellular viability indicate that the compound or agent improves or decreases cellular viability. Such assays are readily employed in identifying antimicrobial, antibiotic or other viability affecting agents. Similarly, such assays are optionally employed in screening for effectors of pathways involved in apoptosis or programmed cell death, e.g., ras mediated pathways.

The methods and devices of the present invention are optionally used to perform the cell viability assays described herein. In one embodiment, e.g., cells exposed to selected test compounds are washed free of excess staining dyes or the like before being focused horizontally and/or vertically as they flow past a detection point to obtain accurate fluorescent readings (e.g., derived from function and/or reference labels). Thereafter, cells (e.g., viable and nonviable cells) are optionally sorted similarly using hydrodynamic flow. These embodiments are depicted, e.g., in FIGS. 22 and 23, which are discussed further above.

ELIMINATING ADSORPTION OF MATERIALS DURING FLOW

Adhesion of materials during pressure-based flow using prior art methods can be problematic, because the flow velocity at the channel wall is low. This low flow velocity increases the time that a material remains in position proximal to a given region of the microscale channel. This increased proximity to a single region leads to formation of strong interactions between the channel region and the material. Thus, one particular advantage of the present method is that focusing of materials in the center of microchannels inhibits adsorption of the materials to the walls of microscale channels and other microscale elements during flow of the materials.

ASSAY SYSTEMS

As noted above, the methods and systems of the present invention are useful in assaying for virtually any cellular function, provided that either the function or a result of the function is independently detectable. In biological applications, and particularly pharmaceutical research, a number of specific types of assays-are generally used as screening models for the identification of potential drug candidates, or "lead compounds." The assay types most frequently used in these screening operations generally include transport assays, binding assays, viability assays, and expression assays.

Transport

In a first aspect, the methods and systems of the present invention are used in assaying cellular transport functions, i.e., ion flux, and intracellular pH regulation. In particular, cellular transport channels have been generally shown to be responsive to important cellular events, e.g., receptor mediated cell activation, and the like. For example, G-protein coupled receptors have been shown to directly or indirectly activate or inactivate ion channels in the plasma membrane or endosomal membranes of cells, thereby altering their ion permeability and thus effecting the excitability of the membrane and intracellular ion concentrations. See, Hille, *Ionic Channels of Excitable Membranes*, Sinauer Assoc. (1984).

In accordance with this aspect of the present invention, therefore, the function specific label comprises an indicator of the level of a particular intracellular species. In particularly preferred aspects, the intracellular species is an ionic species, such as $Ca^{2+}$, $Na^+$, $K^+$, $Cl^-$, or $H^+$ (e.g., for pH measurements). A variety of intracellular indicator compounds are commercially available for these ionic species (e.g., from Molecular Probes, Eugene OR). For example, commonly used calcium indicators include analogs of BAPTA (1,2-bis(2-aminophenoxy)ethane-N,N,N',N'-tetraacetic acid), such as Fura-2, Fluo-2 and Indo-1, which produce shifts in the fluorescent excitation or emission maxima upon binding calcium, and Fluo-3 and Calcium Green-2, which produce increases in fluorescence intensity upon binding calcium. See also, U.S. Pat. No. 5,516,911. Sodium and potassium sensitive dyes include SBFI and PBFI, respectively (also commercially available from Molecular Probes). Examples of commercially available chloride sensitive indicators include 6-methoxy-N-(sulfopropyl)quinolinium (SPQ), N-(sulfopropyl)acridinium (SPA), N-(6-methoxyquinolyl)acetic acid, and N-(6-methoxyquinolyl)acetoethyl ester (Molecular Probes, Inc.), all of which are generally quenched in the presence of chloride ions.

In a related aspect, the function specific indicator is an intracellular pH indicator compound. Specifically, intracellular pH changes have been found to be associated with biologically and pharmaceutically important cellular events, including cell proliferation, apoptosis, fertilization, malignancy, ion transport, drug resistance, lysosomal storage disorders, and Alzheimer's disease. A variety of indicator compounds are commercially available to indicate the intracellular pH of cells, and are readily applicable to the present invention as indicators of cellular function. Examples of these pH indicators include, e.g., SNARFL, SNARF, BCECF, and HPTS, available from Molecular Probes, Inc.

In operation, a suspension of cells that is to be assayed is flowed along a channel. The cells include a reference label as described above, e.g., SYTO® dyes available from Molecular Probes. The cells are also treated with an-intracellular indicator of the level of the species for which relative transport levels are to be determined, and which indicator is distinguishable from the reference label. As a specific example, the cells are optionally stained with, e.g., SYTO®-62 as a reference label. SYTO®-62 is a red nucleic acid dye that is generally excited by light at approximately 655 nm, and which emits light at approximately 675 nm. The cells are also optionally treated with an intracellular calcium indicator, e.g., Fluo-3, also available from Molecular Probes, which is excited at 488 nm and emits at approximately 530 nm. The two labels are easily distinguishable based upon their differing fluorescent emission maxima.

At a point in the channel, the cells are illuminated with a broad spectrum of light, e.g., light that encompasses the excitation maxima of both the SYTO®-62 and Fluo-3 labels. Emitted fluorescence is then passed through optical filtering systems that separate and separately detect the SYTO®-62 fluorescence and the Fluo-3 fluorescence. The levels of fluorescence from each dye are then compared. For example, the comparison optionally includes plotting the level of reference label versus the level of function label. Over the course of the assay, a number of separate data points are gathered that represent different cells or groups of cells that are detected. These are plotted and the slope of the resulting line is calculated. Changes in this slope are indicative of changes in the level of the function that is being assayed.

Binding

I. Generally

In an alternate aspect, the methods and systems of the present invention are used in assaying cellular binding functions, such as ligand-receptor binding, nucleic acid hybridization, antigen/antibody binding, cell-cell interactions, and the like. As with transport functions, cellular binding functions are often necessary precursors to a variety of cellular functions. Specifically, many biological responses are often triggered and/or controlled by the binding of a receptor to its ligand. For example, interaction of growth factors, i.e., EGF, FGF, PDGF, etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Accordingly, control of the interaction of the receptor and its ligand may offer control of the biological responses caused by that interaction. As noted, included within these biological functions controlled by binding reactions are many transport functions, e.g., G-protein linked receptor activation, as set forth above. Accordingly, these binding functions may be detected by detecting the downstream event for which binding is a precursor, e.g., enhanced or decreased transport function, expression of receptor linked reporter label, protein translocation, or by detecting actual binding of cells with a binding agent, e.g., a ligand, nucleic acid or the like, through the inclusion in the ligand of a binding indicator, e.g., fluorescent resonance energy transfer dyes (FRET), molecular beacons, etc. For example, in the case of cell-cell interactions, detection of binding may be accomplished by labeling the cells' surfaces with both elements of appropriate FRET dyes, e.g., energy donor and energy acceptor. Upon cell-cell binding, these elements are placed in sufficient proximity for energy transfer, allowing their detection.

Alternatively, fluorescence polarization detection methods are used to detect binding of relatively small molecules, e.g., ligands, antibodies, etc., to relatively large structures, e.g., cells. Fluorescence polarization assays for use in microfluidic systems are generally described in Provisional U.S. Application No. 60/088,650, filed Jun. 8, 1998, incorporated herein by reference.

A variety of other detection/labeling mechanisms are also available for detecting binding of one molecule, e.g., a ligand or antibody, to another molecule, e.g., a cell surface receptor. For example, a number of labeling materials change their fluorescent properties upon binding to hydrophobic sites on proteins, e.g., cell surface proteins. Such labels include, e.g., 8-amino-1-naphthalene sulfonate (ANS), 2-p-toluidinylnaphthalene-6-sulfonate (TNS) and the like. Alternatively, detectable enzyme labels are utilized that cause precipitation of fluorescent products on solid phases, i.e., cell surfaces are optionally used as function indicators of binding. For example, alkaline phosphatase substrates that yield fluorescent precipitates are optionally employed in conjunction with alkaline phosphatase conjugates of cell binding components. Such substrates are generally available from Molecular Probes, Inc., and are described in, e.g., U.S. Pat. No. 5,316,906 and U.S. Pat. No. 5,443,986.

II. Cell Rolling Assays

In a related but alternative aspect, the present invention provides methods, devices and systems for use in performing in vitro cell rolling assays. In particular, it has been reported that several classes of cell adhesion molecules participate in a wide range of important physiological functions, including wound healing, inflammation and cancer metastasis. Some examples of these molecules include selectins and integrins which mediate the rolling and subsequent immobilization of white blood cells along the endothelial lining of blood vessel, thus allowing them to migrate out of the blood vessel and toward the target tissue. Cell rolling assays are designed to mimic in vitro the rolling phenomenon in vivo, to create a more effective model for use in screening potential effectors of that phenomenon. See, e.g., Lawrence et al., J. Immunol., (1993) 151:6338–6346 and Brunk et al., Biophys. J. (1997) 72:2820–2833.

Generally, the assay is performed by flowing a suspension of cells over a surface upon which ligands are immobilized, and observing the numbers of firmly attached and/or rolling cells on that surface as well as the velocity of the rolling cells. The present invention employs the microfluidic systems described herein, in the performance of these assay types. In particular, as described in greater detail below, the cell suspension bearing an appropriate reference label is introduced into a channel in which an appropriate ligand of interest is immobilized on the inner surface.

Immobilization of ligands on the interior surface of channels is optionally accomplished by covalently attaching the ligands to the surface or by adsorbing the ligands on the surface. Covalent attachment of ligands to surfaces of solid substrates has been described in the art. See, e.g., Sundberg, et al., J. Am. Chem. Soc. (1995) 117:12050–57.

In accordance with the present invention, the cell suspension is flowed through the channel, i.e., using pressure flow, as described in greater detail below, and the number of cells that are rolling over or firmly attached to the interior surface of the channel is monitored using an appropriate detection system. Alternatively, cells are pulsed through the channel to facilitate their monitoring. Typically, such systems employ a video imaging system that images and identifies the cells as they enter the imaged area, and tracks the cells path through the field, determining their relative velocity. Alternatively, point detection systems, e.g., as described herein, are used which detect cells at two separate points in the channel, and determine their relative velocity. In the latter case, it is generally desirable to provide the cells in suspension that is sufficiently dilute so as to permit correlation between the two detectors. Alternatively, cells may be coded with mixtures of different, distinguishable labels to permit the correlation among cells between points. Such coded cells optionally include wide varieties of different labels, or alternatively, include a set of two, three, four, five, six, seven or eight different labels at varying relative levels, where the profile of the relative levels of labels identifies the different cells.

In screening assays, the test compounds are introduced into a channel, e.g., via an external sample accessing capillary (e.g., an electrokinetic injector or other capillary element) where they contact the suspension of cells. The cell suspension is then assayed for rolling or firmly attached cells, and the effect of the test compound, if any, on the cell rolling or binding is determined as compared to the control, e.g., in the absence of the test compound.

III. Expression

In a further aspect, the methods and systems of the present invention are used to assay cellular expression functions, and particularly, for the effect of test compounds on such cellular expression. Such assays are generally utilized in screening for effectors of given biological processes, which effectors target those functions at the gene expression level. In accordance with the present invention, therefore, the function label is indicative of the level of gene expression, for a particular gene of interest.

Gene expression levels are typically assayed by quantifying the level of gene product from the gene of interest, e.g., the amount of protein produced by the cells. Alternate methods of gene expression analysis examine the amount of RNA transcribed from the gene of interest. Typically, such assays involve the use of a nucleic acid hybridization assay to identify a pattern of RNA transcription following an activating event.

The methods and systems of the present invention are readily applied to such expression analyses. In particular, in accordance with the present invention, the function label is typically provided that is expressed by the cells during the expression function. For example, chimeric reporter systems are optionally employed as function labels or indicators of gene expression. Chimeric reporter systems typically incorporate a heterogeneous reporter system integrated into the coding sequence of the gene of interest. The expression of the gene of interest is then accompanied by the expression of the reporter, which is then detected. For example, a receptor may be a fusion between the product of the gene of interest and heterologous protein, e.g., an enzyme whose activity is readily assayable, or an otherwise detectable protein, e.g., luciferase, aequorin, green fluorescent protein (GFP), β-galactosidase, alkaline phosphatase, or the like. The expressed reporter is then detected and compared with the level of reference label, to provide a quantitative determination of expression levels on a per cell basis. Expression of gene products to a detectable level can require varying amounts of time, e.g., several minutes to hours. Accordingly, the assay time is varied to allow such expression. As noted herein, such variation is generally accomplished by slowing the flow rates of the cell suspension through a channel and/or lengthening the channel.

Alternatively, the function label is provided as an element of a binding molecule that specifically associates with the downstream indicator of gene expression, e.g., an expressed protein, wherein the binding of the binding molecule (bearing the function label) to the gene product of interest produces a detectable property within the cell, e.g., as described with reference to the binding assays, above. The assay methods are then carried out in the same manner as described with reference to the binding functions, described above. In the case of expressed proteins, the binding molecule optionally includes an antibody specific for the gene product, or a specific binding partner, where the expressed protein is a member of a binding pair, e.g., a receptor or ligand.

Because gene expression assays typically require much longer incubation times than other assay types described herein, modified methods are optionally employed. For example, in one aspect, cells are flowed through the channel of the system, and preferably, through multiple parallel channels of the system, and contacted with surfaces of the channel(s) that cause them to adhere. Test compounds are then introduced into the channel(s) and allowed to flow over the adhered cells, e.g., for from 5 to 60 minutes. Any effects of these test compounds on the level of function label, and therefore, gene expression, is determined in the channel(s), and compared to the level of reference label. The comparison then allows quantification of the level of expression on a per cell basis. Optionally, the reaction channel is provided such that the travel time of the cells from the point of test compound addition to detection is sufficient to permit appropriate expression analysis. In certain aspects, tortuous channels, e.g., serpentine channels, and the like, are used to extend channel lengths to expand the travel time. Alternatively or additionally, flow rates are substantially reduced to increase this travel time.

SCREENING ASSAYS

As noted repeatedly above, the assays described herein are particularly useful in performing high-throughput screening assays. As used herein, the term "test compound" refers to the collection of compounds that are to be screened for their ability to affect a particular biochemical system. Test compounds optionally include a wide variety of different compounds, including chemical compounds, mixtures of chemical compounds, e.g., polysaccharides, small organic or inorganic molecules, biological macromolecules, e.g., peptides, proteins, nucleic acids, or an extract made from biological materials such as bacteria, plants, fungi, or animal cells or tissues, naturally occurring or synthetic compositions. Depending upon the particular embodiment being practiced, the test compounds may be provided, e.g., injected, free in solution, or may be attached to a carrier, or a solid support, e.g., beads. A number of suitable solid supports may be employed for immobilization of the test compounds. Examples of suitable solid supports include agarose, cellulose, dextran (commercially available as, e.g., Sephadex®, Sepharose®, etc.), carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylenemaleic acid copolymer, nylon, silk, etc. Additionally, for the methods and apparatuses described herein, test compounds may be screened individually, or in groups. Group screening is particularly useful where hit rates for effective test compounds are expected to be low such that one would not expect more than one positive result for a given group. Alternatively, such group screening is optionally used where the effects of different test compounds are differentially detected in a single system, e.g., through electrophoretic separation of the effects, or differential labeling which enables separate detection.

Typically, vast libraries of test compounds are separately tested for potential effects on different cellular functions. In preferred aspects, large libraries of chemical compounds prepared using combinatorial synthesis techniques are typically employed as test compounds in high-throughput screening applications, to identify any such compounds that may have pharmacologically beneficial activities. In optional preferred aspects, test compounds include large libraries of naturally occurring materials or compounds, libraries of genetic material, protein fragments, and the like.

In general, the test compounds are separately introduced into the assay systems described herein. The relative level of a particular cellular function is then assessed in the presence of the test compound, and this relative level of function is then compared to a control system, which lacks an introduced test compound. Increases or decreases in relative cellular function are indicative that the test compound is an enhancer or an inhibitor of the particular cellular function, respectively.

OVERALL SYSTEMS

As noted above, the present invention also provides systems and devices used to practice the above-described methods. The system includes a channel along which is flowed a suspension of cells or other particles, and cell focusing means as noted above (laminar flow focusing channels, density gradient layers, or both). A source of different test compounds is optionally linked to the channel, for introducing the different test compounds into the channel whereupon they are contacted with, e.g., the cells. One or more detectors are also provided in sensory communication with the channel, e.g., for detecting and quantifying both the level of reference label and the level of function label present on the cells. As used herein, the phrase "sensory communication" refers to orientation of the detector such that it is capable of obtaining an appropriate signal from the point of interest. In the case of optical detectors, sensory communication provides a detector oriented such that it is capable of receiving an optical signal from a channel of a microfluidic device. Such detection is optionally direct, or includes an intervening optical pathway, e.g., lenses, fiber optics, etc. In the case of chemical detectors, such sensory communication typically requires a sensor component disposed in contact with the fluid material within the channel.

The detector(s) is/are operably linked to a processor, e.g., a computer, for recording the detected signals, and providing a report of relative activity of the cells that are being assayed. The computer also typically includes appropriate programming for determining whether one assay, e.g., a first screening assay, shows greater or lesser cellular function than another assay, e.g., a control.

Detector systems optionally includes one or more different detector elements, and are selected to detect relevant labels present in the cells. For example, in the case of cells that include reference and function labels that are fluorescent, the detector typically includes a dual wavelength fluorescent detector. This detector typically includes a light source. Appropriate light sources typically vary depending upon the type of detection being employed. For example, in some cases broad spectrum illumination is desirable while in other cases, a narrower spectrum illumination is desired. Typically, the light source is a coherent light source, such as a laser, or laser diode, although other light sources, such as LEDs, lamps or other available light sources are also optionally employed. In the case of a fluorescent detector, excitation light, e.g., light of appropriate wavelength to excite labels, from the light source is directed at an analysis channel, e.g., disposed in a microfluidic device, via an optical train that includes optional lens, beam splitters, and objective lenses In some instances, electrolkinetic material transport systems are used to direct one or more of the flow of cell suspensions, the injection of test compounds, and other material movement parameters. In such cases, the overall system used in performing the assay will typically include an appropriate controller and interface for controlling such electrokinetic material transport. Typically, such transport systems include one or more electrical power supplies that are operably coupled to the termini of the channels in a microfluidic device, e.g., as described in greater detail below. The connection of the power supply(ies) with the channels is typically accomplished via electrodes placed into reservoirs at the termini of the channels, which electrodes are coupled to the power supply(ies). The power supply(ies) then deliver(s) appropriate voltage levels to the various electrodes to yield a desired flow pattern within the channels of the device, e.g., flowing the cell suspension and periodically injecting a test compound: The power supply is typically linked to an appropriately programmed computer which directs the application of voltages in accordance with a user selected flow profile.

ASSAY DEVICES

Microfluidic devices and assay components which are optionally adapted to the present invention are described in various PCT applications and issued U.S. Patents, such as, U.S. Pat. No. 5,699,157 (J. Wallace Parce) issued Dec. 16, 1997, U.S. Pat. No. 5,779,868 (J. Wallace Parce et al.) issued Jul. 14, 1998, U.S Pat. No. 5,800,690 (Calvin Y. H. Chow et al.) issued Sep. 1, 1998, U.S. Pat. No. 5,842,787 (Anne R. Kopf-Sill et al.) issued Dec. 1, 1998, U.S. Pat. No. 5,852,495 (J. Wallace Parce) issued Dec. 22, 1998, U.S. Pat. No. 5,869,004 (J. Wallace Parce et al.) issued Feb. 9, 1999, U.S. Pat. No. 5,876,675 (Colin B. Kennedy) issued Mar. 16, 1999, U.S. Pat. No. 5,880,071 (J. Wallace Parce et al.) issued Mar. 9, 1999, U.S. Pat. No. 5,882,465 (Richard J. McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 7, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999, U.S. Pat. No. 5,958,203 (J. Wallace Parce et al.) issued Sep. 28, 1999, U.S. Pat. No. 5,958,694 (Theo T. Nikiforov) issued Sep. 28, 1999, U.S. Pat. No. 5,959,291 (Morten J. Jensen) issued Sep. 28, 1999, U.S. Pat. No. 5,964,995 (Theo T. Nikiforov et al.) issued Oct. 12, 1999, U.S. Pat. No. 5,965,001 (Calvin Y. H. Chow et al.) issued Oct. 12, 1999, U.S. Pat. No. 5,965,410 (Calvin Y. H. Chow et al.) issued Oct. 12, 1999, U.S. Pat. No. 5,972,187 (J. Wallace Parce et al.) issued Oct 26, 1999, U.S. Pat. No. 5,976,336 (Robert S. Dubrow et al.) issued Nov. 2, 1999, U.S. Pat. No. 5,989,402 (Calvin Y. H. Chow et al.) issued Dec. 23, 1999, U.S. Pat. No. 6,012,231 (Anne R. Kopf-Sill) issued Dec. 14, 1999, U.S. Pat. No. 6,011,252 (Morten J. Jensen) issued Jan. 4, 2000, U.S. Pat. No. 6,012,902 (J. Wallace Parce) issued Jan. 11, 2000, U.S. Pat. No. 6,042,709 (J. Wallace Parce et al.) issued Mar. 28, 2000, U.S. Pat. No. 6,042,710 (Robert S. Dubrow) issued Mar. 28, 2000, U.S. Pat. No. 6,046,056 (J. Wallace Parce et al.) issued Apr. 4, 2000, U.S. Pat. No. 6,048,498 (Colin B. Kennedy) issued Apr. 11, 2000, U.S. Pat. No. 6,068,752 (Robert S. Dubrow et al.) issued Mar. 30, 2000, U.S. Pat. No. 6,071,478 (Calvin Y. H. Chow) issued Jun. 6, 2000, U.S. Pat. No. 6,074,725 (Colin B. Kennedy) issued Jun. 13, 2000, U.S. Pat. No. 6,080,295 (J. Wallace Parce et al.) issued Jun. 27, 2000, U.S. Pat. No. 6,086,740 (Colin B. Kennedy) issued Jul. 11, 2000, U.S. Pat. No. 6,086,825 (Steven A. Sundberg et al.) issued Jul. 11, 2000, U.S. Pat. No. 6,090,251 (Steven A. Sundberg et al.) issued Jul. 18, 2000, U.S. Pat. No. 6,100,541 (Robert Nagle et al.) issued Aug. 8, 2000, U.S. Pat. No. 6,107,044 (Theo T. Nikiforov) issued Aug. 22, 2000, U.S. Pat. No. 6,123,798 (Khushroo Gandhi et al.) issued Sep. 26, 2000, U.S. Pat. No. 6,129,826 (Theo T. Nikiforov et al.) issued Oct. 10, 2000, U.S. Pat. No. 6,132,685 (Joseph E. Kersco et al.) issued Oct. 17, 2000, U.S. Pat. No. 6,148,508 (Jeffrey A. Wolk) issued Nov. 21, 2000, U.S. Pat. No. 6,149,787 (Andrea W. Chow et al.) issued Nov. 21, 2000, U.S. Pat. No. 6,149,870 (J. Wallace Parce et al.) issued Nov. 21, 2000, U.S. Pat. No. 6,150,119 (Anne R. Kopf-Sill et al.) issued Nov. 21, 2000, U.S. Pat. No. 6,150,180 (J. Wallace Parce et al.) issued Nov. 21, 2000, U.S. Pat. No. 6,153,073 (Robert S. Dubrow et al.) issued Nov. 28, 2000, U.S. Pat. No. 6,156,181, (J. Wallace Parce et al.) issued Dec. 5, 2000, U.S. Pat. No. 6,167,910 (Calvin Y. H. Chow) issued Jan. 2, 2001, U.S. Pat. No. 6,171,067 (J. Wallace Parce) issued Jan. 9, 2001, U.S. Pat. No. 6,171,850 (Robert Nagle et al.) issued Jan. 9, 2001, U.S. Pat. No. 6,172,353 (Morten J. Jensen) issued Jan. 9, 2001, U.S. Pat. No. 6,174,675 (Calvin Y. H. Chow et al.) issued Jan. 16, 2001, U.S. Pat. No. 6,182,733 (Richard J. McReynolds) issued Feb. 6, 2001, U.S. Pat. No. 6,186,660 (Anne R. Kopf-Sill et al.) issued Feb. 13, 2001, and U.S. Pat. No. 6,221,226 (Anne R. Kopf-Sill) issued Apr. 24, 2001; and published PCT applications such as, WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, WO 99/44217, WO 99/56954, WO 99/64836, WO 99/64840, WO 99/64848, WO 99/67639, WO 00/07026, WO 00/09753, WO 00/10015, WO 00/21666, WO 00/22424, WO 00/26657, WO 00/42212, WO 00/43766, WO 00/45172, WO 00/46594, WO 00/50172, WO 00/50642, WO 00/58719, WO 00/60108, WO 00/70080, WO 00/70353, WO 00/72016, WO 00/73799, WO 00/78454, WO 01/02850, WO 01/14865, and WO 01/17797, which are all incorporated herein by reference.

As noted above, the assays of the present invention are carried out within fluidic channels, along which the cell suspensions and/or other particles are flowed. In some cases, the channels may simply be present in a capillary tube, e.g., a glass, fused silica, quartz or plastic capillary. The capillary channel is fluidly coupled to a source of the suspension of cells or other particles, which are then flowed along the capillary channel. In particularly preferred aspects, the channel is integrated into the body structure of a microfluidic device. As used herein, the term "microfluidic" generally refers to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m.

In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 0.1 $\mu$m and 50 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "Y" or "T" intersections, or any number of other structures, whereby two channels are in fluid communication.

The body structure of the microfluidic devices, described herein, typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

In preferred aspects, the bottom portion of the device comprises a solid substrate that is substantially planar in structure, and which has at least one substantially flat upper surface. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices are typically exposed, including extremes of pH, temperature, salt concentration, and application of electric fields. Accordingly, in some preferred aspects, the substrate material optionally includes materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping, or by polymerizing the polymeric precursor material within the mold. See, e.g., U.S. Pat. No. 5,512,131. Such polymeric substrate materials are preferred for their ease of manufacture, low cost and disposability, as well as their general inertness to most extreme reaction conditions. Again, these polymeric materials optionally include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997, and which is incorporated herein by reference in its entirety for all purposes.

The channels and/or chambers of the microfluidic devices are typically fabricated into the upper surface of the bottom substrate or portion of the device, as microscale grooves or indentations, using the above described microfabrication techniques. The top portion or substrate also comprises a first planar surface, and a second surface opposite the first planar surface. In the microfluidic devices prepared in accordance with certain aspects of the methods described herein, the top portion also includes a plurality of apertures, holes or ports disposed therethrough, e.g., from the first planar surface to the second surface opposite the first planar surface.

The first planar surface of the top substrate is then mated, e.g., placed into contact with, and bonded to the planar surface of the bottom substrate, covering and sealing the grooves and/or indentations in the surface of the bottom substrate, to form the channels and/or chambers (i.e., the interior portion) of the device at the interface of these two components. Bonding of substrates is typically carried out by any of a number of different methods, e.g., thermal bonding, solvent bonding, ultrasonic welding, and the like.

The holes in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device. In many embodiments, extensions are provided over these reservoirs to allow for increased fluid volumes, permitting longer running assays, and better controlling fluid flow parameters, e.g., hydrostatic pressures. Examples of methods and apparatuses for providing such extensions are described in, e.g., Dubrow et al., "Microfluidic Devices and Systems Incorporating Cover Layers," WO 99/43432, published Sep. 2, 1999, which are incorporated herein by reference in their entirety for all purposes. These devices are optionally coupled to other sample introduction ports, e.g., one or more pipettor or capillary elements (e.g., 1, 2, 3, 4, 6, 8, 10, 12, or more elements) which serially introduce multiple samples, e.g., from the wells of a microwell plate. Thus, in some embodiments, both reservoirs in the upper surface and external capillary elements are present in a single device. Alternatively, the devices include only one or more capillary elements for sample or other material introduction.

The sources of reagents, samples (e.g., cells, microbeads, DNA or other molecules, etc.), buffers, and other materials are optionally fluidly coupled to the microchannels in any of a variety of ways. In particular, those systems comprising sources of materials set forth in Knapp et al., "Closed Loop Biochemical Analyzers" (WO 98/45481; PCT/US98/06723) and U.S. Pat. No. 5,942,443, issued Aug. 24, 1999, entitled "High Throughput Screening Assay Systems in Microscale Fluidic Devices" to J. Wallace Parce et al. and, e.g., in PCT/US00/04522, filed Feb. 22, 2000, entitled "Manipulation of Microparticles In Microfluidic Systems," by Mehta et al. are applicable.

In these systems, one or more capillary or pipettor elements (i.e., an element that includes, e.g., a channel in which components are optionally moved from a source to a microscale element such as a second channel or reservoir) is temporarily or permanently coupled to a source of material. The source is optionally internal or external to a microfluidic device that includes the pipettor or capillary element.

Example sources include microwell plates, membranes or other solid substrates comprising lyophilized components, wells or reservoirs in the body of the microscale device itself and others. In one preferred embodiment, one or more capillary elements are used to draw cell or other samples from microwell plates into the body structure of the device. The channel disposed in the capillary element typically includes a diameter in the range of about 1 $\mu$m to about 100 $\mu$m, more preferably in the range of about 25 $\mu$m to about 75 $\mu$m, e.g., about 50 $\mu$m in diameter. These devices are typically included as part of an automated or integrated system which further enhances device throughput. Integrated systems are discussed further above and in the references cited herein.

In many embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows are optionally merely a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials are optionally separately manufactured into the device.

In many aspects, it is desirable to provide the interior surfaces of the channels with an appropriate treatment to prevent the adhesion of cells or other particles to that surface. For example, in the case of glass or other highly charged channel surfaces, some cell types often have a tendency to stick to the channel surfaces, interfering with the flowing of cells through the channels. For example, in the case of mammalian cell-based assays, many mammalian cell types are particularly adherent to certain types of surfaces, e.g., glass and some plastics. Accordingly, in some embodiments, it is desirable to treat or coat the interior surfaces of the channels to prevent cell adhesion. A variety of surface treatments are optionally employed to accomplish this goal. For example, charge masking coatings such as polyols (e.g., polyvinylalcohol (PVA)), polyethyleneimine (PEI), polyethylene glycol (PEG), polyacrylamides (e.g., polyacrylamide, polymethylacryalamide, polydimethacrylamide, and the like), carbohydrates such as polysucrose (Ficoll™), polyglucose (dextran and cellulose), and polytetrafluoroethylene (Teflon™), or the like. Alternatively, covalent surface treatments are also optionally used to prevent surface adhesion of cells, such as silanization (e.g., using dimethyl or dichlorosilane) of glass or plastic surfaces. Other surface treatments are generally described, with reference to device fabrication techniques, above.

The flowing of the suspension of cells or other particles along one or more channels of the devices described herein is optionally carried out by a number of mechanisms, including pressure based-flow, electrokinetic flow, or other mechanisms or combinations of mechanisms. In a first preferred aspect, a pressure differential is used to flow the suspension of cells along a channel. Application of a pressure differential along a channel is carried out by a number of means. For example, in a simple passive aspect, the cell suspension is deposited in a reservoir at one end of a channel and at a sufficient volume or depth, that the cell suspension creates a hydrostatic pressure differential along the length of the channel, e.g., by virtue of its having greater depth than a reservoir at an opposite terminus of the channel. The hydrostatic pressure then causes the cell suspension to flow along the length of the channel. Typically, the reservoir volume is quite large in comparison to the volume or flow through rate of the channel, e.g., 10 $\mu$l reservoirs, vs. 1000 $\mu$m$^2$ channel cross-section. As such, over the time course of the assay, the flow rate of the cell suspension will remain substantially constant, as the volume of the reservoir, and thus, the hydrostatic pressure changes very slowly. Applied pressure is then readily varied to yield different cell suspension flow rates through the channel. In screening applications, varying the flow rate of the cell suspension is optionally used to vary the incubation time of the cells with the test compound. In particular, by slowing the cells flow rate along the channel, one can effectively lengthen the amount of time between introduction of test compounds and detection of their effects. Alternatively, channel lengths, detection points, or test compound introduction points are varied in fabrication of the devices, to vary incubation times.

In many applications, it may be desirable to provide relatively precise control of the flow rate of the cell suspension and/or other particles, e.g., to precisely control incubation times, or the like. As such, in many preferred aspects, flow systems that care more active than hydrostatic pressure driven systems are employed. For example, the cell suspension is optionally flowed by applying a pressure differential across the length of a channel. For example, a pressure source (positive or negative) is applied at the cell suspension reservoir at one end of a channel, and the applied pressure forces the suspension through the channel. The pressure source is optionally pneumatic, e.g., a pressurized gas, or alternatively is a positive displacement mechanism, i.e., a plunger fitted into a cell suspension reservoir, for forcing the cell suspension through the analysis channel. Alternatively, a vacuum source is applied to a reservoir at the opposite end of the channel to draw the suspension through the channel. Pressure or vacuum sources are optionally supplied external to the device or system, e.g., external vacuum or pressure pumps sealably fitted to the inlet or outlet of a channel, or they are internal to the device, e.g., microfabricated pumps integrated into the device and operably linked to a channel. Examples of microfabricated pumps have been widely described in the art. See, e.g., published International Application No. WO 97/02357.

In alternate aspects, other flow systems are employed in transporting or focusing the cellular suspension and/or other particles in a channel. In one embodiment, cells are initially flowed under pressure, but focused using alternative fluid direction components, such as an electrokinetic force modulator. While electrokinetic forces typically produce substantially uniform fluid flow in microchannels, they tend to disrupt cellular membranes. Thus, the use of electrokinetic motive forces is typically limited to focusing pressure-based cellular flows, which as discussed have non-uniform flow velocities.

Electrokinetic transport systems typically utilize electric fields applied along the length of channels that have a surface potential or charge associated therewith. When fluid is introduced into the channel, the charged groups on the inner surface of the channel ionize, creating locally concentrated levels of ions near the fluid surface interface. Under an electric field, this charged sheath migrates toward the cathode or anode (depending upon whether the sheath comprises positive or negative ions) and pulls the encompassed fluid along with it, resulting in bulk fluid flow. This flow of fluid is generally termed electroosmotic flow. Where the fluid includes a cell or other particle suspension, those components are also pulled along. A more detailed description of controlled electrokinetic material transport systems in microfluidic systems is described in published International Patent Application No. WO 96/04547, which is incorporated herein by reference.

Hydrostatic, wicking and capillary forces are also optionally used to provide for fluid flow. See, e.g., "Method and Apparatus for Continuous Liquid Flow in Microscale Channels Using Pressure Injection, Wicking and Electrokinetic Injection," by Alajoki et al., Ser. No. 09/245,627, filed Feb. 5, 1999.

In alternative aspects, flow of the cell suspension and/or other particles is driven by inertial forces. In particular, channels are optionally disposed in a substrate that has the conformation of a rotor, with channels extending radially outward from the center of the rotor. The cell suspension is deposited in a reservoir that is located at the interior portion of the rotor and is fluidly connected to the channels. During rotation of the rotor, the centripetal force on the cell suspension forces the cell suspension through the channels, outward toward the edge of the rotor. Multiple channels are typically provided in the rotor to perform multiple different analyses. Detection of the function and reference labels is then carried out by placing a detector under the spinning rotor and detecting the signal as a channel passes over the detector. Examples of rotor systems have been previously described for performing a number of different assay types. See, e.g., Published International Application No. WO 95/02189. Test compound reservoirs are optionally provided in the rotor, in fluid communication with one or more channels, such that the rotation of the rotor also forces the test compounds into the one or more channels.

Although illustrated in the figures herein as a single channel and accessing capillary, it will be readily appreciated that these aspects may be provided as multiple parallel channels and accessing capillaries (discussed above), in order to substantially increase the throughput of the system. Specifically, single body structures are optionally provided with multiple parallel channels coupled to multiple sample accessing capillaries that are positioned to sample multiple samples at a time from sample libraries, e.g., multiwell plates. As such, these capillaries are generally spaced at regular distances that correspond with the spacing of wells in multiwell plates, e.g., 9 mm centers for 96 well plates, 4.5 mm for 384 well plates, and 2.25 mm for 1536 well plates.

The present invention is further illustrated with reference to the following non-limiting examples.

EXAMPLES

TUNEL ASSAY AND ANNEXIN-V ASSAY FOR APOPTOSIS DETECTION

A TUNEL assay (TdT (Terminal deoxynucleotidyl transferase)-mediated dUTP Nick End Labeling) was used to measure cellular apoptosis in accordance with the above-described methods and systems. In a TUNEL Assay, damaged DNA is labeled with fluorescinated nucleotides. Terminal deoxynucleotidyl transferase (TdT) binds to exposed 3' ends of DNA fragments generated in response to apoptotic signals and catalyzes the addition of fluorescein-labeled deoxynucleotides. U937 cells were treated with Campthotecin to induce apoptosis. The cells were then harvested and fixed with 4% formaldehyde and stored in 80% ethanol at +4° C. until labeling was performed.

The cells were rehydrated in TBS buffer. They were then treated with 20 µg/ml of proteinase K for 5 minutes and resuspended in equilibration buffer. The cells were incubated in a working TdT labeling reaction mixture from Oncogene Research Products containing TdT enzyme and FragEL TdT labeling reaction mix. The cells were resuspended in TBS and then counterstained with a DNA dye (SYTO®-62 DNA dye at 1 µM for 10 minutes RT) to obtain a total cell count.

After washing the cells in TBS, they were resuspended in Hanks' Balanced Salt Solution with 10% OPTIPREP at $5 \times 10^6$/ml and loaded in a microfluidic device having the channel geometry shown in FIG. 1A, for analysis. Fluorescence was detected using 488 nm excitation, while emission was read at 525 nm and 680 nm.

Figure 4:
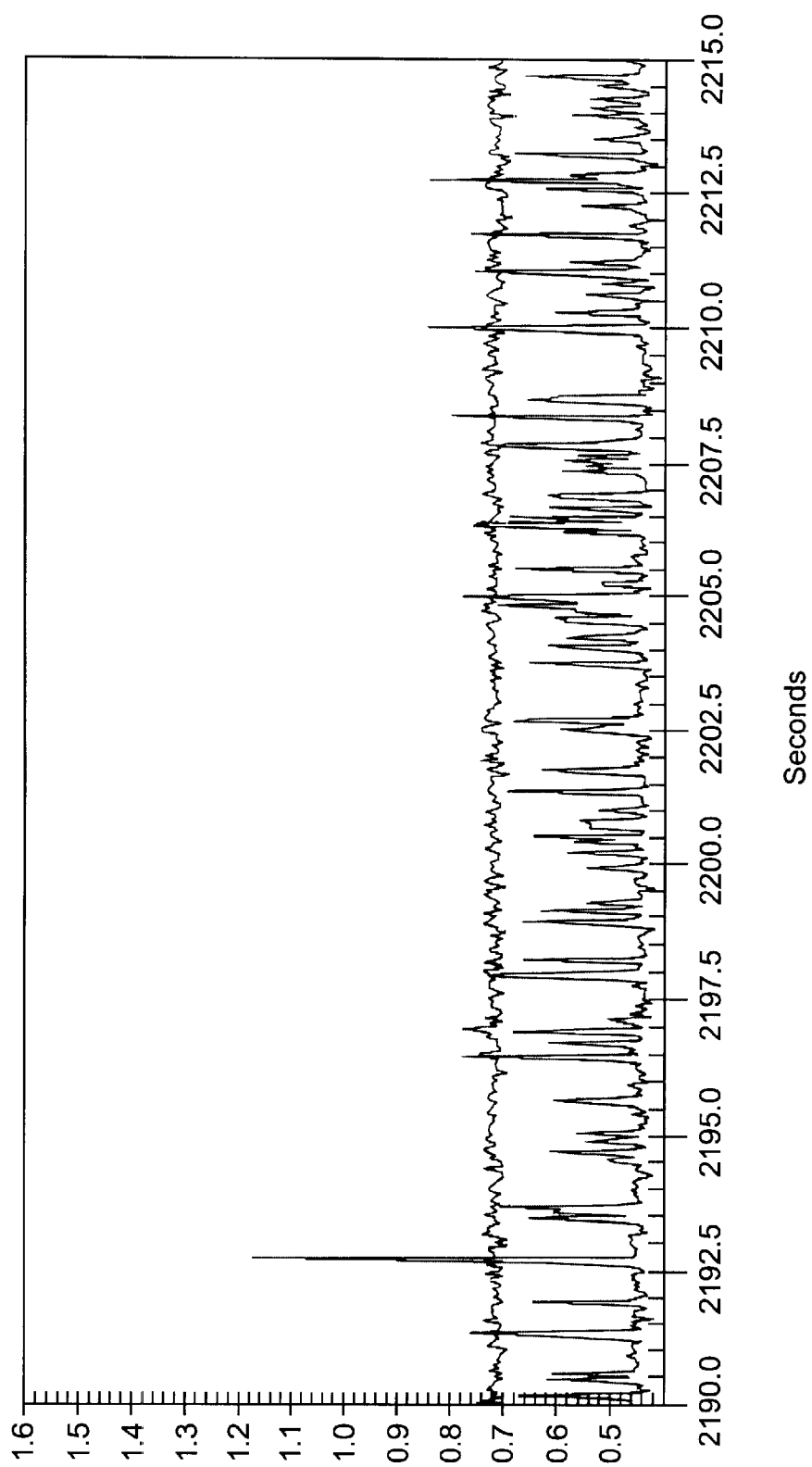
FIG. 4 is a data graph illustrating a control analysis, e.g., U937 cells not treated to induce apoptosis. The bottom line corresponds to the SYTO®-62, which indicates the mere presence of cells, whereas the top line corresponds to the fluorescein end labeled nucleic acids.
Figure 5:
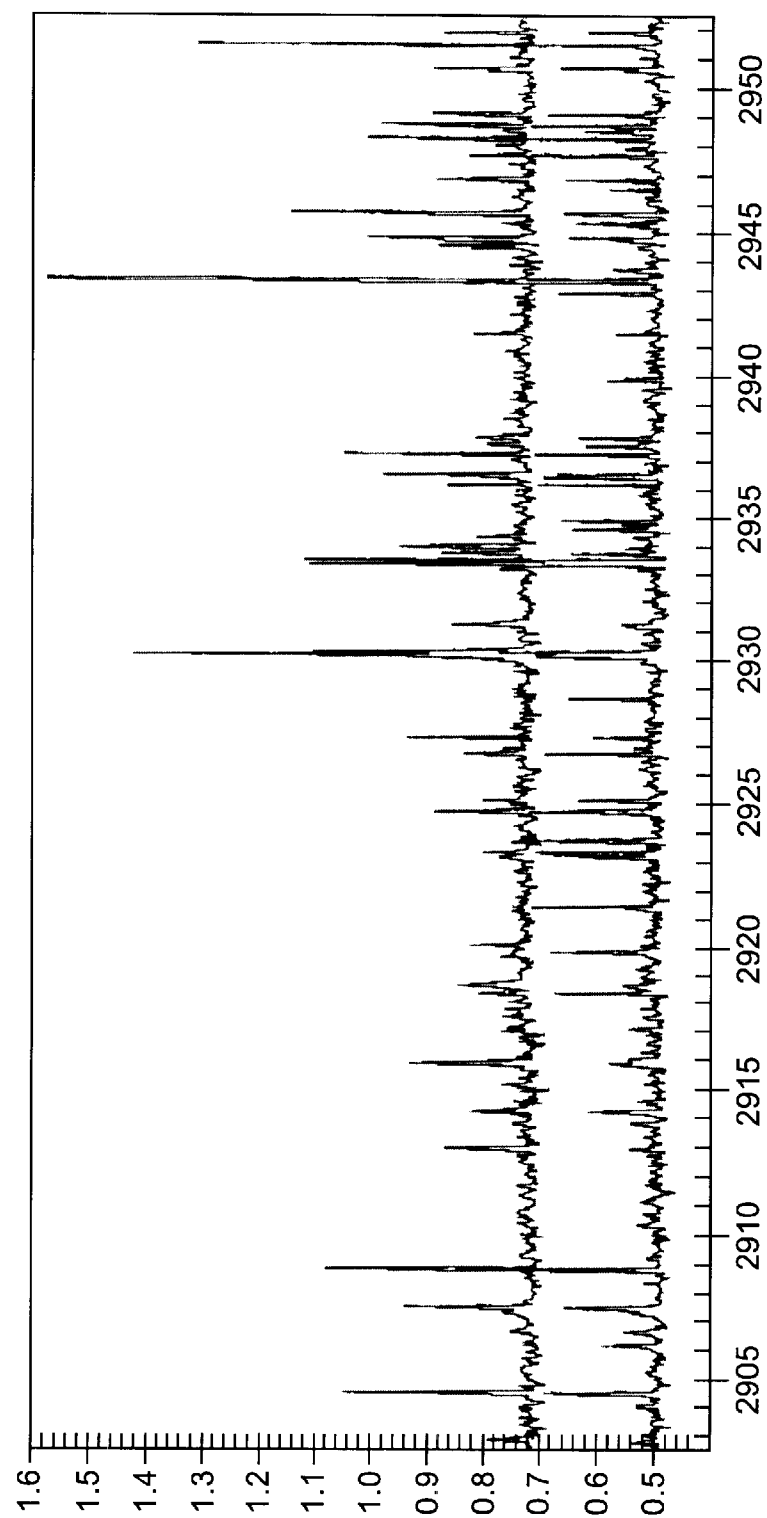
FIG. 5 is a data graph illustrating U937 cells treated with Campthotecin to induce apoptosis. As can be seen, corresponding peaks are seen on both the lower and upper lines, indicating the presence of apoptotic cells.

FIG. 4 illustrates a control analysis, e.g., U937 cells not treated to induce apoptosis. The bottom line corresponds to the SYTO®-62, which indicates the mere presence of cells, whereas the top line corresponds to the fluorescein end labeled nucleic acids. Apoptotic cells would yield a peak on both the upper and lower lines, indicating the presence of an apoptotic cell. As can be seen, there are substantially no discernible peaks in the upper line, indicating a lack of apoptosis in the control. FIG. 5 represents U937 cells treated with Campthotecin to induce apoptosis. As can be seen, corresponding peaks are seen on both the lower and upper lines, indicating the presence of apoptotic cells.

In an Annexin-V assay, change in the outer membrane of apoptotic cells is detected. A membrane component, phosphatidylserine (PS) is translocated to the outer layer. Annexin-V binds to PS and is conjugated to biotin to allow secondary reactions to fluorescently labeled Streptavidin for detection. U937 cells were treated with Campthotecin to induce apoptosis. The cells were harvested and washed in phosphate buffered saline (PBS). Cells were incubated with Annexin-V-Biotin (Boehringer Mannheim) in HEPES buffer, and then incubated with 5 µg streptavidin-Cy5 (Amersham) and 1 mM of Calcein-AM dye in HEPES buffer. The HEPES buffer solution contained 10 mM HEPES, pH 7.4; 140 mM NaCl; and a 5 mM $CaCl_2$. The cells were washed and resuspended in HEPES buffer with 8.5% sucrose and loaded in a microfluidic device for analysis. Fluorescence was detected using excitation at 488 nm and 635 nm, and emission was read at 525 nm and 682 nm.

Figure 6:
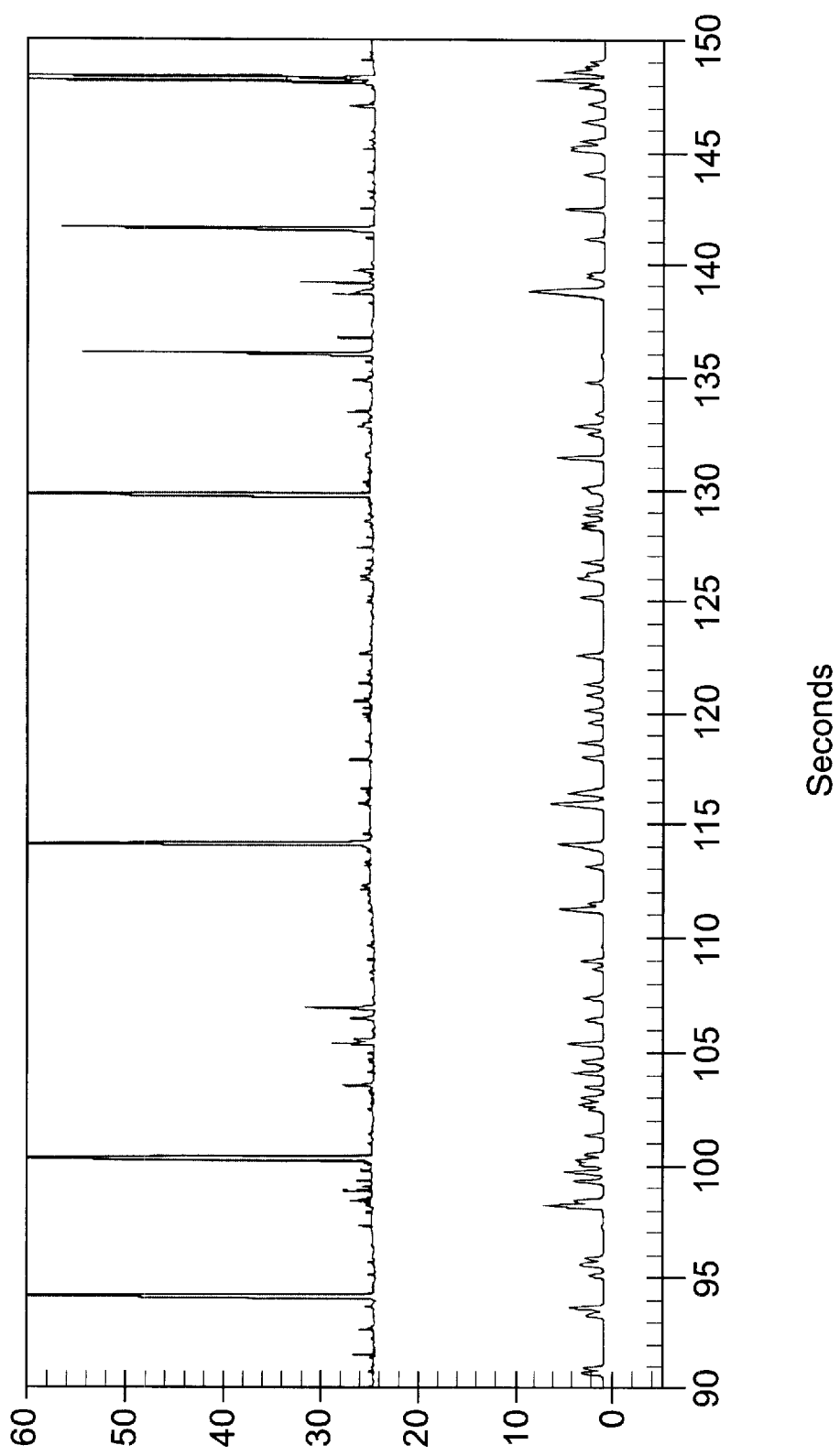
FIG. 6 is a data graph illustrating an analysis of U937 cells that were not treated to induce apoptosis. In this case, the bottom line indicates live cell count (Calcein), while the top line indicates the presence of apoptotic cells (Annexin-V-Cy5). As can be seen, a few apoptotic cells are present within the control experiment.
Figure 7:
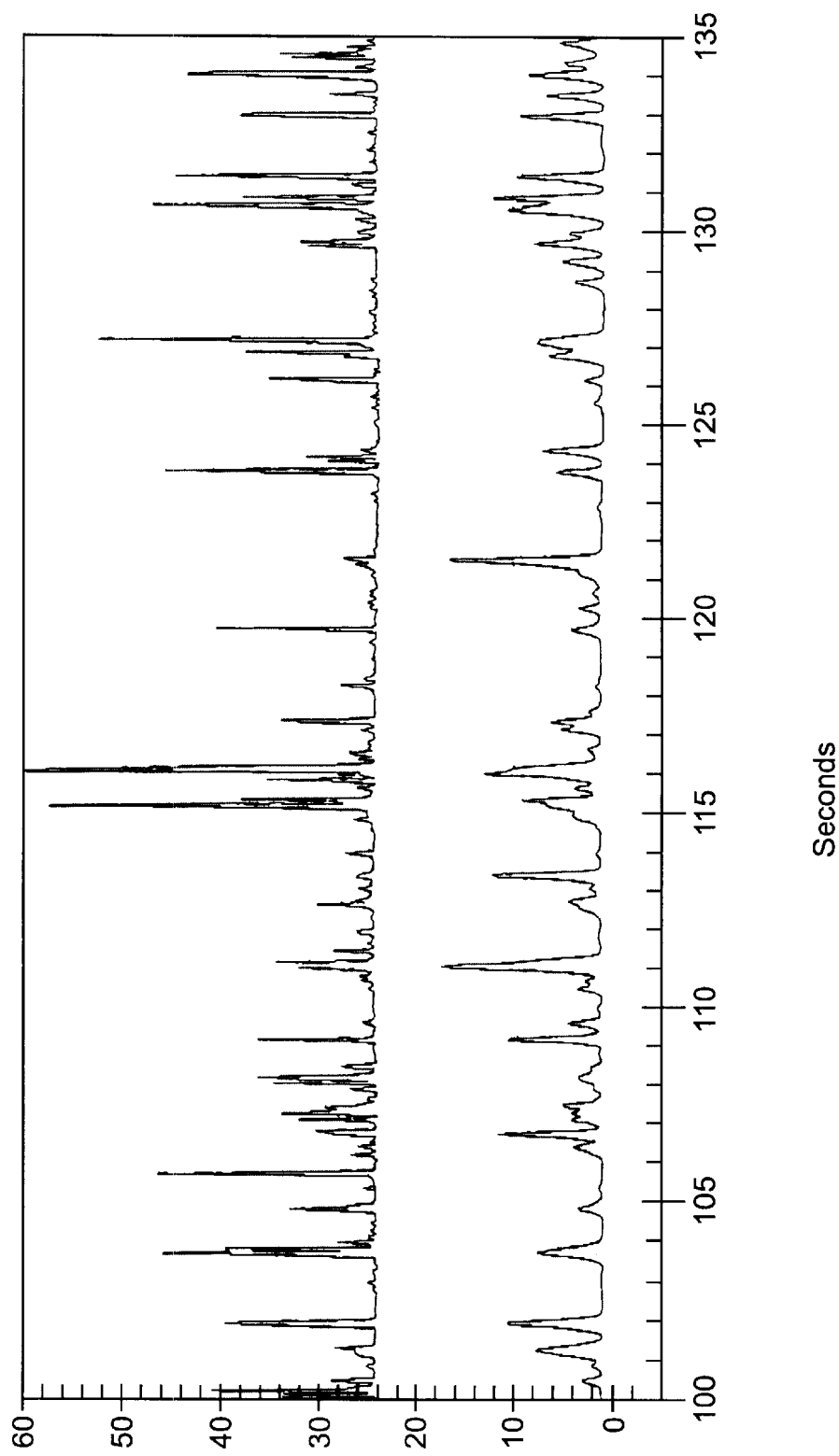
FIG. 7 is a data graph showing an analysis of U937 cells treated with Campthotecin to induce apoptosis. The top trace includes a much greater number of peaks representing apoptotic cells, and particularly as a percentage of total cells in the analysis, e.g., as compared to the lower line.

FIG. 6 indicates analysis of U937 cells that were not treated to induce apoptosis. In this case, the bottom line indicates live cell count (Calcein), while the top line indicates the presence of apoptotic cells (Annexin-V-Cy5). As can be seen, a few apoptotic cells are present within the control experiment. FIG. 7, on the other hand, shows an analysis of the same cells treated with Campthotecin to induce apoptosis. As can be seen, the top trace includes a much greater number of peaks representing apoptotic cells, and particularly as a percentage of total cells in the analysis, e.g., as compared to the lower line.

Figure 8:
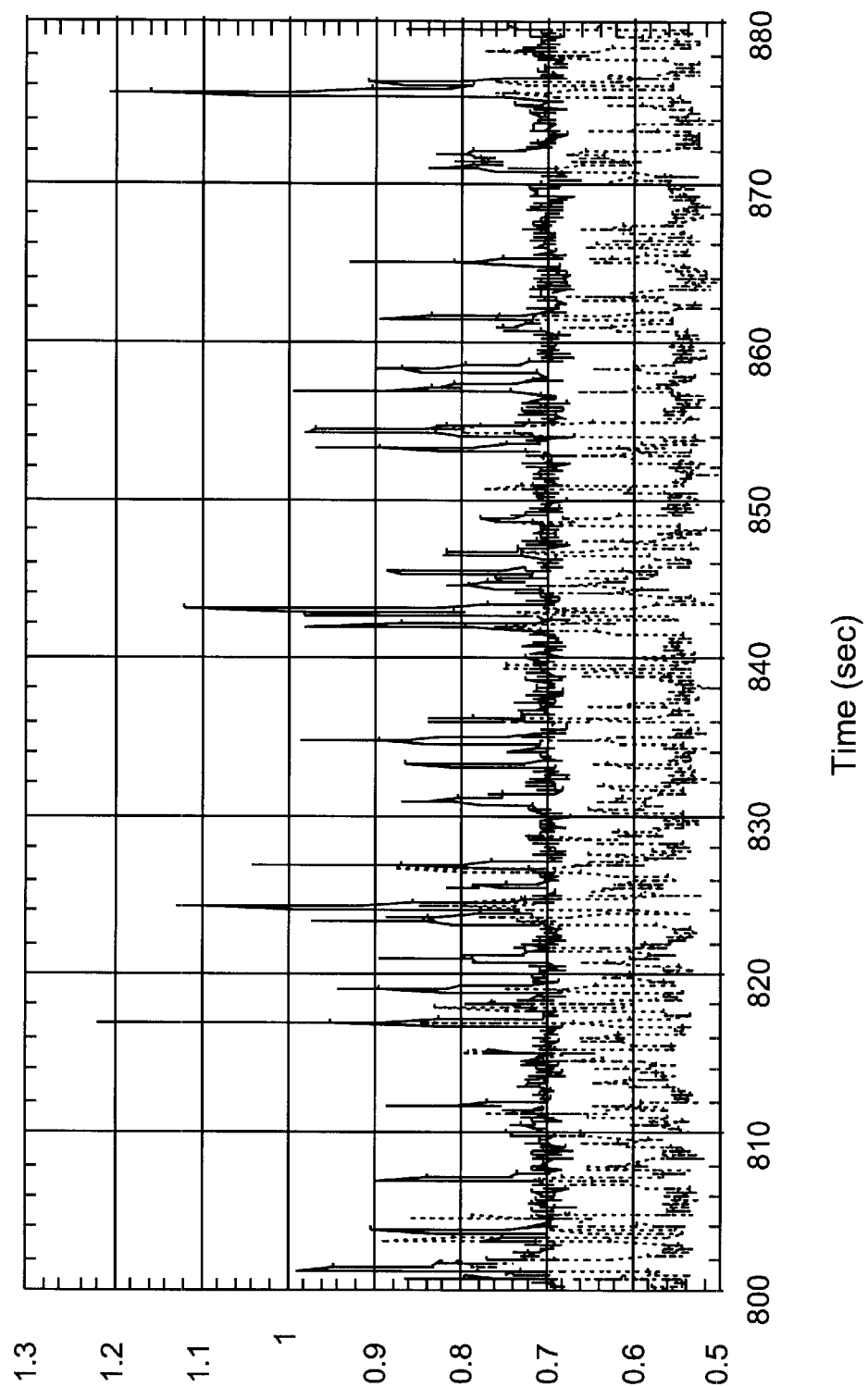
FIG. 8 is a data graph showing results from a TUNEL assay with HL-60 cells treated with Campthotecin for 6 hours to induce apoptosis. The bottom line traces the total cell count. The top line traces apoptotic cells labeled at DNA damage points. In this case, almost all cells had sustained apoptotic DNA damage.

FIG. 8 shows results from a TUNEL assay with HL-60 cells treated with Campthotecin for 6 hours to induce apoptosis. The bottom line traces the total cell count. The top line traces apoptotic cells labeled at DNA damage points. In this case, almost all cells had sustained apoptotic DNA damage.

Figure 9:
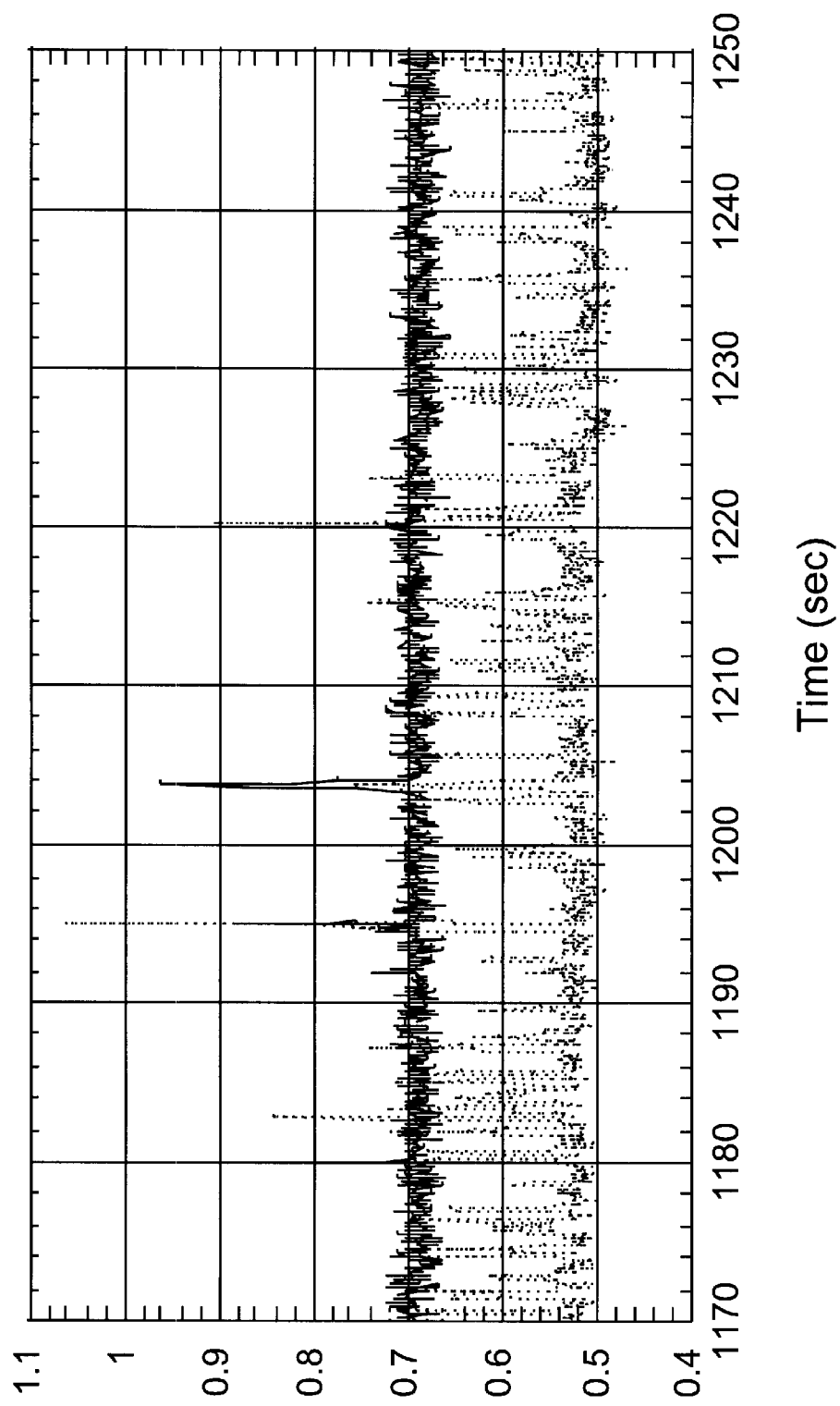
FIG. 9 is a data graph showing results from a TUNEL assay. HL-60 cells (not treated for apoptosis) were used as control cells. The bottom trace is for SYTO®-62 indicating total cell count. The top trace is for fluorescein labeled nucleotide which signifies the presence of apoptosis related DNA damage.

FIG. 9 shows results from a TUNEL assay. HL-60 cells (not treated for apoptosis) were used as control cells. The bottom trace is for SYTO®-62 indicating total cell count. The top trace is for Fluorescein labeled nucleotide which signifies the presence of apoptosis related DNA damage.

Figure 10:
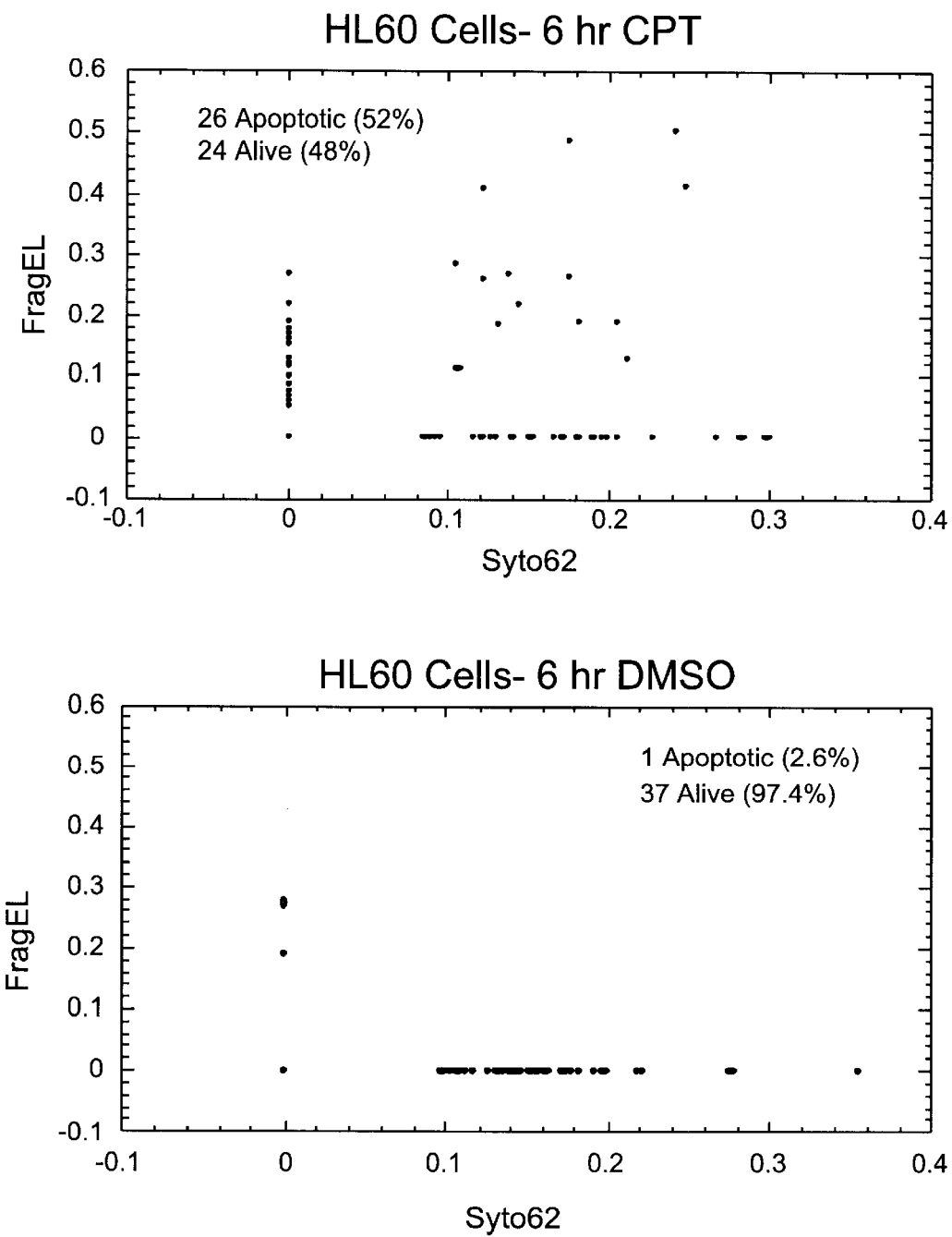
FIG. 10 is a data graph showing results from TUNEL assays from FIGS. 8 and 9 analyzed using appropriate software. Data is presented as scatter plot format in FIG. 10.
Figure 11:
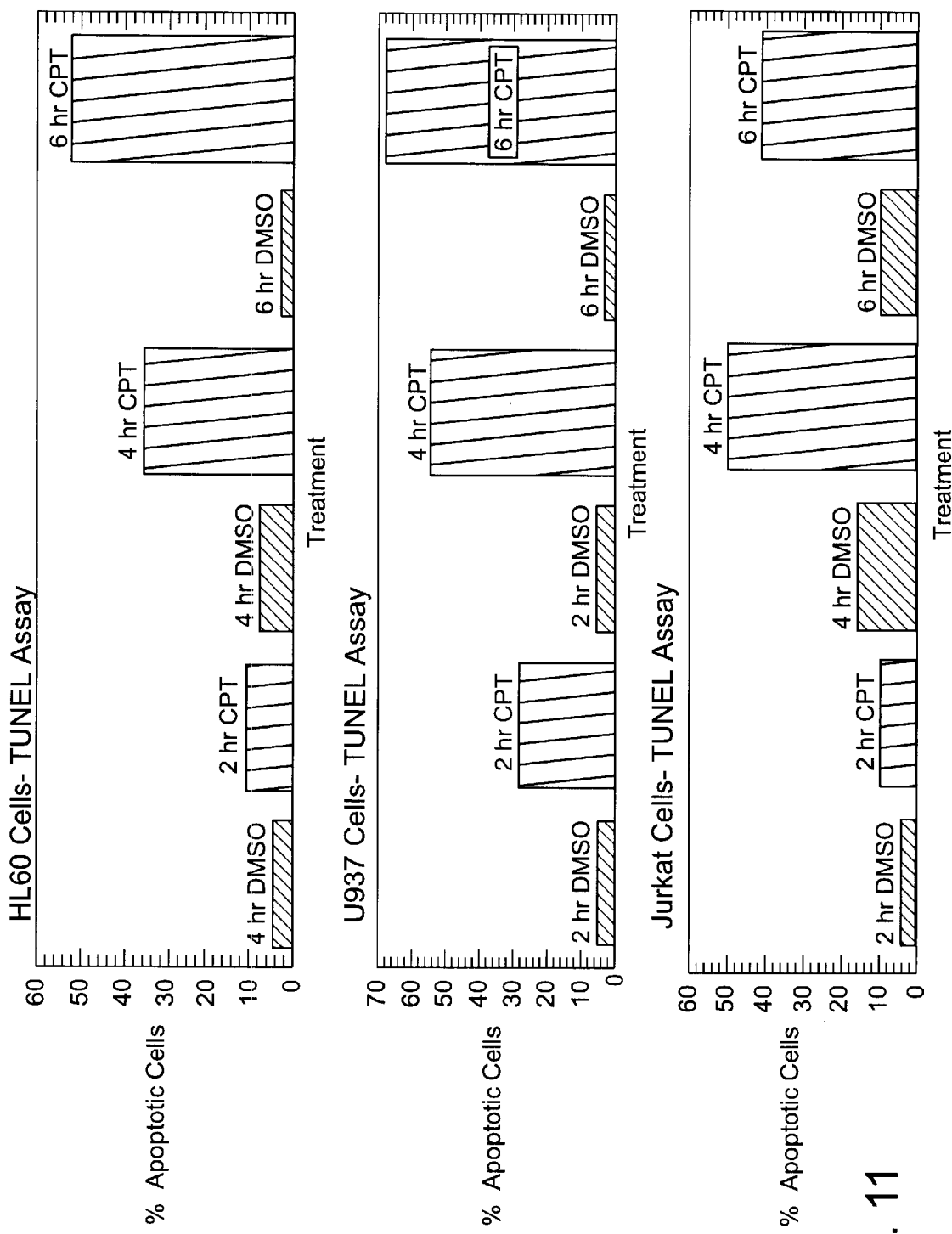
FIG. 11 is a data graph showing results from TUNEL assays from data represented in bar graph format. Additional data for different time points and two other cell lines is included.

FIGS. 10 and 11 shows results from TUNEL assays from FIGS. 8 and 9 analyzed using appropriate software. Data is presented as scatter plot format in FIG. 10. In FIG. 11, data is represented in bar graph format. Additional data for different time points and two other cell lines is included.

Figure 12:
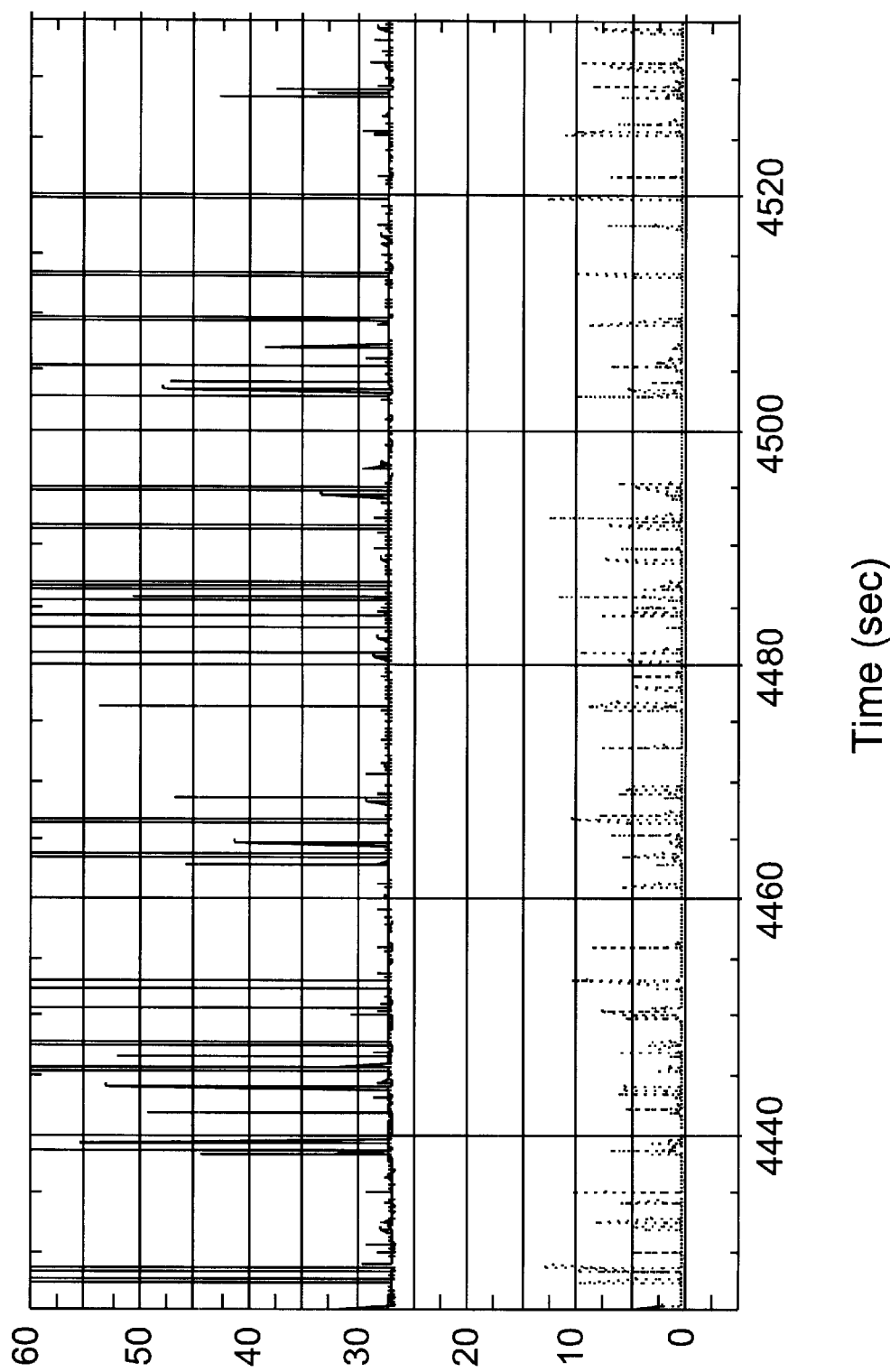
FIG. 12 is a data graph showing an Annexin-V assay. HL60 cells were treated with Campothotecin for four hours to induce apoptosis. The bottom trace indicates live cell count (Calcein). The top trace indicates Annexin-V-Cy5 labeling. Cells labeled only for Calcein are live cells and not apoptotic. In this case, almost all cells are apoptotic.

FIG. 12 shows and Annexin-V assay. HL60 cells were treated with Campothotecin for four hours to induce apoptosis. The bottom trace indicates live cell count (Calcein). The top trace indicates Annexin-V-Cy5 labeling. Cells labeled only for Calcein are live cells and not apoptotic. In this case, almost all cells are apoptotic.

Figure 13:
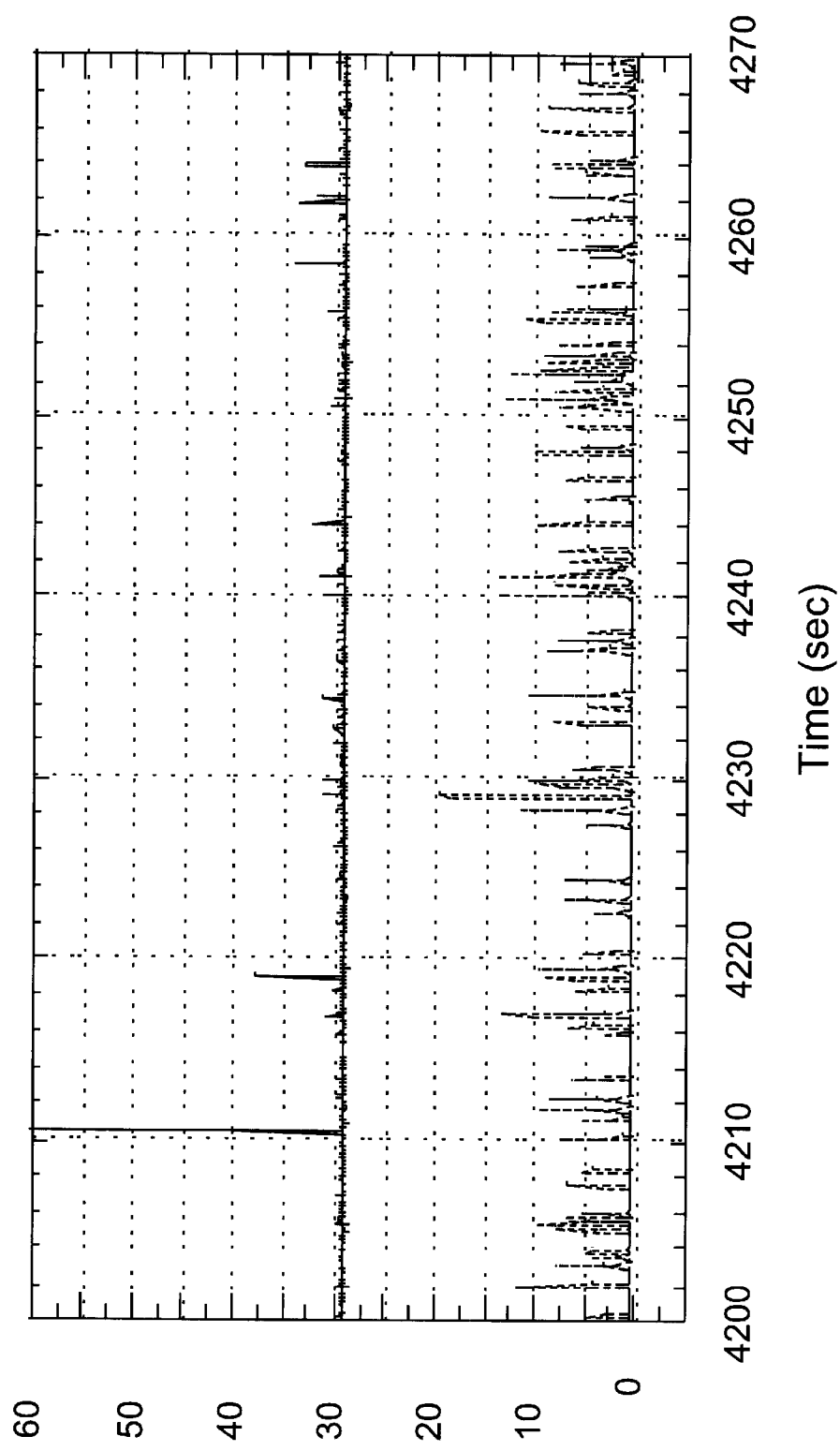
FIG. 13 is a data graph showing an Annexin-V assay. HL-60 cells (not treated for apoptosis) are control cells. The bottom trace indicates live cell count. The top trace indicates Annexin-V-Cy5 labeling. Cells labeled with both dyes are apoptotic. Cells labeled only for Annexin-Cy5 are dead cells. In this case, only a few cells were apoptotic.

FIG. 13 shows an Annexin-V assay. HL-60 cells (not treated for apoptosis) are control cells. The bottom trace indicates live cell count. The top trace indicates Annexin-V-Cy5 labeling. Cells labeled with both dyes are apoptotic. Cells labeled only for Annexin-CY5 are dead cells. In this case, only a few cells were apoptotic.

Figure 14:
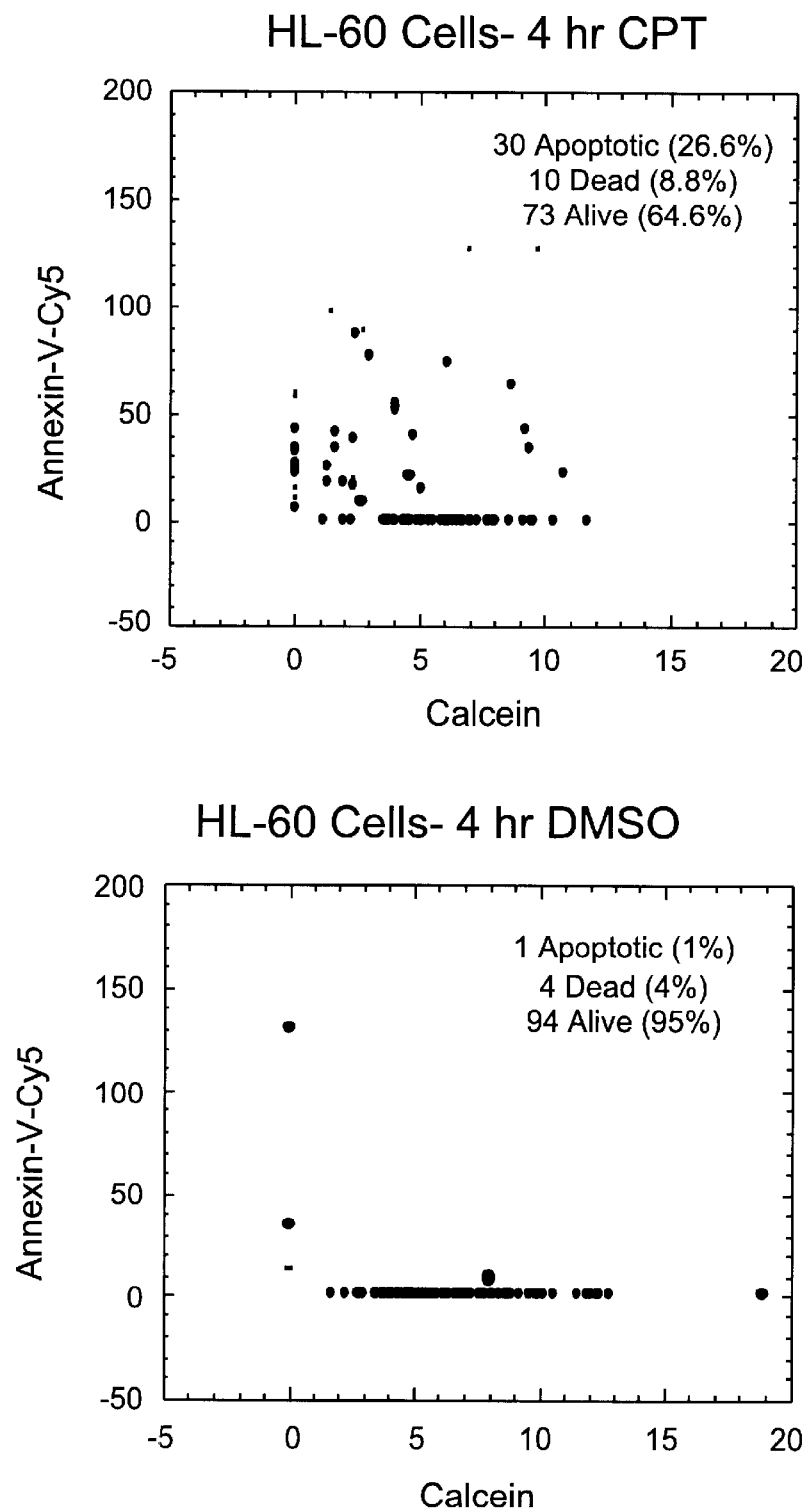
FIG. 14 is a data graph showing data analysis of FIGS. 12 and 13. Data is presented in scatter plot format in FIG. 14.
Figure 15:
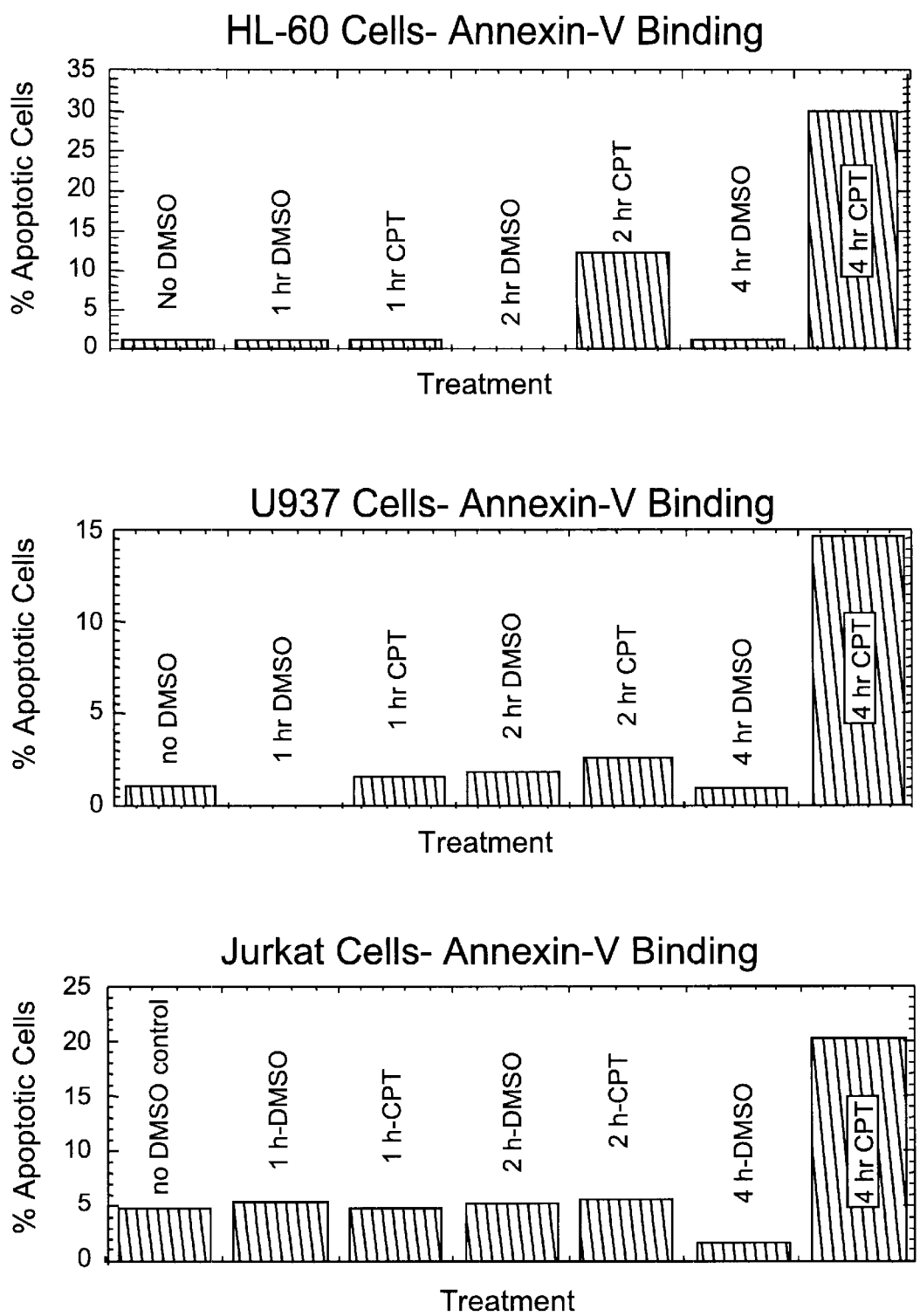
FIG. 15 is a data graph showing data represented in bar graph format.

FIGS. 14 and 15 show data analysis of FIGS. 12 and 13. Data is presented in scatter plot format in FIG. 14. In FIG. 15, data is represented in bar graph format. Additional data for different time points and two other cell lines is included.

FLUORESCENCE POPULATION AND CONCENTRATION EXPERIMENTS

Figure 17:
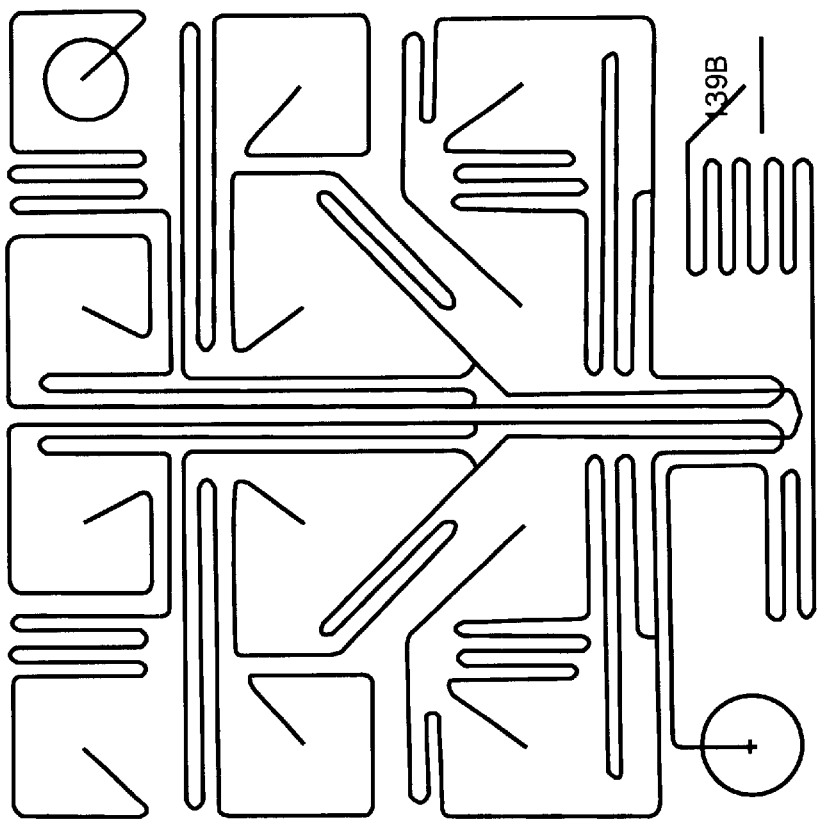
FIG. 17 depicts a chip design used to conduct fluorescence population focusing experiments.

FIG. 17 depicts a chip employing a channel geometry that was used to conduct fluorescence population experiments to confirm the feasibility of the device as a microfluidic flow cytometer. The experiment entailed comparing microfluidic hydrodynamic focusing data obtained by flowing fluorescently-labeled calibration beads (Quantum 26 Fluorescein Microbeads Standards B-111698 from Flow Cytometry Standards Corp.) through the microfluidic flow cytometer (both focused and unfocused) with data provided in a certificate of calibration that accompanied the beads. Flow Cytometry Standards Corp. obtained the calibration data by flowing the same type of bead through a traditional flow cytometer.

Figure 18:
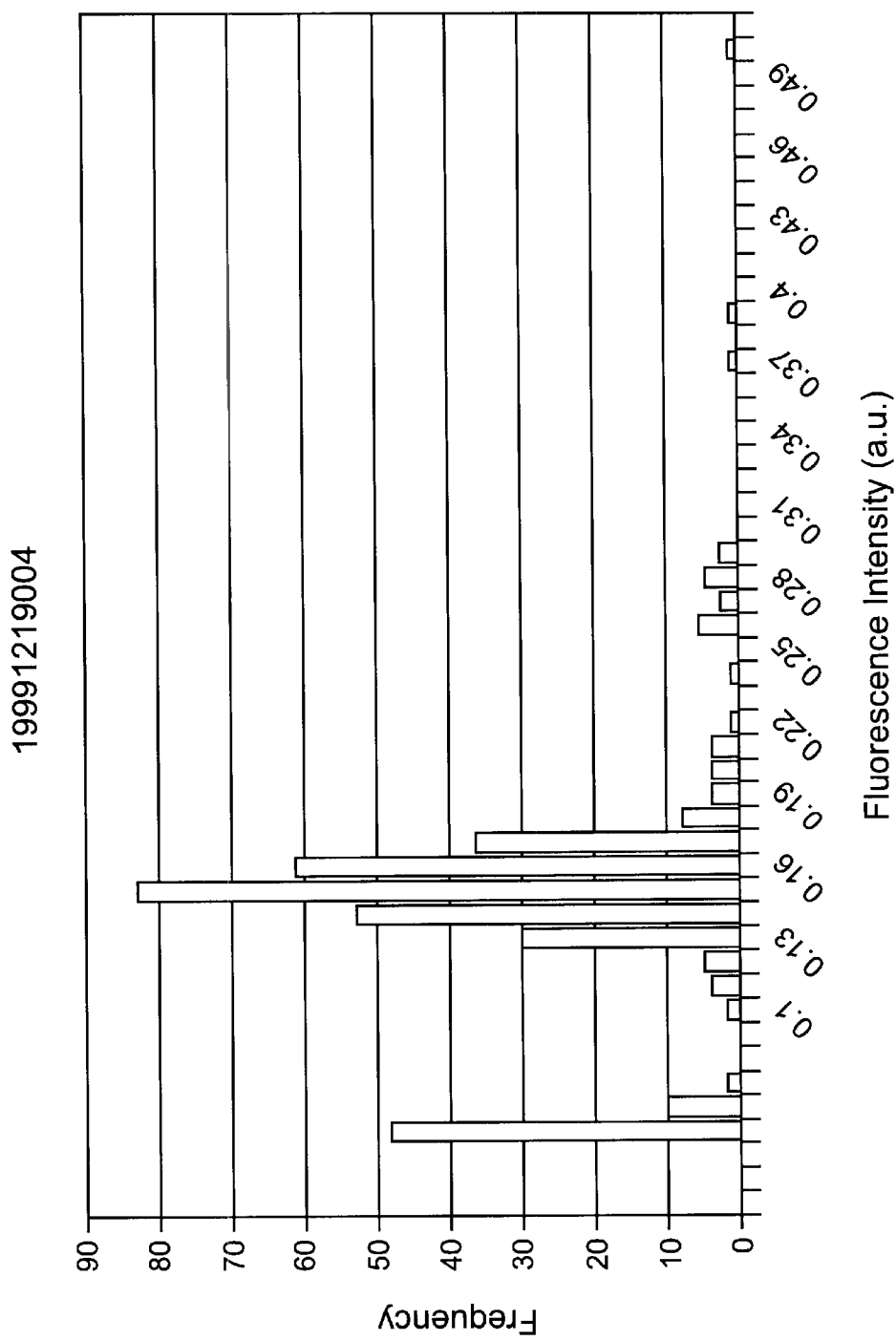
FIG. 18 is a histogram showing the distribution of results obtained in a fluorescence intensity population experiment conducted utilizing hydrodynamic focusing.
Figure 19:
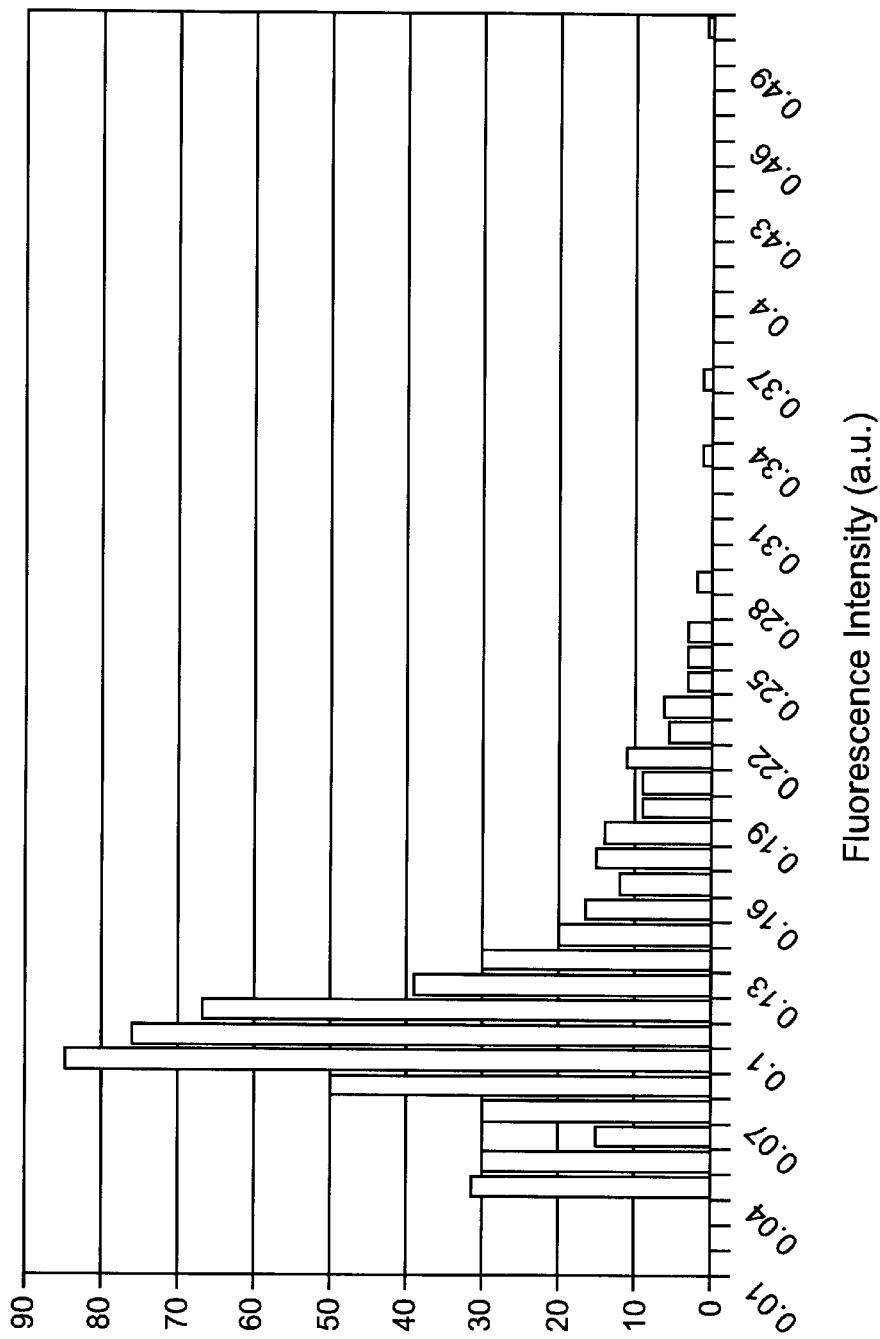
FIGS. 19 and 20 are histograms showing the distribution of results obtained in fluorescence intensity population experiments conducted in the absence of hydrodynamic focusing.
Figure 20:
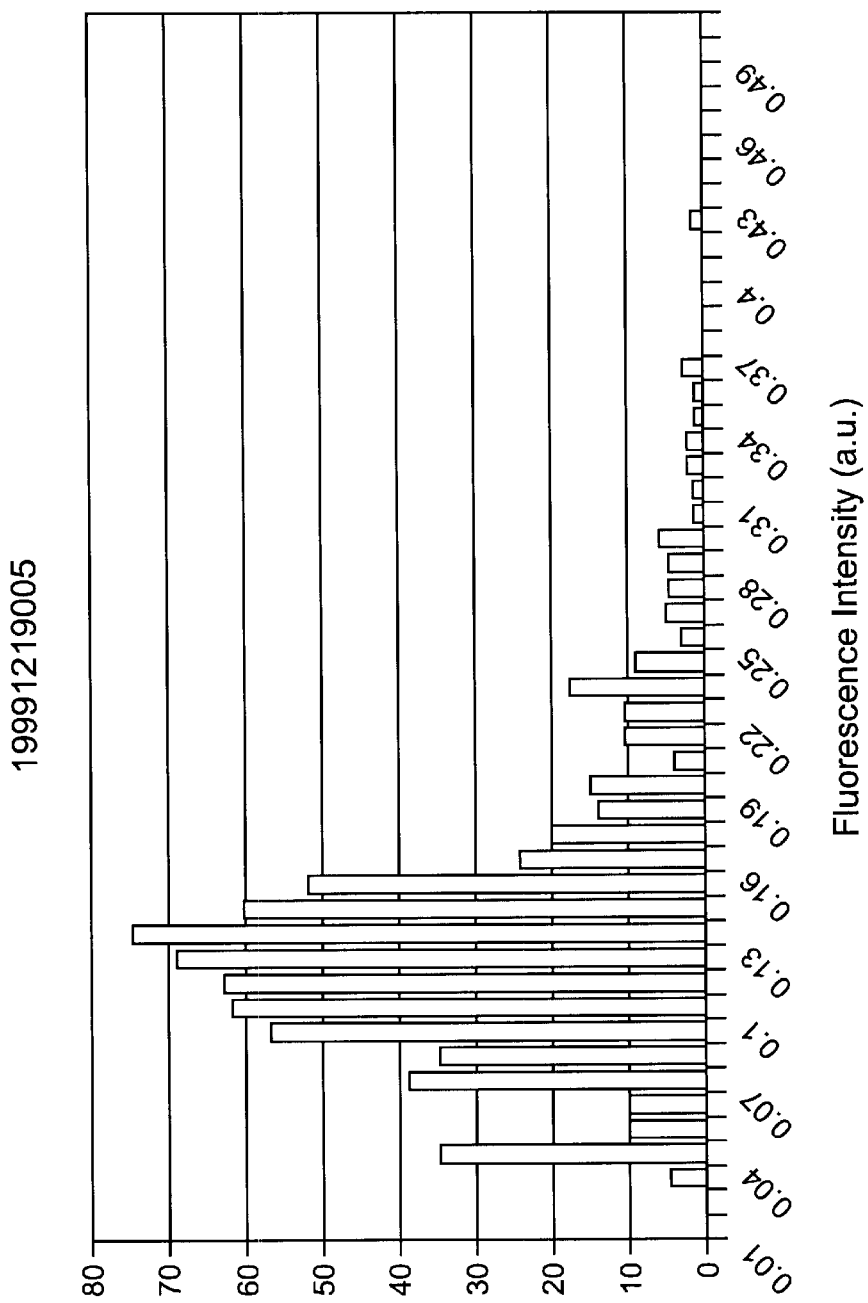

FIG. 18 is a histogram showing the distribution of results obtained in the fluorescence intensity population experiment conducted utilizing hydrodynamic focusing in the microfluidic flow cytometer. FIGS. 19 and 20 are histograms showing the distribution of results obtained in the fluorescence intensity population experiment conducted, in the same microfluidic flow cytometer, in the absence of hydrodynamic focusing. As shown, the focused beads resolve into a more uniform fluorescence intensity population than the unfocused beads which are more widely distributed. Furthermore, the focused beads are comparable to results achievable using traditional flow cytometers, which typically include a coefficient of variation (%CV) of about 6%, according to the calibration data provided by Flow Cytometry Standards Corp. The calculated %CV for the focused beads in the microfluidic system was about 6.8%, whereas that calculated for the unfocused beads was only about 28.8%. In general, an acceptable %CV is less than 15%, which further demonstrates the feasibility of the device, e.g., as a flow cytometer.

Figure 25A:
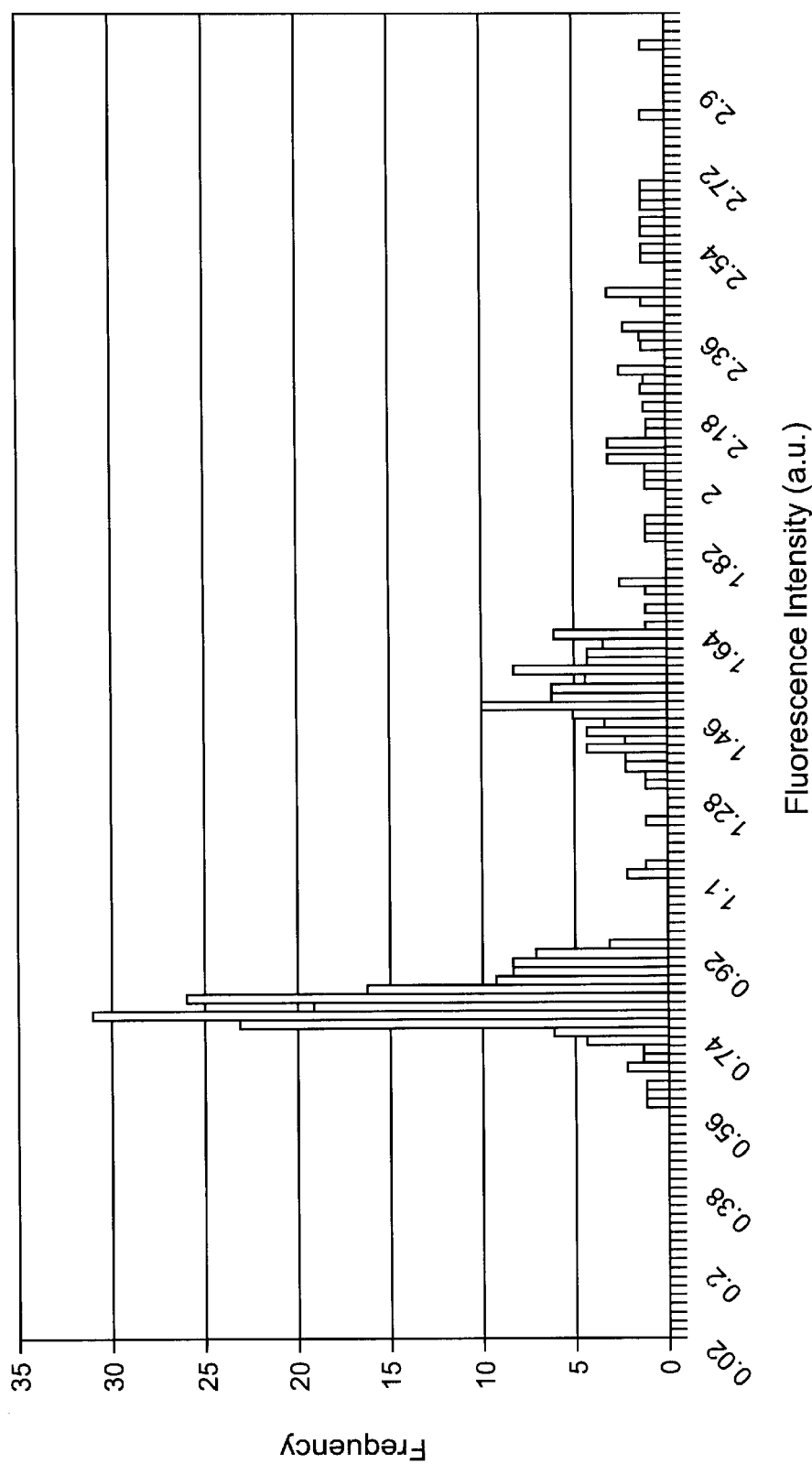
FIGS. 25A, B, and C are histograms showing the distribution of results obtained in resolution experiments using various microbead concentrations.
Figure 25B:
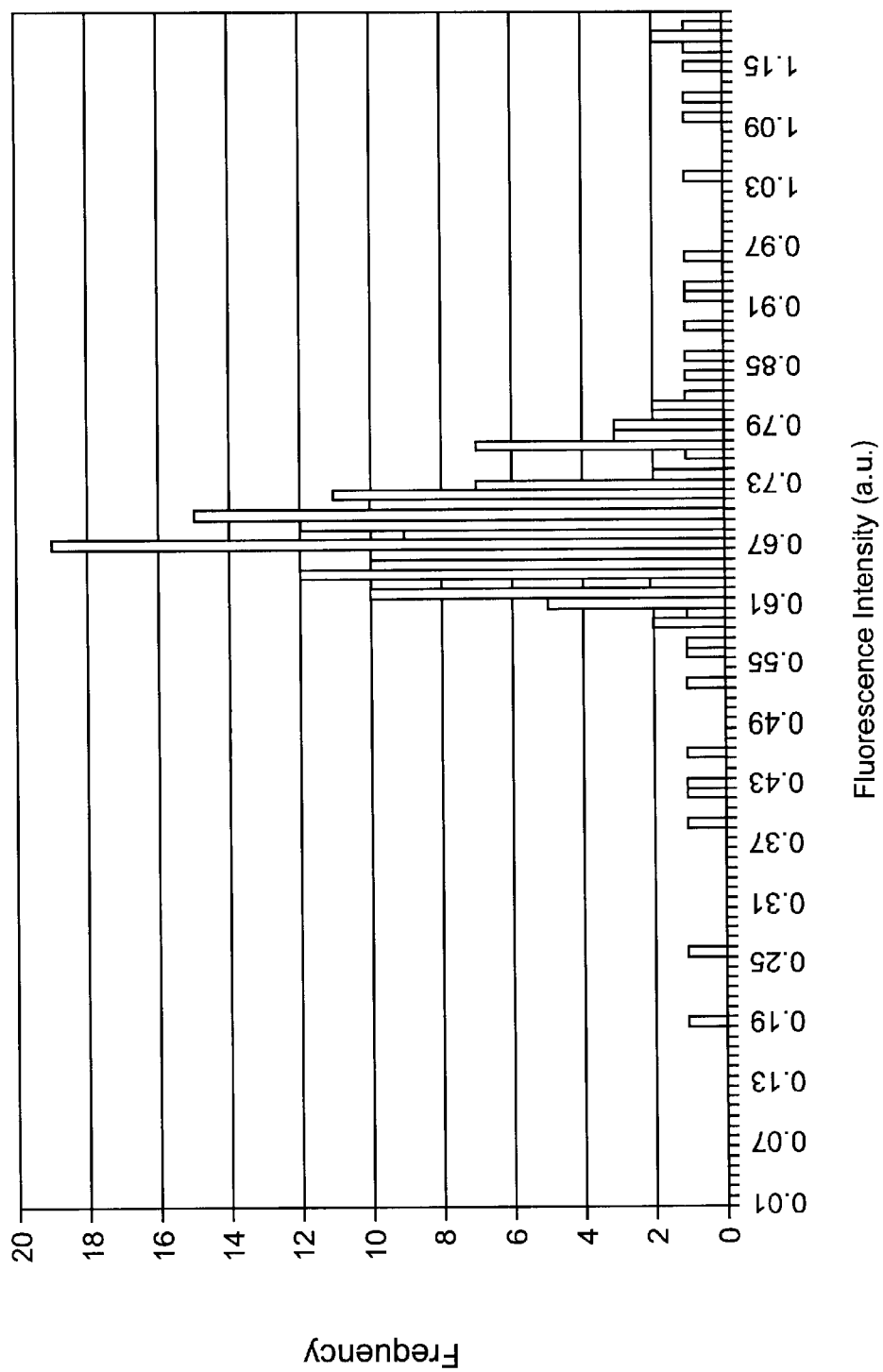
Figure 25C:
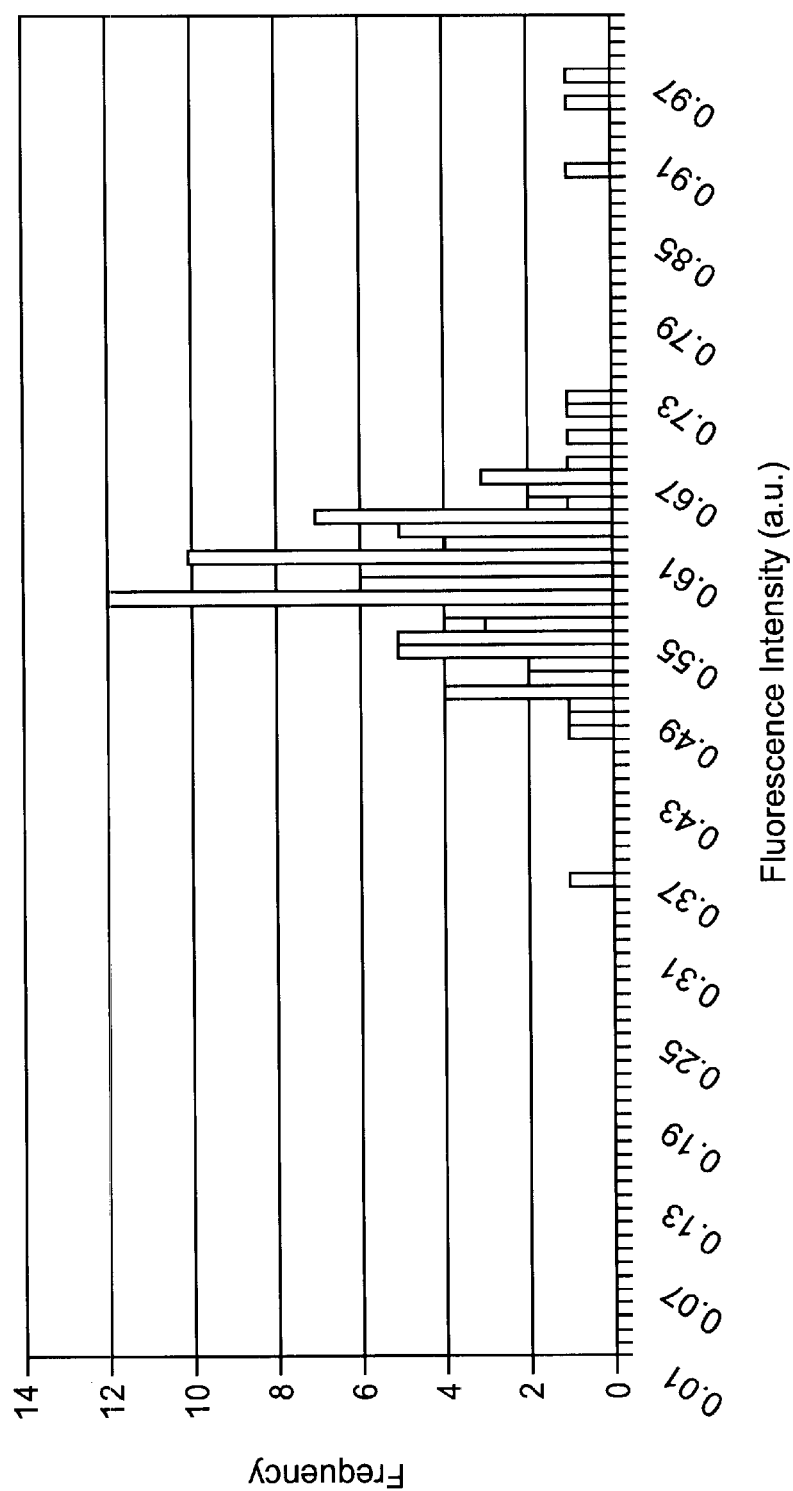
Figure 26:
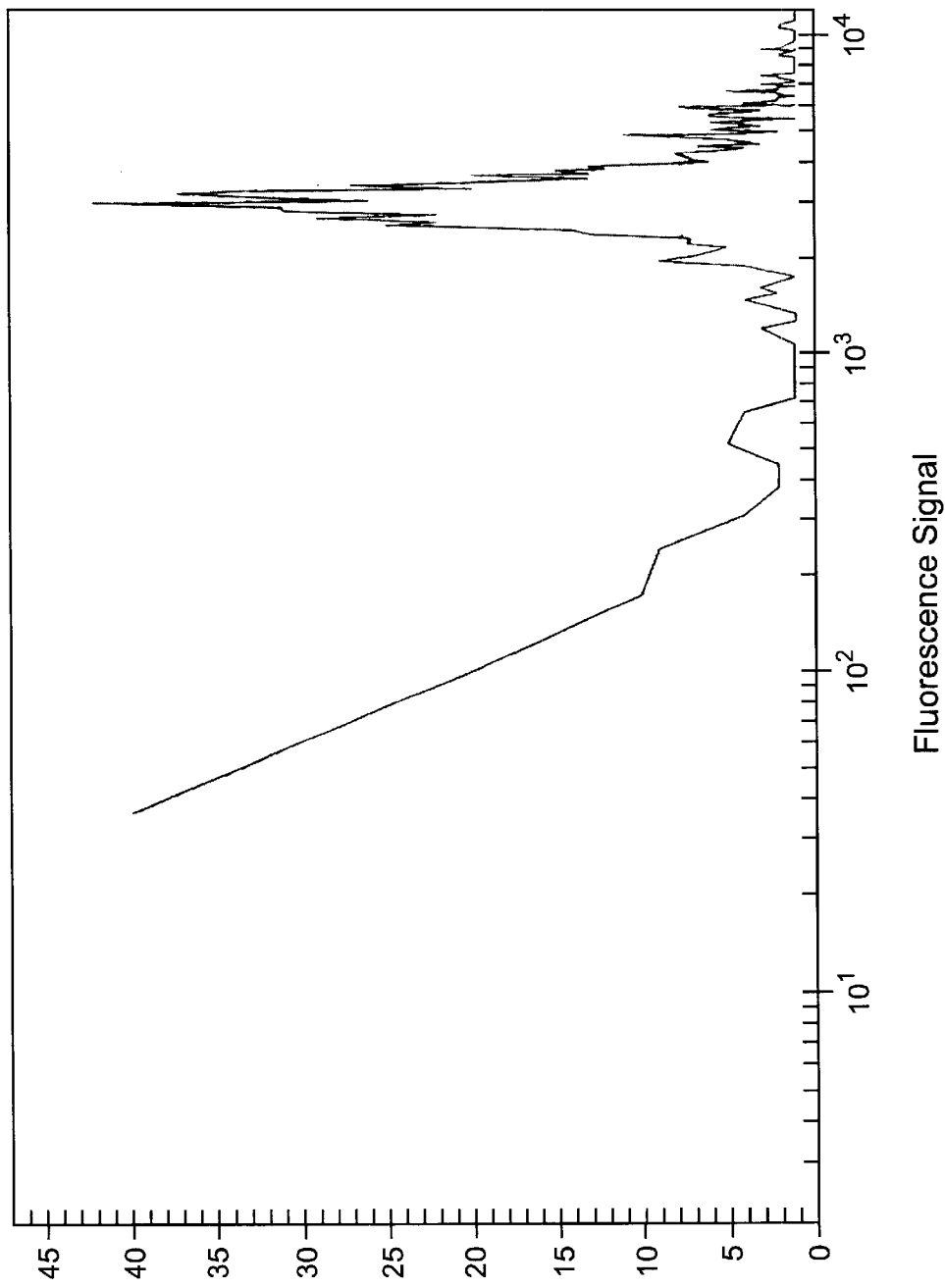
FIG. 26 is a histogram showing the distribution of results obtained in a resolution experiment using viable cells stained with an intercalating dye.

FIGS. 25A, B, and C are histograms showing the distribution of results obtained in resolution experiments using various microbead to buffer concentrations, namely, 1:1, 1:3, and 1:7, respectively. The experiments were conducted using an Agilent bioanalyzer microfluidic system to determine whether microbead doublet populations could be resolved. As shown, even at the highest microbead concentration, where the largest population of doublets was expected, significant resolution of the two populations was observed with a %CV of about 6.7%. (FIG. 25A). Similar %CVs were obtained at the two other concentrations. To further confirm the capabilities of the devices and methods of the present invention an additional resolution experiment was conducted using viable THP-1 cells stained with SYTO®-62 intercalating dye. As shown in FIG. 26, significant resolution was achieved with a %CV comparable to those obtained using traditional flow cytometric devices.

FLOW SIMULATIONS

Figure 27:
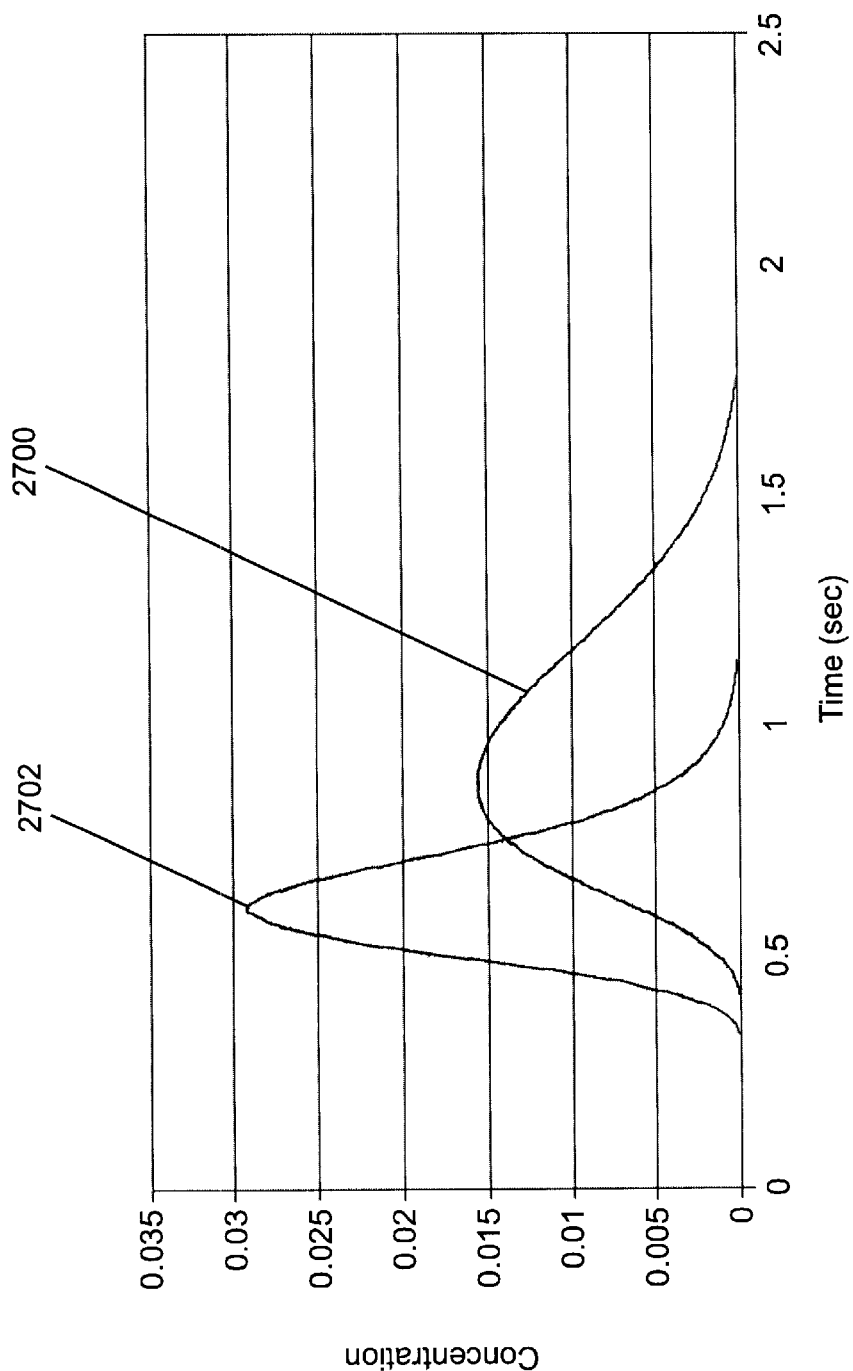
FIG. 27 is a data graph showing variations of sample concentrations with time for simulated flows through an asymmetric and a symmetric microchannel intersection.

FIG. 27 is a data graph showing variations of sample concentrations with time for simulated flows through an asymmetric and a symmetric microchannel intersection. The flow simulations depicted in FIG. 27 where performed using the Fluid Dynamics Analysis Package (FIDAP™) software from Fluent, Inc., Lebanon, N.H., (www.fluent.com). As shown, the ordinate represents concentration, whereas the abscissa represents time in seconds. Trace 2700 represents the result of the simulation achieved for the asymmetric microchannel configuration modeled in FIG. 28. Trace 2702 represents the result of the flow simulation obtained for the symmetric microchannel configuration modeled in FIG. 29.

Figure 28:
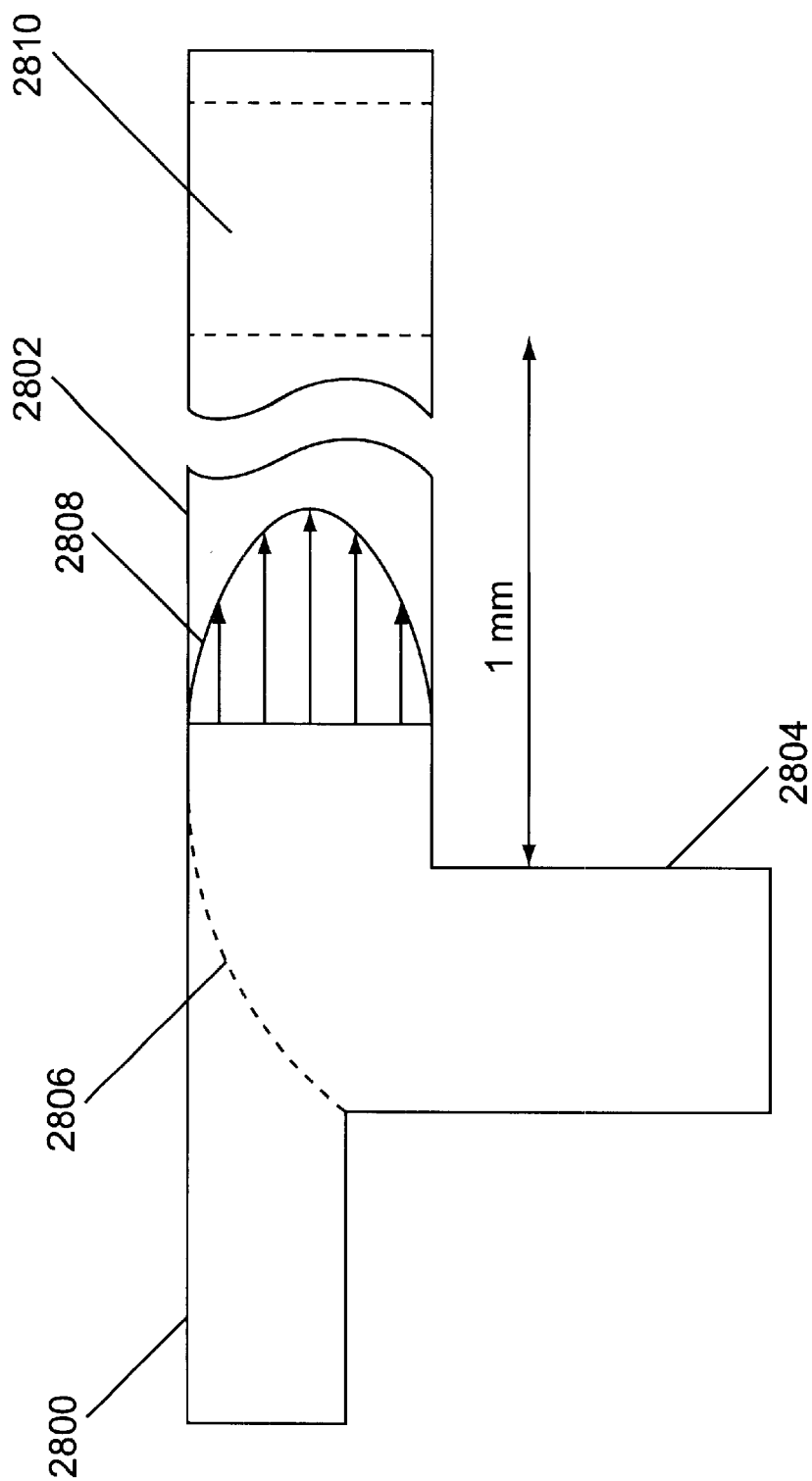
FIG. 28 schematically depicts fluid flow into a sample mixing and detecting region from an asymmetric microchannel intersection modeled for the simulation depicted in FIG. 27.

FIG. 28 schematically shows fluid flow into a sample mixing and detecting region from an asymmetric microchannel intersection modeled for the simulation depicted in FIG. 27. As shown, discrete sample volume inlet microchannel 2800 intersects with dilution/mixing microchannel 2802 approximately perpendicular to the intersection of focusing microchannel 2804 with dilution/mixing microchannel 2802. In the flow simulation, discrete sample volume inlet microchannel 2800 was modeled with a depth of 4 $\mu$m from which a discrete sample volume (i.e., a slug) of DMSO was flowed into dilution/mixing microchannel 2802, which was modeled with a depth of 12 $\mu$m and a width of 49 $\mu$m. Focusing microchannel 2804 was modeled with a depth of 12 $\mu$m and a width of 33 $\mu$m from which water was flowed. During the flow simulation, modeled fluid streamline 2806 (i.e., water) from focusing microchannel 2804, flowed under pressure, pinched modeled DMSO slugs flowed from discrete sample volume inlet microchannel 2800 towards the wall of dilution/mixing microchannel 2802 which opposes focusing microchannel 2804 where the fluid velocity is low relative to the fluid velocity in the center of the dilution/mixing microchannel 2802. This is further depicted by velocity profile 2808 which illustrates the parabolic nature of pressure-based flow. As further shown, detector region 2810 was modeled as being 1 mm downstream from the intersection of focusing microchannel 2804.

Figure 29:
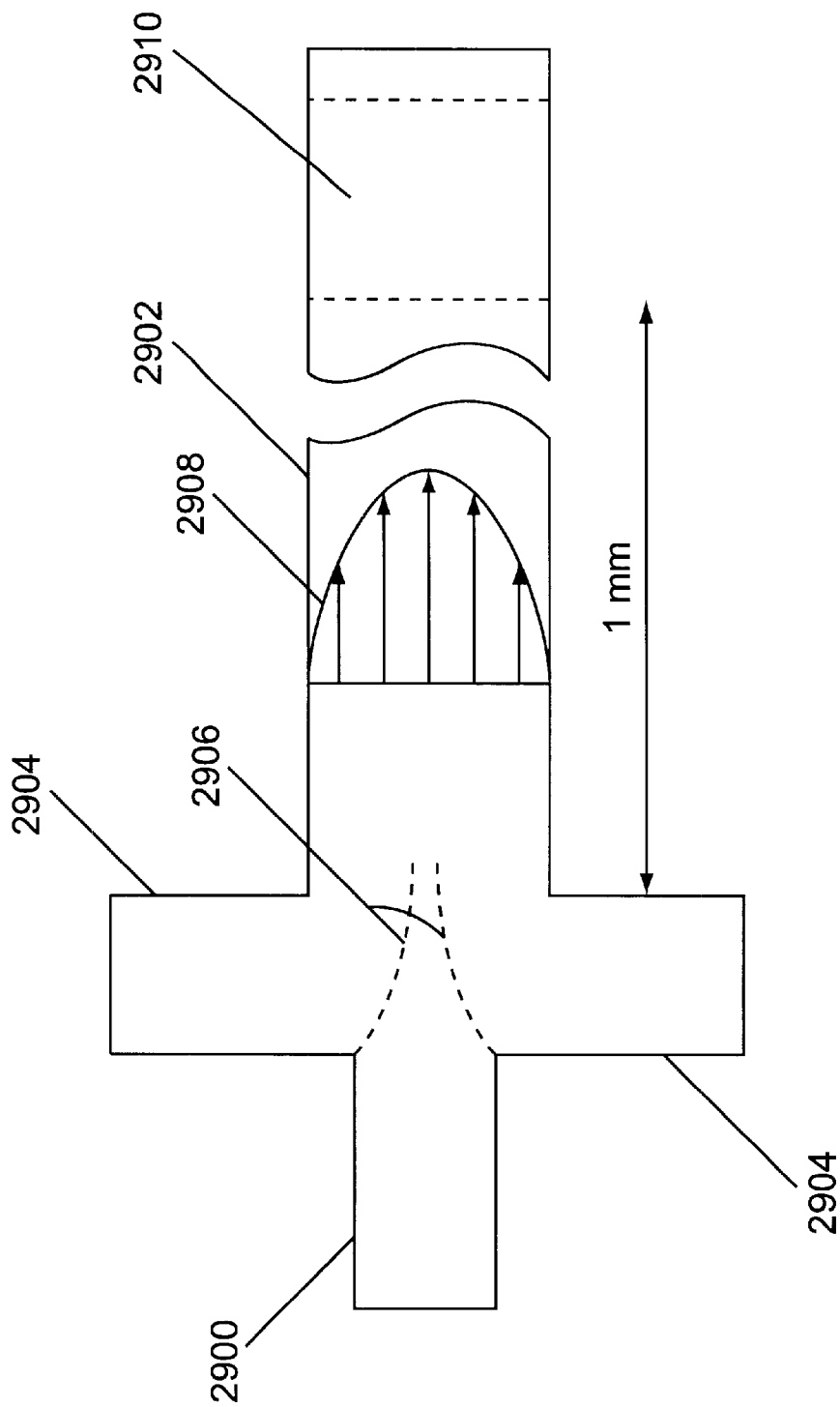
FIG. 29 schematically depicts fluid flow into a sample mixing and detecting region from a symmetric microchannel intersection modeled for the simulation depicted in FIG. 27.

FIG. 29 schematically depicts fluid flow into a sample mixing and detecting region from a symmetric microchannel intersection modeled for the simulation depicted in FIG. 27. As shown, discrete sample volume inlet microchannel 2900 intersects with dilution/mixing microchannel 2902 approximately perpendicular to the intersection of opposed focusing microchannels 2904 with dilution/mixing microchannel 2902. In the flow simulation, modeled focusing fluid streamlines 2906 (i.e., water) flowed under pressure from opposed focusing microchannels 2904 pinched modeled DMSO slugs flowed from discrete sample volume inlet microchannel 2900 proximal to the center of dilution/mixing microchannel 2902, where the fluid velocity was highest. This is further depicted by velocity profile 2908. Similar to the asymmetric intersection schematically depicted in FIG. 28, detector region 2910 was modeled as being 1 mm downstream from the intersection of opposed focusing microchannels 2904.

The results of the flow simulations represented in FIG. 27 illustrate that the method of flowing discrete sample volumes in the center of a microchannel produce less sample dispersion than for samples flowed near the edge of a microchannel. In particular, the time averaged sample concentration obtained for the flow simulation in the modeled asymmetric microchannel configuration depicted in FIG. 28 (i.e., trace 2700) was lower than for the flow simulation in the modeled symmetric microchannel configuration shown in FIG. 29 (i.e., trace 2702), which indicates that sample dispersion would be greater in an asymmetrically configured device. Thus, closer slug-to-slug spacing is generally possible in symmetrically configured devices, than in those which are asymmetrically configured, which leads to higher throughput.

COMPONENT SEPARATIONS

FIGS. 31–34 are data graphs showing the results of component separation assays, which illustrate the separation of larger components, such as fluorescently labeled latex beads and THP-1 cells from fluorescent dyes in bulk fluid flowing in the channels of the devices of the invention. The assays were performed in a device channel having a width of 100 $\mu$m and a depth of 20 $\mu$m. Incubation mixtures were introduced into the device via a capillary element having an internal diameter of 50 $\mu$m. See, e.g., FIG. 30A for a schematic depiction of such a device. The latex bead-based incubation mixture included 6 $\mu$m diameter fluorescent yellow beads from Spherotech, Inc., suspended in 1 $\mu$M cell buffer containing fluorescein dye at 1 $\mu$M. The cell-based incubation mixture included THP-1 cells dyed stained with a vital stain, 4 $\mu$M Calcein-am (Molecular Probes) for 15 minutes in a cell buffer (Hank's balanced salt solution buffered at pH 7 with HEPES, containing 10.8% Optiprep (NycoMed)). Samples of the bead and cell-based incubation mixtures were sequentially introduced by drawing aliquots of the mixtures for two seconds each into the device using a vacuum set at –1 psi or –0.5 psi, which corresponded, respectively, to 1.6 mm/second or 0.8 mm/second linear velocity of the beads or cells in channels. The fluorescent beads or cells were detected at a detection point downstream from the capillary element.

Figure 31:
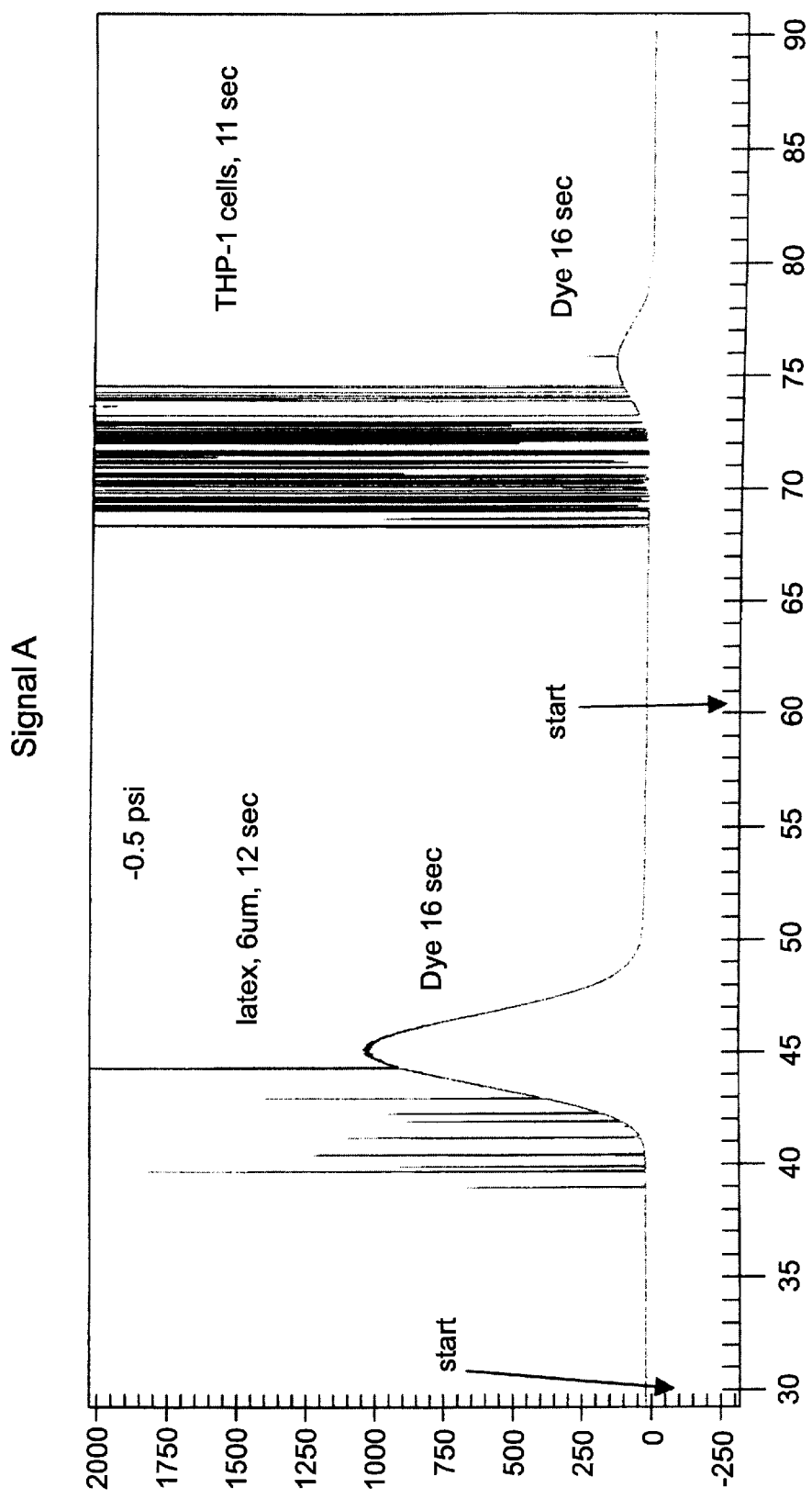
FIG. 31 is a data graph showing results of component separations performed using beads and cells flowed at –0.5 psi in a device.
Figure 32:
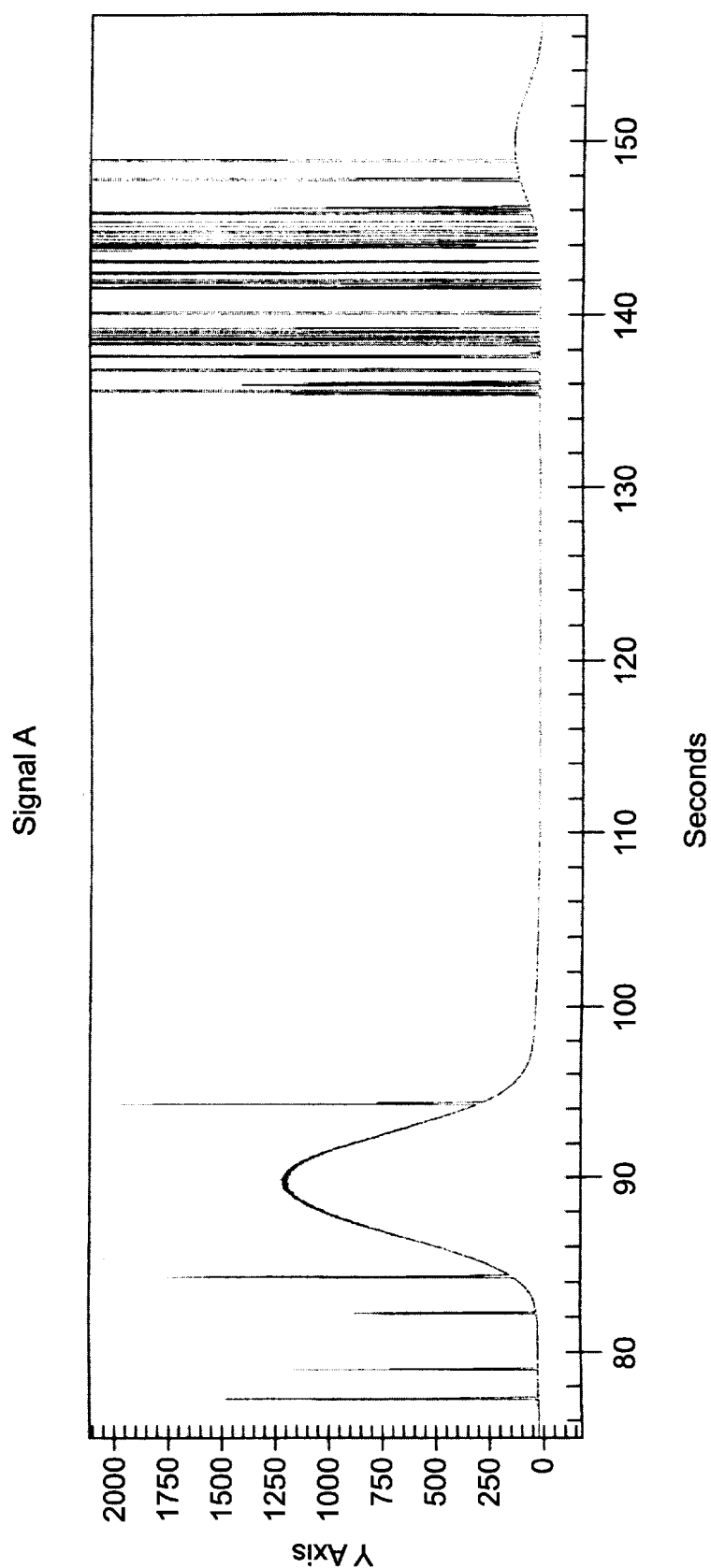
FIG. 32 is a data graph showing results of component separations performed using beads and cells flowed at –0.5 psi in a device.
Figure 33:
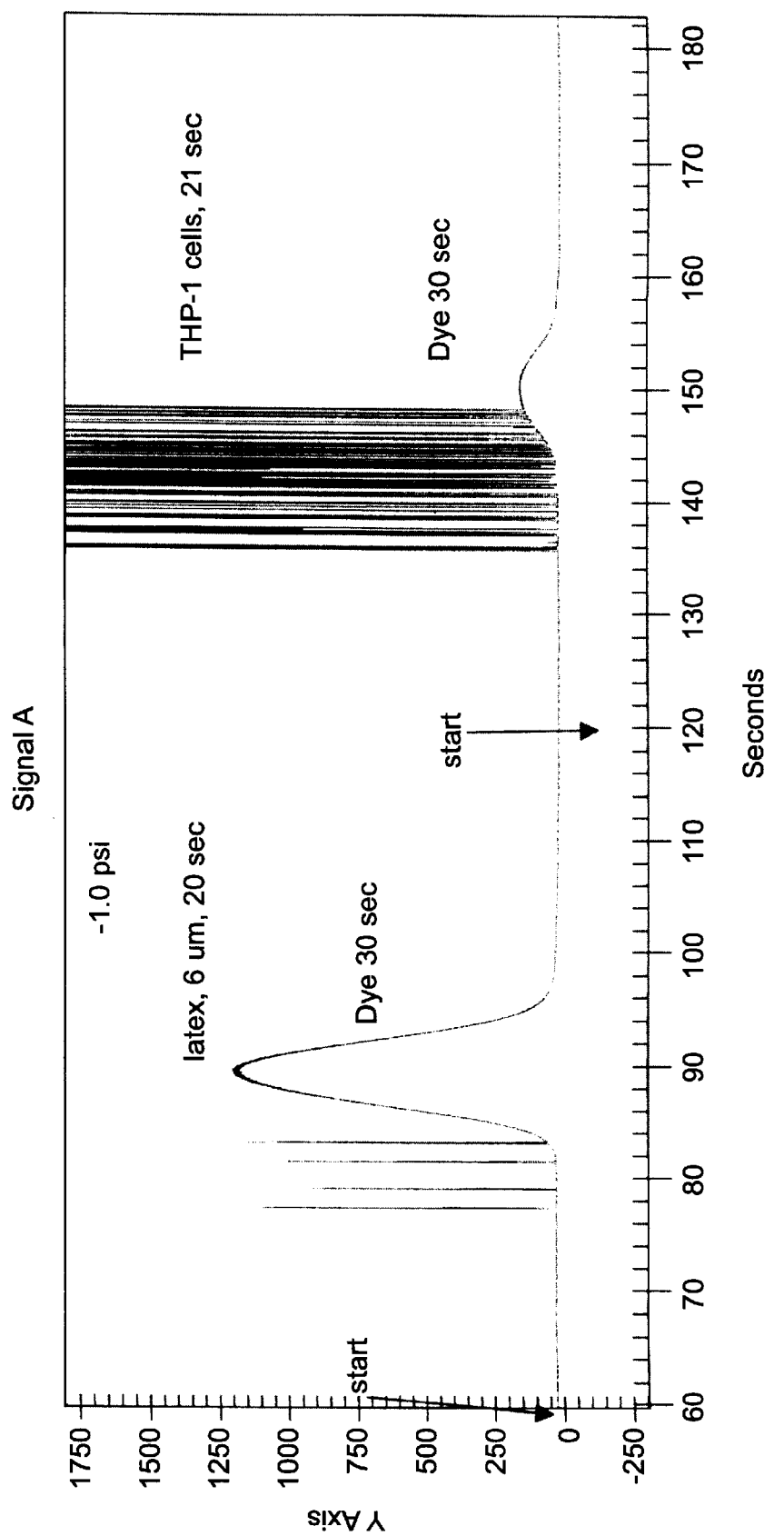
FIG. 33 is a data graph showing results of component separations performed using beads and cells flowed at –1.0 psi in a device.
Figure 34:
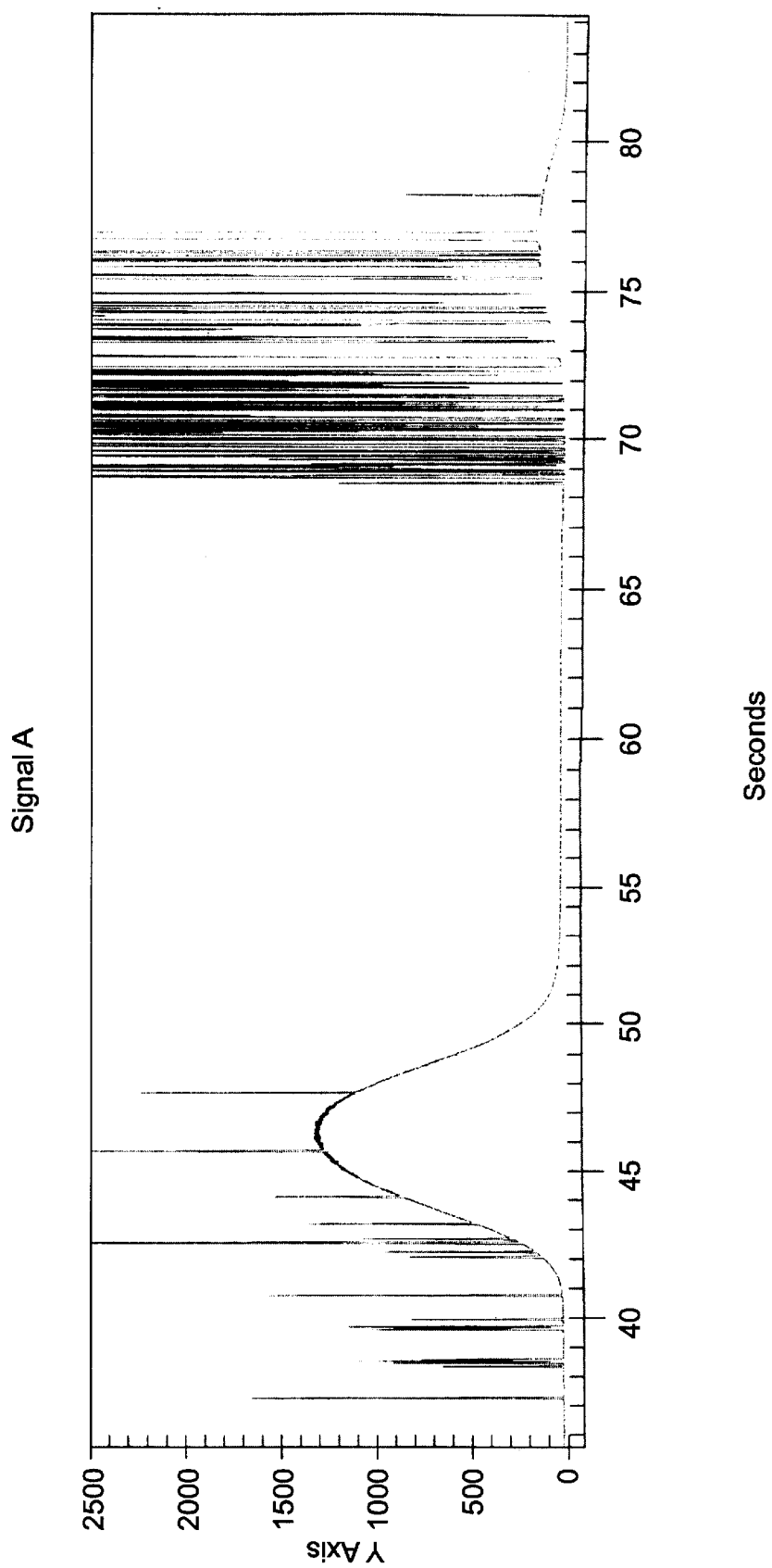
FIG. 34 is a data graph showing results of component separations performed using beads and cells flowed at –1.0 psi in a device.

In particular, FIG. 31 is a data graph showing the results of a pulse of the bead-based mixture followed, after about 30 seconds, by a pulse of the cell-based mixture flowed under a pressure of about –0.5 psi. FIG. 32 is a data graph showing the results of a pulse of the bead-based mixture followed, after about 60 seconds, by a pulse of the cell-based mixture flowed under a pressure of about –0.5 psi. FIG. 33 is a data graph showing the results of a pulse of the bead-based mixture followed, after about 60 seconds, by a pulse of the cell-based mixture flowed under a pressure of about –1.0 psi. FIG. 34 is a data graph showing the results of a pulse of the bead-based mixture followed, after about 30 seconds, by a pulse of the cell-based mixture flowed under a pressure of about –1.0 psi. The beads and cells were read over a background signal containing essentially no dye. The free or unbound dye was also immediately read following each set of particles. Baseline separations of dye and particles may be achieved in about a 20 second time period. As described above, the separation of bulk fluid and beads or cells rapidly in a microchannel may be used to perform immunoassays, hybridization assays, or the like in which assay sensitivity and detection limits are improved by separating bound ligand (e.g., a dye) from unbound or free ligand.

CELL BINDING ASSAYS

Figure 35:
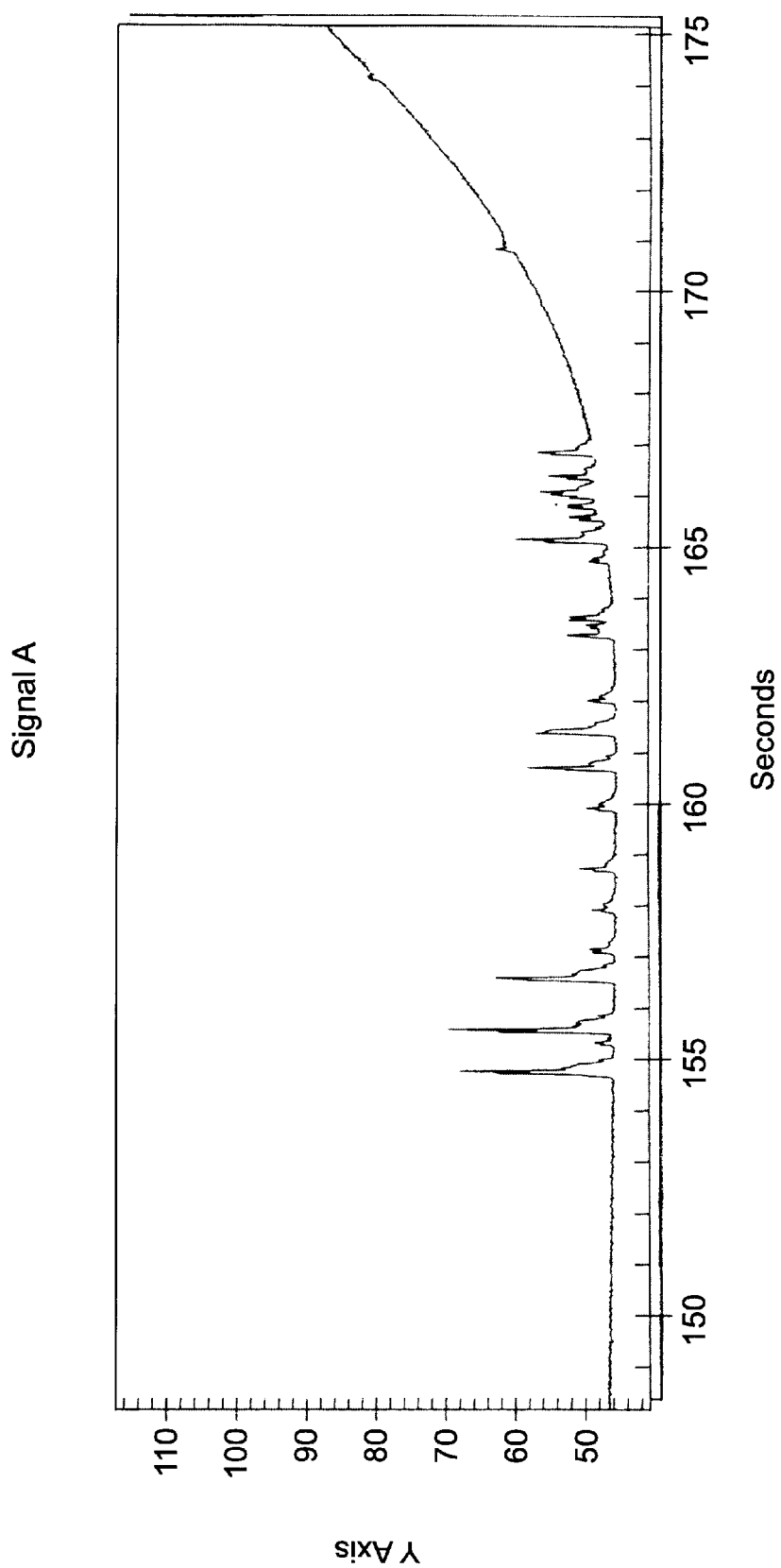
FIG. 35 is a data graph showing the results of a binding assay that involved anti-MHC-II antibodies and Jurkat cells that expressed MHC-II molecules.
Figure 36:
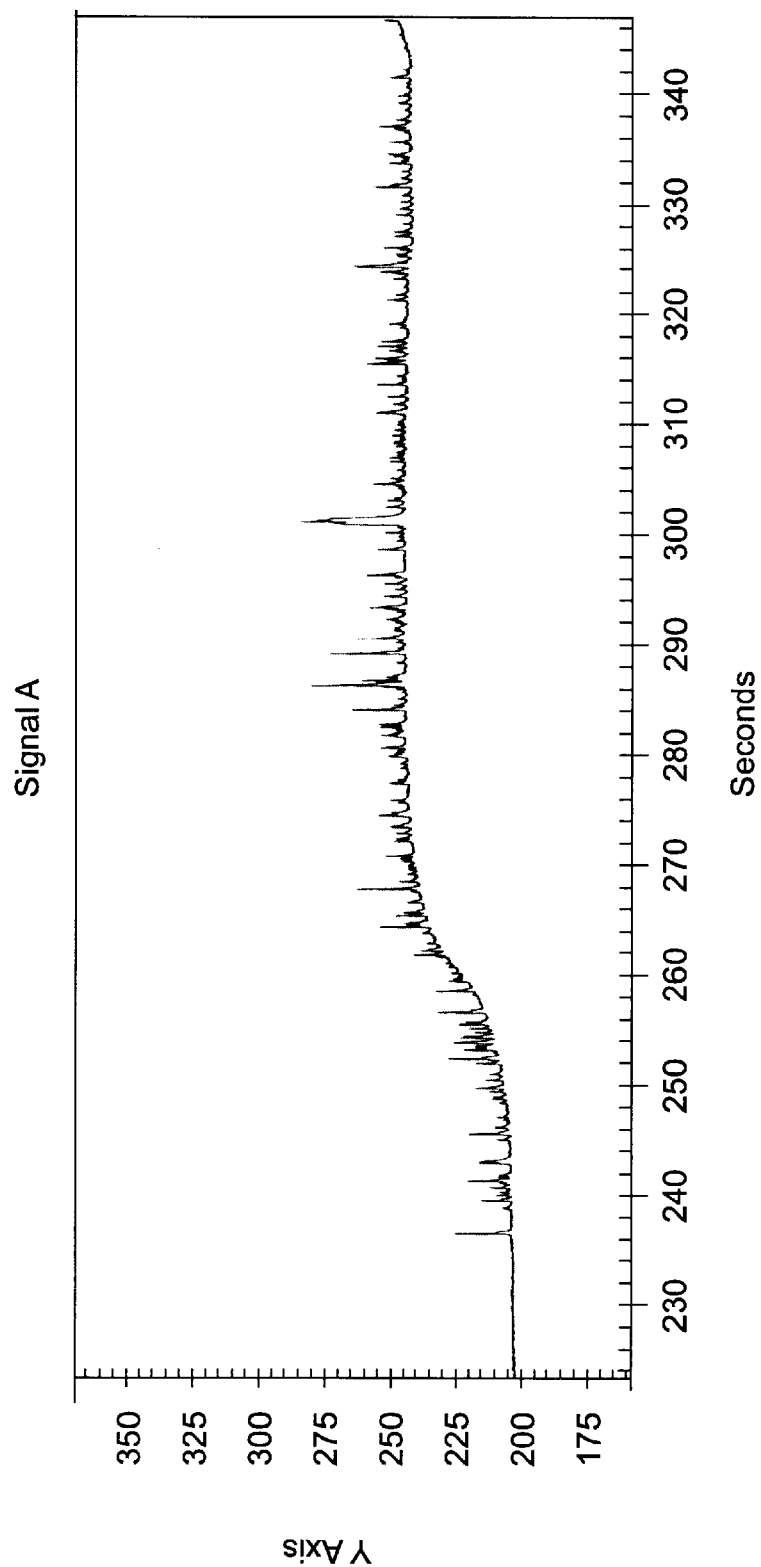
FIG. 36 is a data graph showing the results of a binding assay that involved anti-MHC-II antibodies and Jurkat cells that expressed MHC-II molecules.

FIGS. 35–39 are data graphs showing the results of various cellular binding assays performed using the same device used for the component separation described above. In particular, FIG. 35 is a data graph showing the results of a binding assay that involved an incubation mixture that included anti-MHC-II antibodies and Jurkat cells that expressed approximately 200,000 copies of MHC-II proteins per cell. The concentration of cells was about $5\times10^6$/ml. The introduced sample was a diluted by ½ in the device. This experiment involved a sample injection of about 10 seconds in which the cells were separated by cell dispersion as described above. A level of expression of about 100,000 copies of MHC class-II molecules on Jurkat cells is generally detectable without washing away any excess antibody. FIG. 36 is a data graph showing the results of a binding assay that involved the same incubation mixture of anti-MHC-II antibodies and Jurkat cells that expressed MHC-II proteins used in the experiment depicted in FIG. 35. This experiment involved a sample injection of about 100 seconds in which there was no dye separation.

Figure 37:
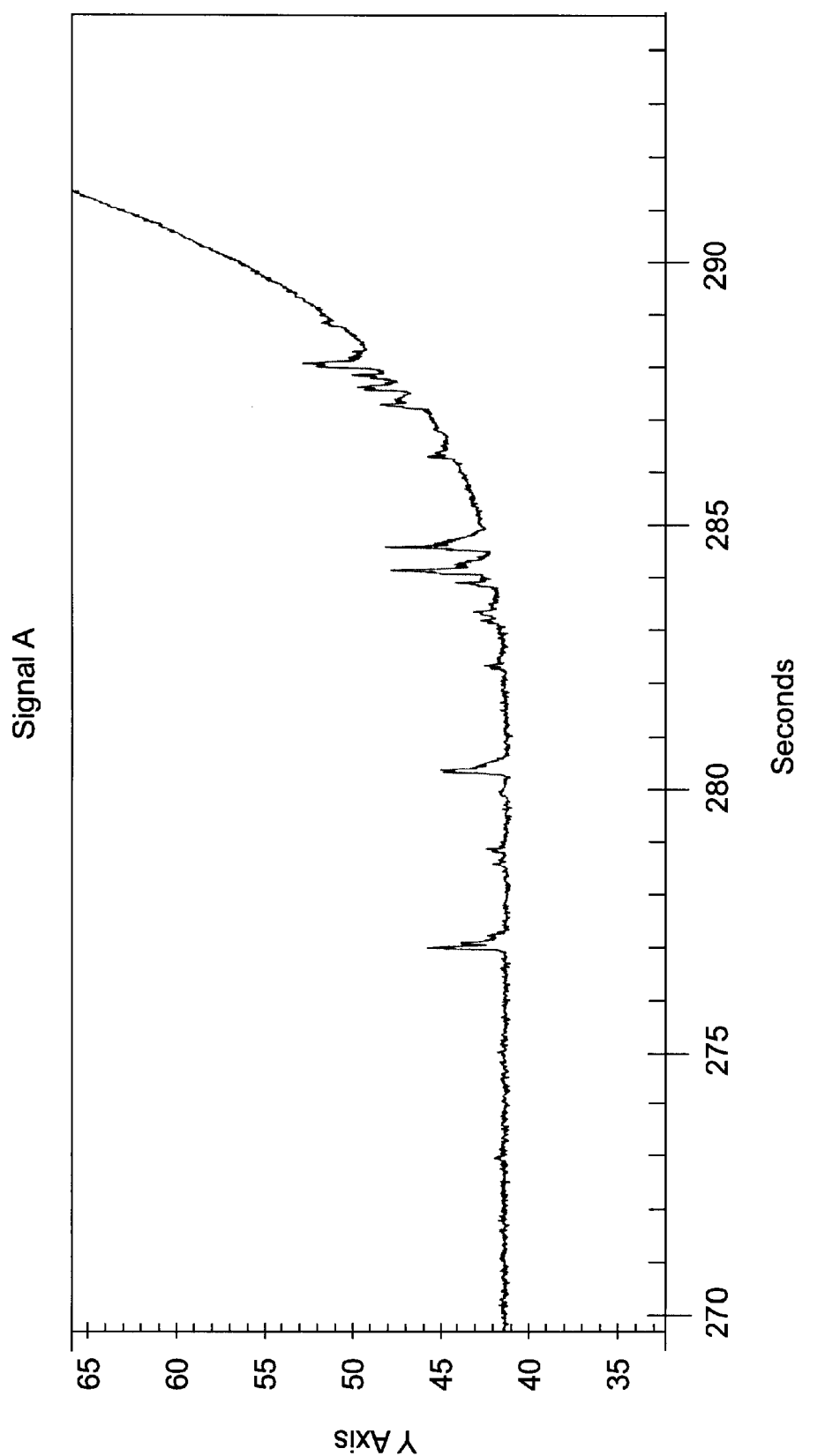
FIG. 37 is a data graph showing the results of a binding assay that involved anti-CD3 antibodies and Jurkat cells that expressed CD3 antigens.
Figure 38:
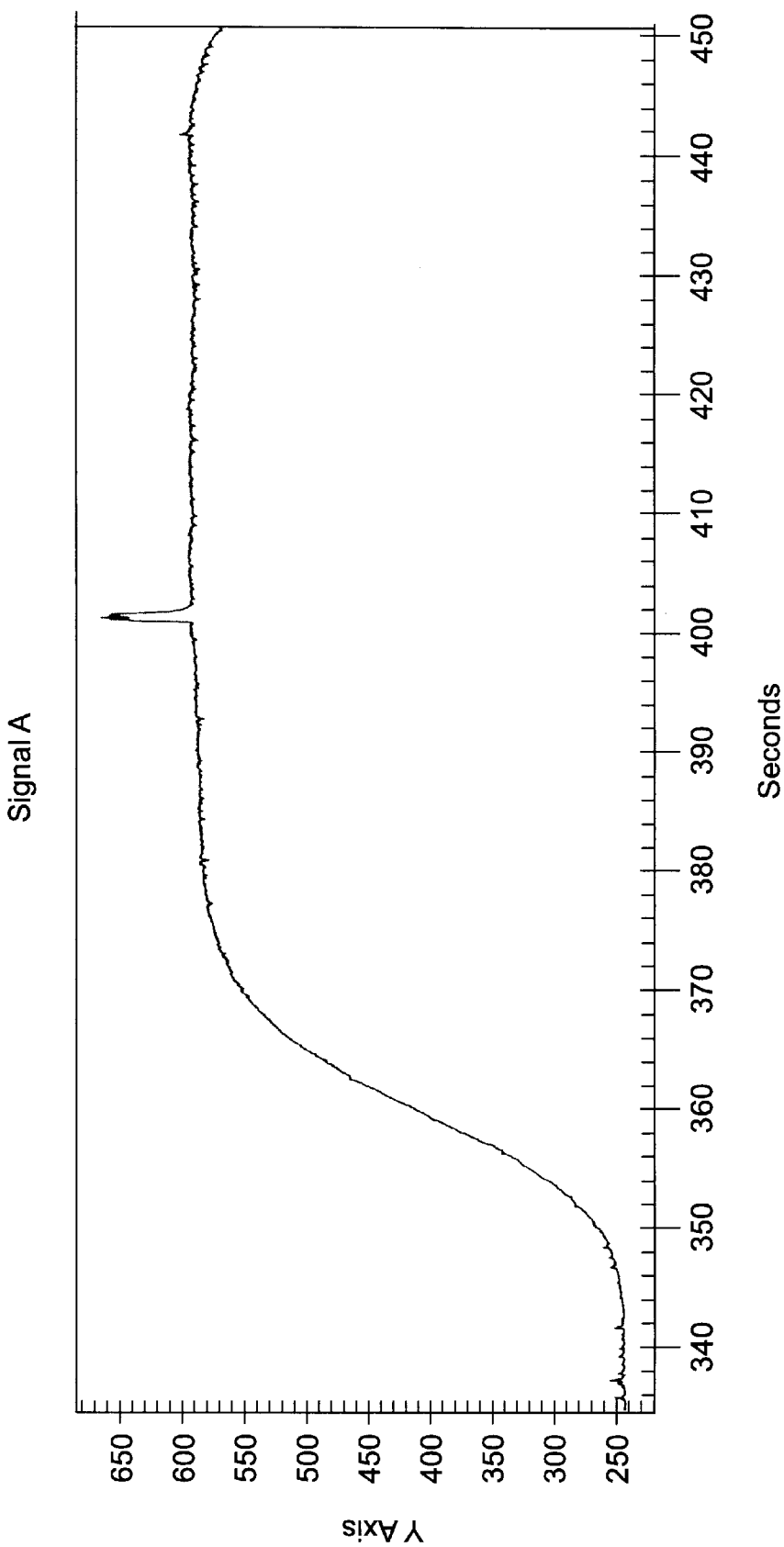
FIG. 38 is a data graph showing the results of a binding assay that involved anti-CD3 antibodies and Jurkat cells that expressed CD3 antigens.
Figure 39:
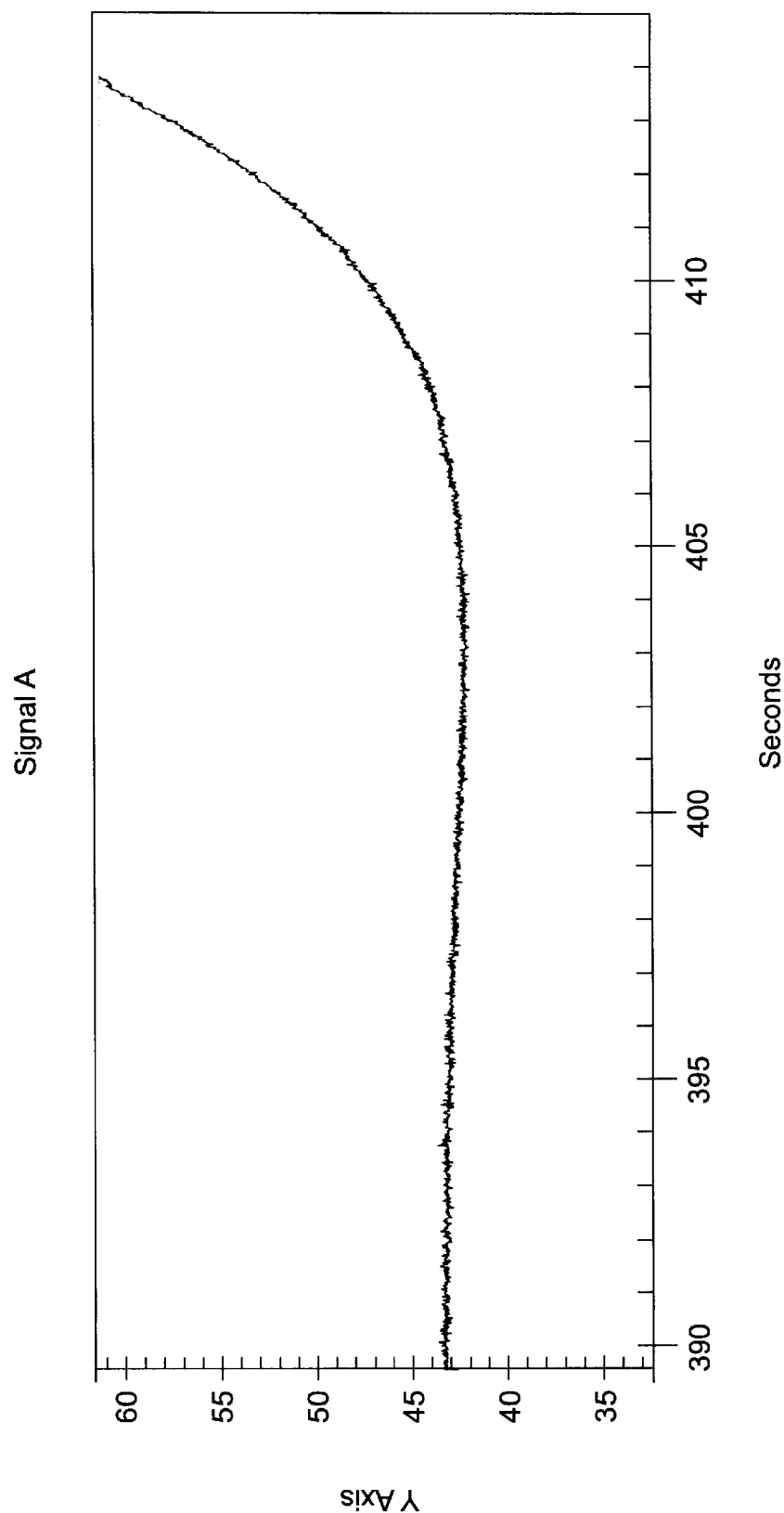
FIG. 39 is a data graph showing the results of a binding assay that involved anti-CD8 antibodies and Jurkat cells that did not express CD8 antigens.

FIG. 37 is a data graph showing the results of a binding assay that involved an incubation mixture that included anti-CD3 antibodies and Jurkat cells that expressed about 30,000 CD3 antigens per cell. The concentration of cells was about $5\times10^6$/ml. The introduced sample was a diluted by ½ in the device. This experiment involved a sample injection of about 10 seconds in which the cells were separated by cell dispersion as described above. A level of expression of about 10,000 copies of the CD-3 antigen on Jurkat cells is typically not detectable without washing away any excess antibody. FIG. 38 is a data graph showing the results of a binding assay that involved the same incubation mixture of anti-CD3 antibodies and Jurkat cells that expressed CD3 antigens used in the experiment depicted in FIG. 37. This experiment involved a sample injection cycle of about 100 seconds. FIG. 39 is a data graph showing the results of a binding assay control that involved anti-CD8 antibodies and Jurkat cells that did not express CD8 antigens. The concentration of cells was about $5\times10^6$/ml. The introduced sample was a diluted by ½ in the device. This experiment involved a sample injection cycle of about 10 seconds in which the cells were separated by cell dispersion as described above.

The discussion above is generally applicable to the aspects and embodiments of the invention described herein.

Moreover, modifications are optionally made to the methods and devices described herein without departing from the spirit and scope of the invention as claimed, and the invention is optionally put to a number of different uses including the following:

The use of a microfluidic system containing at least a first substrate and having a first channel and a second channel intersecting the first channel, at least one of the channels having at least one cross-sectional dimension in a range from 0.1 to 500 $\mu$m, in order to test the effect of each of a plurality of test compounds on a biochemical system comprising one or more focused cells or particles.

The use of a microfluidic system as described herein, wherein a biochemical system flows through one of said channels substantially continuously, providing for, e.g., sequential testing of a plurality of test compounds.

The use of a microfluidic device as described herein to modulate reactions within microchannels or microchambers.

The use of electrokinetic injection in a microfluidic device as described herein to modulate or achieve flow in the channels.

The use of a combination of wicks, electrokinetic injection and pressure based flow elements in a microfluidic device as described herein to modulate, focus, or achieve flow of materials, e.g., in the channels of the device.

An assay utilizing a use of any one of the microfluidic systems or substrates described herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patent applications and other documents cited in this application are incorporated by reference in their entirety for all purposes to the same extent as if each individual publication or patent document were individually so denoted.

What is claimed is:

1. A system for focusing and detecting particles flowing in a first microchannel, the system comprising:
   a body structure comprising at least first and second microchannels disposed therein which intersect at a first fluid junction;
   at least a first source of a sample fluid fluidly coupled to the first microchannel which comprises the particles;
   at least a second source of a focusing fluid fluidly coupled to the second microchannel;
   a fluid direction system operably coupled to the first and second microchannels which is configured to direct the sample fluid from the first fluid source into the first microchannel and to further direct the focusing fluid from the second fluid source into the second microchannel and into the fluid junction such that particles flowing in the sample fluid in the first microchannel are directed towards a first side of at least opposing first and second sides of the first microchannel;
   an interrogating light beam in sensory communication with the first side of the first microchannel at a first location which is downstream of the first fluid junction; and
   a detector which is configured to detect the particles in the focused sample fluid using the interrogating light beam.

2. The system of claim 1, further comprising at least one capillary element which extends from a surface of the body structure and which is fluidly coupled to at least one of the first and second microchannels.

3. The system of claim 1, wherein the fluid direction system comprises a pressure-based fluid flow controller.

4. The system of claim 1, wherein the fluid direction system comprises an electrokinetic-based fluid flow controller.

5. The system of claim 1, wherein the particles comprise one or more of: a cell, a set of cells, a microbead, a set of microbeads, a functionalized microbead, a set of functionalized microbeads, a molecule, or a set of molecules.

6. The system of claim 1, wherein the particles comprise cells.

7. The system of claim 1, wherein at least a portion of the first microchannel comprises at least one separation element disposed therein.

8. The system of claim 1, further comprising at least one collection well or a waste well fluidly coupled to the first microchannel downstream of the first location.

9. The system of claim 1, further comprising at least one third microchannel that intersects with the first microchannel downstream of the first location, whereby the fluid direction system is configured to direct at least a portion of the particles in the focused sample fluid into the at least one third microchannel.

10. The system of claim 1, wherein the first microchannel has at least one cross-sectional dimension of between about 5 and 25 microns.

11. The system of claim 1, wherein the first microchannel has at least one cross-sectional dimension of between about 10 and 100 microns.

12. The system of claim 1, wherein the detector comprises a fluorescent excitation source and a fluorescent emission detection element.

13. The system of claim 1, further comprising a computer operably coupled to the fluid direction system and the detector which comprises at least a first instruction set for converting detected signal information into digital data.

14. The system of claim 1, further comprising at least one heating element operably coupled to at least one of the second fluid source and the second microchannel.

15. The system of claim 14, wherein the at least one heating element comprises a joule heating electrode operably disposed within the second fluid source.

* * * * *